United States Patent
Hattori et al.

(10) Patent No.: US 11,026,612 B2
(45) Date of Patent: *Jun. 8, 2021

(54) INFORMATION PROCESSING SYSTEM, INFORMATION PROCESSING DEVICE, STORAGE MEDIUM STORING INFORMATION PROCESSING PROGRAM, AND INFORMATION PROCESSING METHOD

(71) Applicant: NINTENDO CO., LTD., Kyoto (JP)

(72) Inventors: Yurie Hattori, Kyoto (JP); Masahiro Kondo, Kyoto (JP)

(73) Assignee: NINTENDO CO., LTD., Kyoto (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/570,951

(22) Filed: Sep. 13, 2019

(65) Prior Publication Data

US 2020/0005915 A1 Jan. 2, 2020

Related U.S. Application Data

(63) Continuation of application No. 15/421,708, filed on Feb. 1, 2017, now Pat. No. 10,504,617, which is a
(Continued)

(30) Foreign Application Priority Data

Aug. 7, 2014 (WO) .................. PCT/JP2014/070931
Oct. 29, 2014 (WO) .................. PCT/JP2014/078824
(Continued)

(51) Int. Cl.
*A61B 5/16* (2006.01)
*G16H 40/63* (2018.01)
(Continued)

(52) U.S. Cl.
CPC ............... *A61B 5/16* (2013.01); *A47C 31/00* (2013.01); *A61B 5/0022* (2013.01); *A61B 5/024* (2013.01);
(Continued)

(58) Field of Classification Search
None
See application file for complete search history.

(56) References Cited

U.S. PATENT DOCUMENTS 6,809,653 B1 10/2004 Mann et al.
6,993,380 B1 1/2006 Modarres
(Continued)

FOREIGN PATENT DOCUMENTS

EP 2 570 976 3/2013
JP 9-34424 2/1997
(Continued)

OTHER PUBLICATIONS

Notice of Reasons for Refusal dated Feb. 3, 2020 in counterpart Japanese Patent Application No. 2018-196896 and English-language translation.
(Continued)

*Primary Examiner* — Kevin Y Kim
(74) *Attorney, Agent, or Firm* — Nixon & Vanderhye, P.C.

(57) ABSTRACT

An example information processing system executes a game application. The information processing system obtains user information for calculating information relating to sleep of a user, and calculates health information relating to sleep and/or fatigue of the user based on the obtained user information. The information processing system controls a game progress of the game application based on the health information.

15 Claims, 22 Drawing Sheets

Related U.S. Application Data continuation of application No. PCT/JP2015/061274, filed on Apr. 10, 2015.

(30) Foreign Application Priority Data

| | | | |
|---|---|---|---|
| Oct. 29, 2014 | (WO) | .................. | PCT/JP2014/078825 |
| Oct. 29, 2014 | (WO) | .................. | PCT/JP2014/078826 |
| Oct. 29, 2014 | (WO) | .................. | PCT/JP2014/078827 |
| Oct. 29, 2014 | (WO) | .................. | PCT/JP2014/078828 |
| Oct. 29, 2014 | (WO) | .................. | PCT/JP2014/078829 |

(51) Int. Cl.

| | |
|---|---|
| *G16H 50/30* | (2018.01) |
| *G16H 10/60* | (2018.01) |
| *G06F 16/22* | (2019.01) |
| *G06Q 30/02* | (2012.01) |
| *G16H 20/30* | (2018.01) |
| *G16H 40/67* | (2018.01) |
| *G16H 10/20* | (2018.01) |
| *G06Q 50/22* | (2018.01) |
| *A61B 5/00* | (2006.01) |
| *H04N 9/31* | (2006.01) |
| *A61B 5/11* | (2006.01) |
| *A61B 5/024* | (2006.01) |
| *G06Q 20/10* | (2012.01) |
| *A63F 13/212* | (2014.01) |
| *A47C 31/00* | (2006.01) |
| *A61B 5/0205* | (2006.01) |
| *G06Q 30/06* | (2012.01) |
| *A61B 5/08* | (2006.01) |

(52) U.S. Cl.

CPC .............. *A61B 5/0205* (2013.01); *A61B 5/11* (2013.01); *A61B 5/1118* (2013.01); *A61B 5/165* (2013.01); *A61B 5/4806* (2013.01); *A61B 5/486* (2013.01); *A61B 5/4809* (2013.01); *A61B 5/4812* (2013.01); *A61B 5/7271* (2013.01); *A61B 5/742* (2013.01); *A61B 5/7405* (2013.01); *A63F 13/212* (2014.09); *G06F 16/2228* (2019.01); *G06Q 20/10* (2013.01); *G06Q 30/02* (2013.01); *G06Q 30/0641* (2013.01); *G06Q 50/22* (2013.01); *G16H 10/20* (2018.01); *G16H 10/60* (2018.01); *G16H 20/30* (2018.01); *G16H 40/63* (2018.01); *G16H 40/67* (2018.01); *G16H 50/30* (2018.01); *H04N 9/3179* (2013.01); *H04N 9/3182* (2013.01); *H04N 9/3194* (2013.01); *A61B 5/08* (2013.01); *A61B 2560/0242* (2013.01)

(56) References Cited

U.S. PATENT DOCUMENTS

| | | |
|---|---|---|
| 8,170,609 B2 | 5/2012 | Hedtke et al. |
| 10,504,617 B2 | 12/2019 | Hattori et al. |
| 2001/0029535 A1 | 10/2001 | Hirano et al. |
| 2001/0049471 A1 | 12/2001 | Suzuki et al. |
| 2002/0024640 A1 | 2/2002 | Ioka |
| 2002/0063855 A1 | 5/2002 | Williams |
| 2002/0123908 A1 | 9/2002 | Ando et al. |
| 2003/0003988 A1 | 1/2003 | Walker et al. |
| 2003/0013981 A1 | 1/2003 | Gevins |
| 2003/0037124 A1 | 2/2003 | Yamaura et al. |
| 2004/0039254 A1 | 2/2004 | Stivoric |
| 2005/0061315 A1 | 3/2005 | Lee et al. |
| 2005/0258943 A1 | 11/2005 | Mian et al. |
| 2005/0264425 A1 | 12/2005 | Sato et al. |
| 2006/0071798 A1 | 4/2006 | Kiff |
| 2007/0016443 A1 | 1/2007 | Wachman et al. |
| 2007/0100595 A1 | 5/2007 | Earles et al. |
| 2007/0156060 A1 | 7/2007 | Cervantes |
| 2007/0287501 A1 | 12/2007 | Hoshina |
| 2008/0068158 A1 | 3/2008 | Sumiyoshi et al. |
| 2008/0146866 A1 | 6/2008 | Arai et al. |
| 2008/0162352 A1 | 7/2008 | Gizewski |
| 2008/0311968 A1 | 12/2008 | Hunter |
| 2008/0319855 A1 | 12/2008 | Stivoric et al. |
| 2009/0177327 A1 | 7/2009 | Turner et al. |
| 2009/0247834 A1 | 10/2009 | Schechter |
| 2010/0112955 A1 | 5/2010 | Krishnaswamy et al. |
| 2010/0216509 A1 | 8/2010 | Riemer et al. |
| 2010/0268551 A1 | 10/2010 | McNames |
| 2011/0015495 A1 | 1/2011 | Dothie et al. |
| 2011/0119080 A1 | 5/2011 | Hayter et al. |
| 2011/0137818 A1 | 6/2011 | Goad et al. |
| 2011/0166875 A1 | 7/2011 | Hayter et al. |
| 2011/0191158 A1 | 8/2011 | Kateraas et al. |
| 2011/0267196 A1 | 11/2011 | Hu |
| 2012/0083705 A1 | 4/2012 | Yuen et al. |
| 2012/0101889 A1 | 4/2012 | Kurata et al. |
| 2012/0157209 A1 | 6/2012 | Yamashita |
| 2012/0164946 A1 | 6/2012 | Fujiwara et al. |
| 2012/0215328 A1 | 8/2012 | Schmelzer |
| 2012/0253220 A1 | 10/2012 | Rai et al. |
| 2012/0265546 A1 | 10/2012 | Hwang et al. |
| 2012/0313791 A1 | 12/2012 | Mehta |
| 2012/0330556 A1 | 12/2012 | Shaanan et al. |
| 2013/0012234 A1 | 1/2013 | Tufty et al. |
| 2013/0095459 A1 | 4/2013 | Tran |
| 2013/0103416 A1 | 4/2013 | Amigo et al. |
| 2013/0138450 A1 | 5/2013 | Vigneux |
| 2013/0141235 A1 | 6/2013 | Utter, II |
| 2013/0245465 A1 | 9/2013 | Kasama |
| 2013/0280985 A1 | 10/2013 | Klein |
| 2014/0111690 A1 | 4/2014 | Kim |
| 2014/0173586 A1 | 6/2014 | Dugan |
| 2014/0198949 A1 | 7/2014 | Garlington et al. |
| 2014/0222101 A1 | 8/2014 | Miesel et al. |
| 2014/0247146 A1 | 9/2014 | Proud |
| 2014/0269224 A1 | 9/2014 | Huh |
| 2014/0274406 A1 | 9/2014 | Walkingstick |
| 2014/0276245 A1 | 9/2014 | Tsutsumi et al. |
| 2014/0316191 A1 | 10/2014 | de Zambotti et al. |
| 2014/0347366 A1 | 11/2014 | Emori et al. |
| 2014/0372133 A1 | 12/2014 | Austrum et al. |
| 2015/0018023 A1 | 1/2015 | Tomii et al. |
| 2015/0094544 A1 | 4/2015 | Spolin |
| 2015/0128353 A1 | 5/2015 | Kildey |
| 2015/0258301 A1 | 9/2015 | Trivedi et al. |
| 2016/0015315 A1 | 1/2016 | Auphan et al. |
| 2016/0151603 A1 | 6/2016 | Shouldice |
| 2016/0270718 A1 | 9/2016 | Heneghan et al. |

FOREIGN PATENT DOCUMENTS

| | | |
|---|---|---|
| JP | 10-48363 | 2/1998 |
| JP | 11-070097 | 3/1999 |
| JP | 2000-024324 | 1/2000 |
| JP | 2001-273376 | 10/2001 |
| JP | 2001-344352 | 12/2001 |
| JP | 2002-034955 | 2/2002 |
| JP | 2002-041930 | 2/2002 |
| JP | 2002-072359 | 3/2002 |
| JP | 2002-149830 | 5/2002 |
| JP | 2002-222264 | 8/2002 |
| JP | 2002-245178 | 8/2002 |
| JP | 2002-315738 | 10/2002 |
| JP | 2003-015665 | 1/2003 |
| JP | 2003-264812 | 9/2003 |
| JP | 2003-299624 | 10/2003 |
| JP | 2003-319910 | 11/2003 |
| JP | 2004-157596 | 6/2004 |
| JP | 2004-530195 | 9/2004 |
| JP | 2005-050253 | 2/2005 |
| JP | 2005-074107 | 3/2005 |
| JP | 2005-237569 | 9/2005 |

(56) References Cited

FOREIGN PATENT DOCUMENTS

| | | |
|---|---|---|
| JP | 2005-237719 | 9/2005 |
| JP | 2006-263002 | 10/2006 |
| JP | 2007-004000 | 1/2007 |
| JP | 2007-054596 | 3/2007 |
| JP | 2007-080219 | 3/2007 |
| JP | 2007-117365 | 5/2007 |
| JP | 2007-512086 | 5/2007 |
| JP | 2007-222276 | 9/2007 |
| JP | 2007-248052 | 9/2007 |
| JP | 2007-319238 | 12/2007 |
| JP | 2008-176741 | 7/2008 |
| JP | 2008-212391 | 9/2008 |
| JP | 2009-078070 | 4/2009 |
| JP | 2009-176130 | 8/2009 |
| JP | 2009-251452 | 9/2009 |
| JP | 2009-251452 | 10/2009 |
| JP | 2010-099173 | 5/2010 |
| JP | 2010-170534 | 8/2010 |
| JP | 2010-201113 | 9/2010 |
| JP | 2011-36649 | 2/2011 |
| JP | 2011-160327 | 8/2011 |
| JP | 2011-243041 | 12/2011 |
| JP | 2012-503804 | 2/2012 |
| JP | 2012-134737 | 7/2012 |
| JP | 2012-139362 | 7/2012 |
| JP | 2012-147879 | 8/2012 |
| JP | 2013-511780 | 4/2013 |
| JP | 2013-117941 | 6/2013 |
| JP | 2013-146463 | 8/2013 |
| JP | 2013-168026 | 8/2013 |
| JP | 2013-182422 | 9/2013 |
| JP | 2013-192620 | 9/2013 |
| JP | 2013-537435 | 10/2013 |
| JP | 2013-257837 | 12/2013 |
| JP | 2014-052834 | 3/2014 |
| WO | 02/073864 | 9/2002 |
| WO | 2005/055802 | 6/2005 |
| WO | WO 2005/055802 | 6/2005 |
| WO | WO 2005/094667 | 10/2005 |
| WO | WO 2007/023818 | 3/2007 |
| WO | 2008/096307 A1 | 8/2008 |
| WO | 2010/036700 | 4/2010 |
| WO | WO 2010/036700 | 4/2010 |
| WO | 2011/136253 | 11/2011 |
| WO | 2011/150362 | 12/2011 |
| WO | WO 2011/150362 | 12/2011 |
| WO | WO 2011/156272 | 12/2011 |
| WO | 2012/006549 | 1/2012 |
| WO | 2013/065246 | 5/2013 |
| WO | 2013/065504 A1 | 5/2013 |
| WO | WO 2013/080109 | 6/2013 |

OTHER PUBLICATIONS

Notice of Reasons for Refusal dated Oct. 29, 2019 in Japanese Patent Application No. 2019-007669 and English-language translation.
English-language machine translation of JP2007-004000.
Final Office Action dated Dec. 20, 2019 in U.S. Appl. No. 15/211,300 and PTO-892 Form.
Notice of Reasons for Refusal dated Feb. 6, 2020 in Japanese Application No. 2018-221951 with English-language machine translation.
Ouchi, Kazushige et al., "Healthcare services using a wearable device", IPSJ SIG Technical Reports, Japan, Information Processing Society of Japan, Feb. 23, 2007, vol. 2007, No. 14, pp. 29-36.
English-language machine translation of JP2009-176130.
Final Office Action dated Feb. 7, 2020 in U.S. Appl. No. 15/211,146.
Final Office Action dated Mar. 18, 2020 in U.S. Appl. No. 15/211,265 and PTO-892 form.
Office Action dated Apr. 9, 2020 in U.S. Appl. No. 15/211,300.
Final Office Action dated Apr. 30, 2020 in U.S. Appl. No. 15/211,122.
Office Action dated Sep. 25, 2019 in U.S. Appl. No. 15/421,724 and PTO-892 form.
Office Action dated Oct. 21, 2019 in U.S. Appl. No. 15/211,387 and PTO-892 Form.
Office Action dated Sep. 28, 2020 in Japanese Patent Application No. 2019-172746 and English-language translation.
English-language machine translation of JP11-070097.
Notice of Allowance dated Jun. 23, 2020 in U.S. Appl. No. 15/211,182.
M. Sato et al., "Wireless Sensor Systems" $1^{st}$ Edition, Tokyo Denki University Press, Oct. 30, 2012, pp. 186 and 196.
Kawai et al., U.S. Appl. No. 15/211,122, filed Jul. 15, 2016 (149 pages).
Kawai et al., U.S. Appl. No. 15/211,146, filed Jul. 15, 2016 (130 pages).
Kawai et al., U.S. Appl. No. 15/211,182, filed Jul. 15, 2016 (214 pages).
Kawai et al., U.S. Appl. No. 15/211,265, filed Jul. 15, 2016 (219 pages).
Kawai et al., U.S. Appl. No. 15/211,300, filed Jul. 15, 2016 (209 pages).
Kawai et al., U.S. Appl. No. 15/211,387, filed Jul. 15, 2016 (218 pages).
Kawai et al., U.S. Appl. No. 15/211,497, filed Jul. 15, 2016 (210 pages).
Hattori., U.S. Appl. No. 15/421,724, filed Feb. 1, 2017 (183 pages).
English translation of International Preliminary Report on Patentability issued in PCT/JP2014/078824 dated Jul. 19, 2016 (14 pages).
English translation of International Preliminary Report on Patentability issued in PCT/JP2014/078825 dated Jul. 19, 2016 (14 pages).
Office Action dated Jun. 8, 2017 issued in co-pending U.S. Appl. No. 15/211,497 (15 pgs.).
European Search Report dated Aug. 7, 2017, issued in corresponding EP Application No. 14878426.7 (9 pages).
Extended European Search Report dated Sep. 12, 2017 issued in European Patent Application No. 14878891.2 (9 pgs.).
Julie Guan "All-in Pedometer iPhone app review AppSafari", XP055403538, Jan. 25, 2011 (8 pgs.).
Partial Supplementary European Search Report dated Sep. 5, 2017 issued in European Application No. 14878971.2 (7 pages).
Office Action dated Jan. 12, 2018 issued in co-pending U.S. Appl. No. 15/211,497 (24 pgs.).
Extended European Search Report dated Mar. 9, 2018 issued in European Application No. 15830638.1 (11 pgs.).
Office Action dated Jun. 21, 2018 issued in U.S. Appl. No. 15/211,497.
Office Action dated Aug. 16, 2018 issued in corresponding Japanese Application No. 2015-557699 (8 pages).
Office Action dated Aug. 27, 2018 issued in U.S. Appl. No. 15/211,300 (28 pgs.).
Office Action dated Aug. 31, 2018 issued in U.S. Appl. No. 15/211,265 (36 pages).
Office Action dated Oct. 4, 2018 issued in U.S. Appl. No. 15/211,387 (37 pgs.).
Office Action dated Oct. 24, 2018 issued in JP Application No. 2015-557716 (3 pgs.).
Office Action—Notice of Reasons for Refusal dated Nov. 5, 2018 issued in JP Application No. 2015-557713 (4 pages).
Office Action dated Nov. 29, 2018 issued in U.S. Appl. No. 15/211,122 (16 pgs.).
Final Office Action dated Jan. 25, 2019, issued in Kawai, et al., U.S. Appl. No. 15/211,300 (31 pages).
Office Action dated Feb. 1, 2019 issued in U.S. Appl. No. 15/211,182 (13 pgs.).
Final Office Action dated Mar. 7, 2019 in U.S. Appl. No. 15/211,497.
Notice of Reasons for Refusal dated Mar. 13, 2019 in counterpart Japanese Patent Application No. 2015-557714 and English-language translation.
English-language machine translation of JP2009-251452.
Decision of Refusal dated Mar. 19, 2019 in counterpart Japanese Patent Application No. 2015-557713 0.
Decision of Dismissal of Amendment dated Mar. 19, 2019 in counterpart Japanese Patent Application No. 2015-5577130.
English-language machine translation of JP2002-041930.

(56) References Cited

OTHER PUBLICATIONS

English-language machine translation of JP2003-264812.
Office Action dated Apr. 12, 2019 in U.S. Appl. No. 15/421,724.
Advisory Action and Interview Summary dated May 17, 2019 in U.S. Appl. No. 15/211,300.
Communication dated Jun. 24, 2019 in European Patent Application No. 14878891.2.
Purewal, Sara, "Review: Runtastic's mobile apps make tracking a workout easier PCWorld," Nov. 29, 2012, XP055598914, retrieved from the internet: https://pcworld.com/article/2017159/review-runtastics-mobile-apps-make-tracking-a-workout-easier.html, retrieved on Jun. 24, 2019.
Office Action dated Aug. 23, 2019 in U.S. Appl. No. 15/211,146 and Form PTO-892.
U.S. Appl. No. 15/211,300, filed Jul. 15, 2016.
U.S. Appl. No. 15/211,497, filed Jul. 15, 2016.
U.S. Appl. No. 15/211,387, filed Jul. 15, 2016.
U.S. Appl. No. 15/211,146, filed Jul. 15, 2016.
U.S. Appl. No. 15/211,122 , filed Jul. 15, 2016.
U.S. Appl. No. 15/211,182, filed Jul. 15, 2016.
U.S. Appl. No. 15/211,265, filed Jul. 15, 2016.
U.S. Appl. No. 15/421,708, filed Feb. 1, 2017.
U.S. Appl. No. 15/421,724, filed Feb. 1, 2017.
Final Office Action dated Nov. 2, 2020 in U.S. Appl. No. 15/211,146 and PTO-892 form.
Notice of Reasons for Refusal dated Apr. 2, 2021 in Japanese Patent Application No. 2019-172746 and English-language translation.
English-language machine translation of JP2000-024324.

INFORMATION PROCESSING SYSTEM, INFORMATION PROCESSING DEVICE, STORAGE MEDIUM STORING INFORMATION PROCESSING PROGRAM, AND INFORMATION PROCESSING METHOD

CROSS REFERENCE TO RELATED APPLICATIONS

This application is a continuation application of U.S. patent application Ser. No. 15/421,708, now U.S. Pat. No. 10,504,617, filed on Feb. 1, 2017, which is a continuation application of International Application No. PCT/JP2015/061274, filed on Apr. 10, 2015, which designated the U.S. and claims priority to International Application Nos. PCT/JP2014/070931 filed on Aug. 7, 2014, PCT/JP2014/078824 filed on Oct. 29, 2014, PCT/JP2014/078825 filed on Oct. 29, 2014, PCT/JP2014/078826 filed on Oct. 29, 2014, PCT/JP2014/078827 filed on Oct. 29, 2014, PCT/JP2014/078828 filed on Oct. 29, 2014 and PCT/JP2014/078829 filed on Oct. 29, 2014, the entire contents of each of which are hereby incorporated by reference.

FIELD

The present technique relates to an information processing system, an information processing device, a storage medium storing an information processing program and an information processing method for measuring health information of the user.

BACKGROUND AND SUMMARY

There are conventional techniques for measuring the sleep of the user and performing an analysis relating to the sleep of the user based on the measurement result.

When an analysis relating to the health of the user, such as the sleep-related analysis mentioned above, is performed, it is preferred that the user continuously checks the measurement or analysis results.

In view of this, the present application discloses an information processing system, an information processing device, a storage medium storing an information processing program and an information processing method, with which it is possible to motivate the user to continuously check the results of measurement and/or analysis of health-related information.

(1)
An example information processing system described herein executes a game application. The information processing system includes an obtaining unit, an information calculation unit and a game execution unit. The obtaining unit obtains user information for calculating information relating to sleep of a user. The information calculation unit calculates health information relating to sleep and/or fatigue of the user based on the obtained user information. The game execution unit controls game progress of the game application based on the health information.

(2)
The game execution unit may control progress of a story of a game in the game application based on the health information.

(3)
The game execution unit may allow a parameter of an object appearing in the game application to improve in accordance with the health information.

(4)
The game execution unit may control the game progress in response to health information satisfying a predetermined condition being calculated.

(5)
The information calculation unit may determine that the user has awakened or gotten out of bed based on the obtained user information.

The information processing system may further include a wake-up game processing unit, wherein in response to the determination that the user has awakened or gotten out of bed, the wake-up game processing unit starts accepting an instruction input for starting execution of a predetermined wake-up game and, when there is said instruction input, the wake-up game processing unit executes a wake-up game process based on an operation input from the user.

(6)
When the wake-up game is executed, the information calculation unit may accept an instruction input for starting execution of the wake-up game on a condition of being within a predetermined period of time from a point in time when it is determined that the user has awakened or gotten out of bed.

(7)
The game execution unit may execute a game process relating to the game progress based on a result of the wake-up game.

(8)
The information calculation unit may calculate, as the health information, fatigue-related information of the user based on an input made by the user in the wake-up game process and a sleep-related state of the user.

(9)
The obtaining unit may obtain the user information during a plurality of sleep periods of the user. For each of the plurality of sleep periods of the user, the information calculation unit may calculate health information based on the user information obtained in said sleep period. The game execution unit may control the game progress based on a comparison result between new health information relating to a latest sleep period and health information relating to a past sleep period that is prior to said sleep period.

(10)
The game execution unit may control the game progress based on a difference between a numerical value based on the new health information and a numerical value based on the past health information.

(11)
The game execution unit may determine whether or not the new health information is improved from the past health information by a predetermined reference level or more, and control the game progress based on the determination result.

(12)
The information processing system is capable of accessing a storage section storing health information relating to a plurality of users. The game execution unit may control the game progress based on a comparison result between health information calculated by the information calculation unit and health information relating to another user stored in the storage section.

(13)
Another example information processing system described herein executes an application. The information processing system includes an obtaining unit, an information calculation unit and a display control unit. The obtaining unit obtains user information for calculating information relating to sleep of a user. The information calculation unit calculates a plurality of different health information relating to sleep and/or fatigue of the user based on the obtained user information. The display control unit generates, in the application, an image of an object that changes depending on each of the plurality of health information and displays the image on a predetermined display device.

(14)

The information calculation unit may determine that the user has awakened or gotten out of bed. In response to the determination that the user has awakened or gotten out of bed, the display control unit may automatically display the image on the display device.

(15)

The display control unit may change a display mode of a first type relating to a predetermined object appearing in the application depending on first health information of the plurality of health information, and change a display mode of a second type relating to the object depending on second health information of the plurality of health information.

(16)

The obtaining unit may obtain the user information over a plurality of sleep periods of the user. For each of the plurality of sleep periods of the user, the information calculation unit may calculate health information based on the user information obtained in said sleep period. The display control unit may generate the image based on a comparison result between new health information relating to the latest sleep period and information based on health information relating to a past sleep period prior to said sleep period.

(17)

The display control unit may generate the image based on a difference between a numerical value based on the new health information and a numerical value based on the past health information.

(18)

The display control unit may determine whether or not the new health information has improved by a predetermined reference level or more from the past health information to generate the image based on the determination result.

(19)

The information processing system may be capable of accessing a storage section that stores various health information relating to a plurality of users. The display control unit may make a comparison, for each of the various health information, between the health information calculated by the information calculation unit and the health information relating to other users stored in the storage section to generate the image based on the comparison result.

(20)

The application may be a game application. The information calculation unit may calculate health information relating to sleep and/or fatigue of the user based on the user information. The display control unit may present a part of the health information as a game element to the user and also present the same part or a different part of the health information as an index representing health to the user.

(21)

The information calculation unit may make an evaluation relating to sleep and/or fatigue of the user to calculate health information representing the evaluation result. The information processing system may further include a presenting unit that generates advice information and/or recommendation information for improving the evaluation based on the evaluation result to present the advice information and/or recommendation information to the user.

(22)

The information calculation unit may calculate, as the health information, at least some of 1. to 15. below:
 1. amount of time from when getting in bed to sleep onset;
 2. amount of time from awakening to getting out of bed;
 3. ratio of an amount of time of deep sleep with respect to a predetermined period of time since sleep onset;
 4. ratio of an amount of time of light sleep with respect to a predetermined period of time until awakening;
 5. REM sleep cycle;
 6. ratio between REM sleep time and non-REM sleep time;
 7. sleep time;
 8. difference between ideal sleep onset timing and actual sleep onset timing;
 9. difference between ideal awakening timing and actual awakening timing;
 10. the number of mid-sleep awakenings;
 11. timing of mid-sleep awakenings;
 12. wake time after sleep onset;
 13. the number of times of tossing and turning;
 14. level of snoring; and
 15. environment during sleep.

(23)

The information processing system may include a sensor, a terminal device having a display device, and a server capable of communicating with the terminal device via a network. The terminal device may obtain the user information from the sensor, and display an image of the application on the display device. The server may accumulate the health information.

(24)

The information processing system may further include a notification unit that makes a notification inducing the user to awaken.

(25)

The obtaining unit may obtain the user information from a sensor that senses at least one of pulse, breathing and body movements of the user.

(26)

The information processing system may further include a sensor that senses biological information of the user while being not in contact with the user. The obtaining unit may obtain biological information as the user information from the sensor.

(27)

The sensor may discharge radio waves or acoustic waves toward an object to be sensed and receive reflected waves so as to output the biological information based on the reception result.

(28)

The sensor may be a Doppler sensor.

Note that the present specification discloses an example information processing device (e.g., a hand-held terminal) and an example server included in the information processing system as set forth in (1) to (28) above. The present specification also discloses an example storage medium storing an information processing program that causes the computer of the information processing device or the server to function as some of the various units set forth in (1) to (28) above. The present specification also discloses an information processing method to be carried out in the information processing system, the information processing device or the server.

With the information processing system, the information processing device, the storage medium storing an information processing program and the information processing method set forth above, it is possible to motivate the user to continuously check the results of measurement and/or analysis of health-related information.

These and other objects, features, aspects and advantages will become more apparent from the following detailed description when taken in conjunction with the accompanying drawings.

DETAILED DESCRIPTION OF NON-LIMITING EXAMPLE EMBODIMENTS

1. Configuration of Information Processing System

Figure 1:
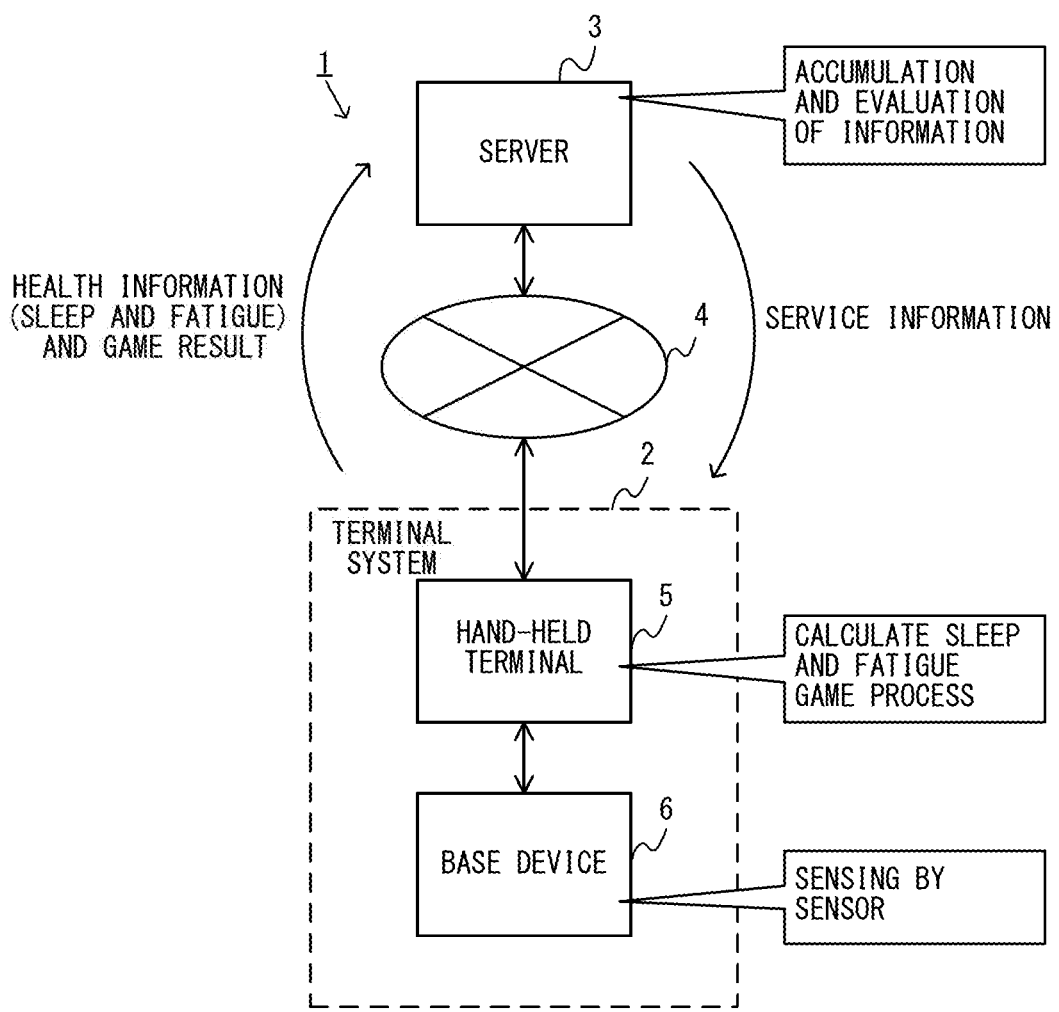
FIG. 1 is a block diagram showing an example configuration of an information processing system of the present embodiment.

In the following, with reference to the drawings, an information processing system, an information processing device, an information processing program, and an information processing method according to the present embodiment will be described. First, the overall configuration of the information processing system according to the present embodiment will be described. FIG. 1 is a block diagram showing one example of the configuration of an information processing system according to the present embodiment. As shown in FIG. 1, an information processing system 1 includes a terminal system 2 and a server 3. The terminal system 2 and a server 3 can communicate with each other through a network 4 such as the Internet and a mobile communication network. It should be noted that although only a single terminal system 2 is shown in FIG. 1, the information processing system 1 in the present embodiment includes multiple terminal systems each provided to a user. The information processing system of the present embodiment aims at allowing the user to manage the user's own healthcare as if by playing a video game.

The terminal system 2 is for managing the user's healthcare. The terminal system 2 calculates sleep- and fatigue-related information, as health information relating to the health and/or body of the user, during the user's sleep, the details of which will be described later. In the present embodiment, the terminal system 2 includes a hand-held terminal 5 and a base device 6, and the hand-held terminal 5 calculates the health information based on the information sensed by the base device 6 using sensors (see FIG. 1). The terminal system 2 presents, to the user, the calculation results, and information based on the calculation results (e.g., advice, etc.).

In the present embodiment, the terminal system 2 executes a game application in order to incorporate a gamification factor into users' healthcare. That is, the terminal system 2 executes a game application, thereby executing a game process using the health information described above as a game input (see FIG. 1). The terminal system 2 uploads, to the server 3, the health information and the information of the game result (see FIG. 1).

The server 3 stores (or accumulates) the information uploaded from the terminal system 2. In the present embodiment, the server 3 obtains and stores information (e.g., the health information and the information of the game result) relating to different users from a plurality of terminal systems. The server 3 provides network services to each user based on the stored information. For example, the server 3 transmits, to the terminal system 2, information (e.g., service information) for providing network services in accordance with the sleep or fatigue state of the user (see FIG. 1). The service information is, for example, information relating to a privilege to be given to the user (which may be a privilege in a network service or a privilege in the game application). The service information may also be information of advice for the user, information of recommendation for the user, data of a content item to be provided to the user, etc. The server 3 may transmit health information relating to another user to the terminal system 2 (e.g., in response to a request from the terminal system 2).

As described above, according to the present embodiment, the terminal system 2 calculates the user health information (specifically, sleep/fatigue information), and executes a game using health information as a game input. The server 3 also provides a network service, based on the health information and the game result, to the user (in other words, the terminal system 2).

Figure 2:
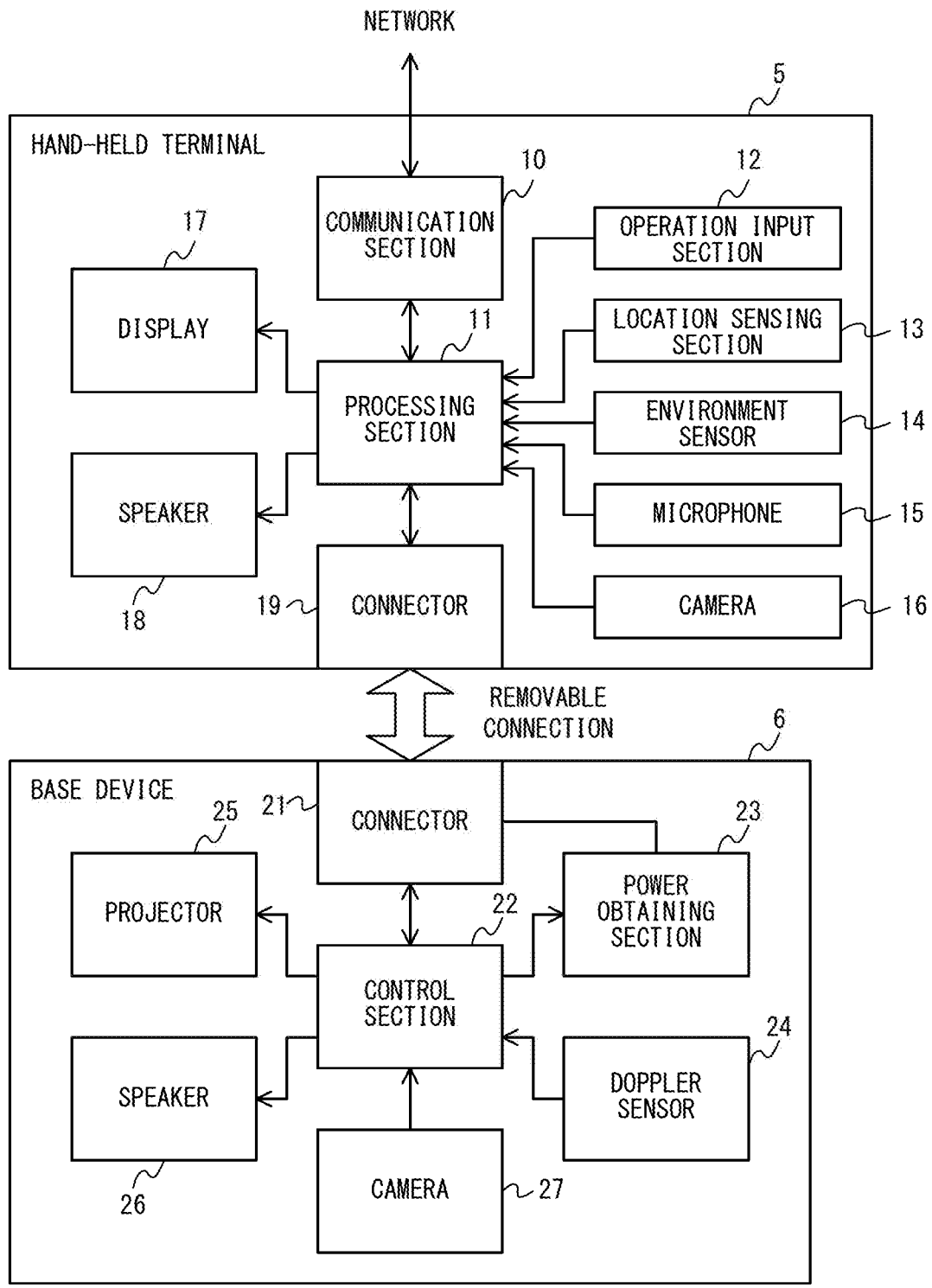
FIG. 2 shows an example detailed configuration of a terminal system.
Figure 3:
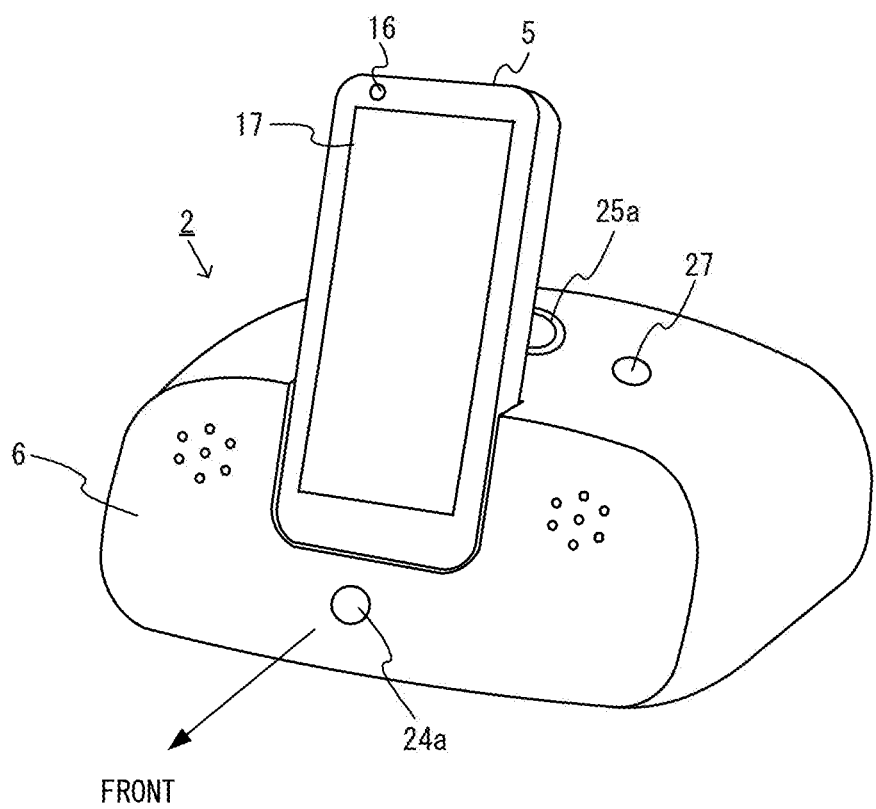
FIG. 3 shows an example external appearance of a terminal system.

Next, one example of the configuration of the terminal system 2 will be described. FIG. 2 shows one example of the detailed configuration of the terminal system 2. FIG. 3 shows one example of the external appearance of the terminal system 2. As shown in FIGS. 1 to 3, the terminal system 2 includes the hand-held terminal 5 and the base device 6. The hand-held terminal 5 is carried by the user. The base device 6 is placed in the house of the user, for example.

In the present embodiment, the hand-held terminal 5 is a hand-held type information processing device, and the base device 6 is a cradle that is connectable to the hand-held terminal 5. As shown in FIG. 3, the hand-held terminal 5 can connect to the base device 6 in a detachable/reattachable manner. In addition, the base device 6 has a function of performing charging with regard to the hand-held terminal 5, and, when the hand-held terminal 5 and the base device 6 are connected, charging of the hand-held terminal 5 by the base device 6 becomes possible. In other embodiments, a configuration in which the hand-held terminal 5 and the base device 6 are detachably/reattachably connected via a cable may be used.

There is no particular limitation on the communication method between the hand-held terminal 5 and the base device 6, and it may be wired communication via a cable or wireless communication such as radio wave communication and infrared communication. The communication between the hand-held terminal 5 and the base device 6 may be performed by a communication method in which communication is made directly therebetween or may be performed by a communication method in which communication is made via a network such as a LAN or the Internet.

First, the configuration of the hand-held terminal 5 in the present embodiment will be described. The hand-held terminal 5 is a hand-held type information processing device, and, in the present embodiment, is a multifunctional device such as, for example, a mobile phone, a smart phone, or a tablet terminal. Thus, the hand-held terminal 5 has some of the various types of functions (e.g., input function, output (display) function, information processing function, network communication function, telephone call function, camera function, etc.) included in a general multifunctional device. The network communication function is a communication function realized through the Internet and/or a communication function realized through a mobile communication network. The hand-held terminal 5 may be attained by installing predetermined functions on an off-the-shelf multifunctional device. In the present embodiment, the hand-held terminal 5 is used for, in addition to being used as the multifunctional device described above, calculating the health information described above or executing the game process described above. Furthermore, the hand-held terminal 5 may be an information processing device that can be worn by the user such as, for example, a wrist watch-type or goggle-type terminal (i.e., a wearable terminal).

As shown in FIG. 2, the hand-held terminal 5 includes a communication section 10. The communication section 10 connects to the network 4 to perform communication with the server 3. In the present embodiment, the communication section 10 is a communication module having the function of connecting to a mobile communication network (in other words, mobile phone communication network) to perform communication. For example, the communication section 10 performs communication with a communication method in compliance with telecommunications standards of 3G or telecommunications standards of 4G (including LTE (Long Term Evolution)). It should be noted that there is no particular limitation on the method with which the hand-held terminal 5 communicates with the server 3, e.g., a method with which a communication module with Wi-Fi authentication performs communication through a wireless LAN. In addition, the hand-held terminal 5 may have a function of communicating with the server 3 through the mobile communication network and a function of performing communication with the server 3 through the wireless LAN.

The hand-held terminal 5 includes a processing section 11. The processing section 11 executes various types of information processing to be executed by the hand-held terminal 5. The processing section 11 is connected to the various sections 10, and 12 to 19 of the hand-held terminal 5. The processing section 11 has a CPU (Central Processing Unit) and a memory. In the hand-held terminal 5, the various types of information processing described above are executed as a result of the CPU using the memory and executing an information processing program stored in the hand-held terminal 5. In the present embodiment, the processing section 11 executes, as the information process, a process for calculating the health information described above, a game process, and a process for presenting the user with the information (e.g., the service information) received from the server 3, etc. When the hand-held terminal 5 operates as a multifunctional device, the processing section 11 executes information processes for achieving various functions.

The hand-held terminal 5 includes an input/output interface, and functions as an information processing device (in other words, input/output terminal) for allowing the user to input and browse information. Specifically, the hand-held terminal 5 includes an operation input section 12, a display 17, and a speaker 18. The operation input section 12 is an input device of any type for accepting an operation input by the user. In the present embodiment, the operation input section 12 includes buttons and a touch panel provided on the display 17. In other embodiments, the hand-held terminal 5 may include, as the operation input section 12, a sensor (acceleration sensor, gyro sensor) for sensing the operation of moving the hand-held terminal 5.

The display 17, which is one example of the output device, displays various types of images (e.g., game image, etc.) generated on the hand-held terminal 5 in response to an input on the operation input section 12, and displays various types of images (e.g., images relating to the network service) based on data received from the server 3. The speaker 18, which is one example of the output device, outputs various types of sounds (e.g., game sounds, etc.) generated by the hand-held terminal 5 in response to an input on the operation input section 12, and outputs various types of sounds (e.g., music and audio relating to the network service) based on the data received from the server 3.

The hand-held terminal 5 includes a sensor for sensing information for calculating the health information. In the present embodiment, the hand-held terminal 5 includes a location sensing section 13 and an environment sensor 14.

The location sensing section 13 senses the location of the hand-held terminal 5. In the present embodiment, the location sensing section 13 senses the location by using the GNSS (Global Navigation Satellite System). The location sensing section 13 is, for example, a GPS (Global Positioning System) sensor (e.g., GPS module). It should be noted that there is no particular limitation on the location sensing method by the location sensing section 13, and the location sensing section 13 may sense the location by using, for example, a beacon. Furthermore, for example, the location sensing section 13 may calculate information (e.g., information indicating at which floor of the building one is located) indicating the altitude of the user by calculating the change in altitude based on a sensing result from an atmospheric pressure sensor.

The environment sensor 14 senses the environment surrounding the hand-held terminal 5. In the present embodiment, the environment sensor 14 includes a temperature sensor and a humidity sensor. In other embodiments, an atmospheric pressure sensor, a luminous intensity sensor, a noise sensor, a smell sensor, or the like may be included in the environment sensor 14. More specifically, the environment sensor 14 may be one that senses at least one of temperature, humidity, illumination intensity, atmospheric pressure, sound, and smell. Furthermore, in another embodiment, the microphone 15 may be used as an environment sensor for sensing noise in the surrounding area.

The hand-held terminal 5 also includes the microphone 15. The microphone 15 senses sound in the surrounding area of the hand-held terminal 5. The microphone 15 may be used for calculating the health information. For example, the hand-held terminal 5 may sense the sound of snoring of the user by means of the microphone 15, and calculate sleep-related information based on the sensing result. The microphone 15 may be used for accepting an audio input on the hand-held terminal 5.

The hand-held terminal 5 includes a camera 16. The camera 16 is, for example, disposed on the same side (e.g., inner side) where the display 17 is disposed on the hand-held terminal 5 (see FIG. 3). Thus, the camera 16 is disposed at a position enabling capturing an image of the user who is operating the hand-held terminal 5. Note that the hand-held terminal 5 may determine the facial expression of the user based on the image captured by the camera 16 to calculate the fatigue level based on the facial expression of the user.

The hand-held terminal 5 includes a connector 19 for forming an electrical connection with the base device 6. In the present embodiment, when the hand-held terminal 5 is mounted on the base device 6 (see FIG. 3), the connector 19 makes contact with a connector 21 of the base device 6. With this, communication between the hand-held terminal 5 and the base device 6 becomes possible.

It should be noted that the hand-held terminal 5 includes a battery that is not diagrammatically represented, and each section of the hand-held terminal 5 operates by the power supplied from the battery. Although details will be described later, in the present embodiment, the battery of the hand-held terminal 5 can be charged by the base device 6.

Next, the configuration of the base device 6 in the present embodiment will be described. In the present embodiment, the base device 6 is disposed, for example, at the bedroom of the user, and is used for sensing biological information relating to sleep of the user while the user is in bed. Here, the biological information is information sensed from the body of the user. In the present embodiment, breathing, pulse, and body movements are sensed as the biological information. Note that in other embodiments, any information may be sensed as biological information, and any one or two of breathing, pulse and body movements may be sensed, or information other than these three information may be sensed. In addition, the base device 6 is used for presenting the user in bed with a content item (e.g., a content item that induces the user to fall asleep) and information (e.g., information of evaluation results relating to sleep).

The base device 6 includes a support section for detachably/reattachably supporting the hand-held terminal 5. Specifically, as shown in FIG. 3, a recessed portion in accordance with the shape of one portion of the hand-held terminal 5 is formed on a casing (specifically, support section) of the base device 6. When the hand-held terminal 5 is inserted in this recessed portion, the hand-held terminal 5 becomes mounted on the base device 6. Note that any mechanism may be used, with which the hand-held terminal 5 is supported on the base device 6.

As shown in FIG. 2, the base device 6 includes the connector 21. When the hand-held terminal 5 is inserted in the recessed portion, the connector 19 of the hand-held terminal 5 and a connector 21 of the base device 6 are connected. As a result, communication between the hand-held terminal 5 and the base device 6 becomes possible, and charging of the hand-held terminal 5 by the base device 6 becomes possible.

The base device 6 includes a Doppler sensor 24 which is one example of the sensor for sensing the biological information. The Doppler sensor 24, by discharging microwaves and receiving reflected waves of the discharged microwaves, senses a moving object based on a difference between the frequency of the discharged microwaves and the frequency of the received microwaves. In the present embodiment, the Doppler sensor 24 (more specifically, an emission section 24a) emits radio waves in the forward direction of the base device 6 (see FIG. 3). In the present embodiment, the subject to be sensed by the Doppler sensor 24 is the user, and body movements of the user are sensed by the Doppler sensor 24. Although details will be described later, analysis such as frequency analysis performed on the sensed biological information (in other words, output waveforms of the Doppler sensor 24) allows further calculation of biological information other than body movements such as breathing and pulse.

The base device 6 includes a power obtaining section 23 for obtaining power from an external power supply. In the present embodiment, the base device 6 is (may be detachably/reattachably) connected to a power plug and an AC adapter via a power cord that is not diagrammatically represented. When the power plug is connected to an electrical outlet which is an external power supply, power is supplied to the power obtaining section 23 of the base device 6. The base device 6 operates by the power from the external power supply obtained by the power obtaining section 23. In addition, the power obtaining section 23 performs charging of the hand-held terminal 5 by transmitting the supplied power to the hand-held terminal 5 through the connector 21. In other embodiments, the base device 6 may include a battery, and power charged in the battery may be transmitted to the hand-held terminal 5. Furthermore, in the present embodiment, although charging is performed in a mode in which power is supplied through the connector, in other embodiments, power may be supplied through non-contact charging.

The base device 6 includes a projector 25 for projecting an image on a screen or a wall surface (including the ceiling). The projector 25 may be any display device that displays an image on a surface (may be uneven) away from the base device 6 by projecting the image on the surface. In the present embodiment, as shown in FIG. 3, a projector 25 is formed on the base device 6 such that a light projection section (specifically, lens) 25a faces upward, i.e., such that the image is projected upward. More specifically, in the present embodiment, the projector 25 projects the image on the ceiling. In the present embodiment, for example, the projector 25 may display an image that induces the user to fall asleep or wake up (e.g., a sleep-inducing content item to be described later, etc.), and displays an image showing an evaluation result of sleep when the user awakens in the morning.

In the present embodiment, the base device 6 corrects the image to be projected on the ceiling by using, if necessary, a technology of so-called projection mapping. More specifically, the base device 6 corrects the image such that an image in accordance with the unevenness and/or the color of the projection plane (i.e., the ceiling) of the projector 25 is displayed. Note that conventional methods may be used as the method for correcting the image. The base device 6 includes a camera 27 for correcting the image. As shown in FIG. 3, the camera 27 is formed on the base device 6 in a direction that includes an image capturing range of the location where the image is to be projected by the projector 25. Thus, the camera 27 is provided so as to face the same direction (i.e., upward) as the projector 25.

The base device 6 includes a speaker 26. The speaker 26 is used for, for example, outputting a sound that induces the user to fall asleep or wake up (e.g., a sleep-inducing content item, etc., to be described later).

The base device 6 includes a control section 22 that controls the various sections 23 to 27 of the base device 6. The control section 22 is connected to each of the sections 21 and 23 to 27 of the base device 6. The control section 22 executes various types of control processes executed by the base device 6. The control section 22 has a memory and a CPU. In the base device 6, the various types of control processes are executed when the CPU uses the memory and executes information processing programs stored in the base device 6. For example, a control section 22 controls charging operation of the hand-held terminal 5 by controlling the power obtaining section 23. In addition, the control section 22 causes the projector 25 and/or the speaker 26 to reproduce information and a content item to be presented to the user on the base device. Furthermore, the control section 22 transmits information sensed by the Doppler sensor 24 to the hand-held terminal 5.

It should be noted that the base device 6 may include other elements in addition to or instead of those shown in FIG. 2. For example, the base device 6 may include an environment sensor, a display, a nondirectional speaker, a light source (e.g., illumination), and/or a smell generation device, etc. Note that when the base device 6 includes an environment sensor, the hand-held terminal 5 may not include an environment sensor. The hand-held terminal 5 and the base device 6 may include environment sensors of the same type (i.e., environment sensors that sense the same information) or may include environment sensors of different types.

Next, the configuration of the server 3 will be described. The server 3 includes one or more information processing devices (i.e., server devices) each having a CPU and a memory. With the server 3, the CPU executes an information processing program stored in the server 3 using the memory, thereby executing various information processes. For example, the server 3 executes the process of storing information received from the hand-held terminal 5 in a predetermined storage section, the process of presenting the hand-held terminal 5 with a network service in accordance with the information, etc.

Note that a "server" as used herein refers to a single information processing device (i.e., a server device) and also to a whole server device group (i.e., a server system) when the server is formed of multiple server devices. In the present embodiment, although the server 3 will be described as an integral configuration, the server 3 may have a configuration including multiple server devices divided in accordance with function and/or role. For example, the server 3 may have a configuration including a data server that accumulates the health information obtained from the hand-held terminal 5 and a service server that provides a network service based on the health information. Furthermore, when the server 3 performs a service of providing a product or the like ("product or the like" means to include services as well as products; this similarly applies hereinbelow) as a part of the network service, the server 3 may have a configuration including a shop server for billing and providing the product or the like.

2. Outline of Operation of Information Processing System

Next, the outline of the operation of the information processing system 1 will be described. In the present embodiment, the terminal system 2 calculates the health information while the user is asleep (referred to as the sleep period). First, the operation of the terminal system 2 during the sleep period will be described below.

(2-1: Operation of Terminal System During Sleep Period)

Figure 4:
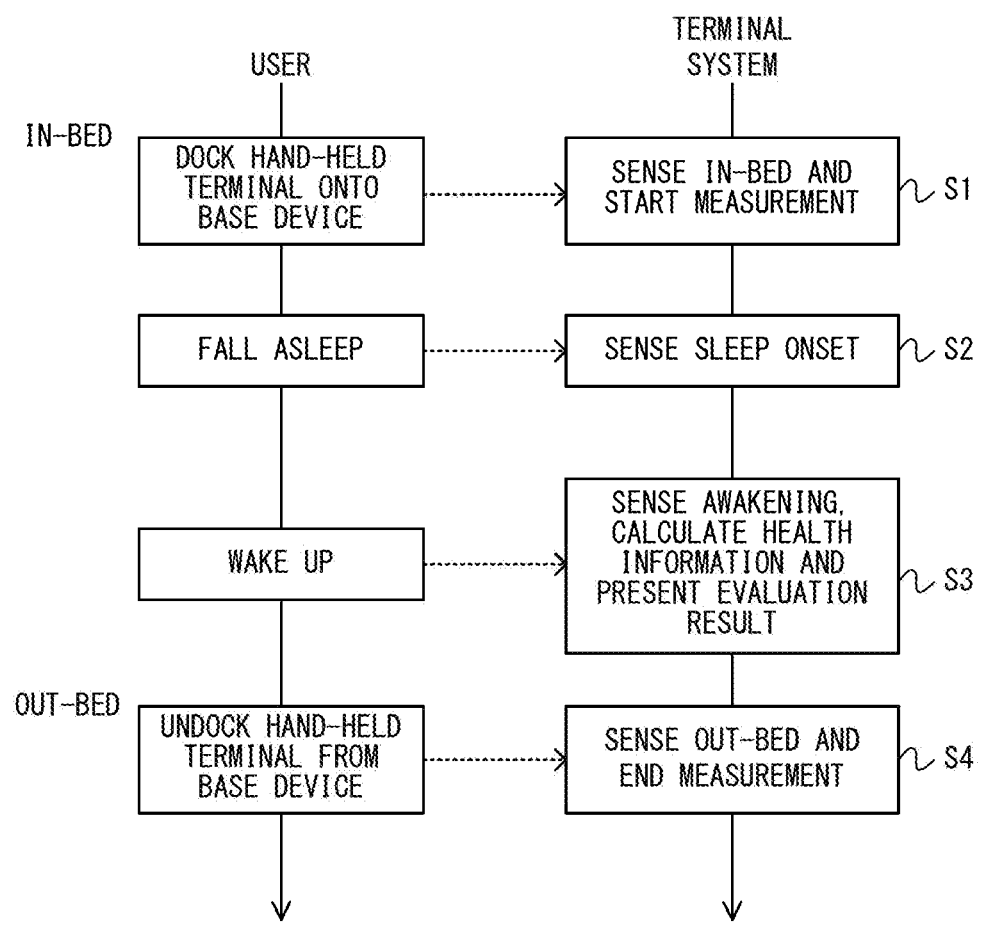
FIG. 4 shows an example flow of an operation of a terminal system during a sleep period.

FIG. 4 shows an example flow of the operation of the terminal system during the sleep period. In the present embodiment, the base device 6 is placed in the bedroom of the user, and is more specifically placed around the user (e.g., bedside). The user docks the hand-held terminal 5 onto the base device 6 when getting in bed. As the hand-held terminal 5 is docked onto the base device 6, the terminal system 2 determines that the user has gotten in bed (i.e., senses the user getting in bed) (step S1). In response to sensing the user getting in bed, the terminal system 2 starts the measurement for calculating the user health information. In the present embodiment, information relating to the sleep of the user is calculated as the health information based on the sensing result of the Doppler sensor 24 of the base device 6, the details of which will be described later. Information sensed by the environment sensor 14, as well as the Doppler sensor 24, is also obtained as a measurement result.

Note that in the present embodiment, the base device 6 has the function of charging the hand-held terminal 5. It is possible that the user docks the hand-held terminal 5 onto the base device 6 when getting in bed for the purpose of charging the hand-held terminal 5. That is, according to the present embodiment, since the user is motivated to dock the hand-held terminal 5 onto the base device 6, it is possible to reduce the possibility that the user forgets to dock the hand-held terminal 5 onto the base device 6.

After getting in bed, when the user falls asleep (in other words, enters the sleep state), the terminal system 2 senses the user having fallen asleep based on the measurement result (step S2). Even after sensing the user falling asleep, the terminal system 2 continues the measurement to determine the user's state during sleep based on the measurement result. The operation of the hand-held terminal 5 and/or the base device 6 may be controlled based on the user's state.

When the user awakens out of sleep, the terminal system 2 senses the awakening of the user based on the measurement result (step S3). When the awakening of the user is sensed, the terminal system 2 calculates the health information based on the measurement result obtained during sleep. Moreover, the terminal system 2 evaluates the calculated health information, and presents the evaluation result to the user. In the present embodiment, the evaluation result of the health information is presented as a game element (e.g., as the number of lives remaining of the player object) in a game app, the details of which will be described later.

When awakening, the user checks the evaluation result, and then gets out of bed. When getting out of bed, the user takes the hand-held terminal 5 off the base device 6. The terminal system 2 determines that the user has gotten out of bed (i.e., senses the user getting out of bed) in response to the hand-held terminal 5 being taken off the base device 6 (step S4). Note that the user getting out of bed may be sensed based on the measurement result described above, instead of (or in addition to) sensing it based on the docking state between the hand-held terminal 5 and the base device 6. For example, the terminal system 2 may determine that the user has getting out of bed in response to the user being no longer present within the sensing range of the Doppler sensor.

When the health information is calculated after the awakening of the user, the terminal system 2 stops the measurement for calculating the health information. Note that in other embodiments, the measurement may be stopped in response to sensing the user getting out of bed.

As described above, in the present embodiment, when measuring the health information, the user can simply dock the hand-held terminal 5 onto the base device 6 when getting in bed and take the hand-held terminal 5 off the base device 6 when getting out of bed. Thus, in the present embodiment, the user can measure the health information with little trouble by using the terminal system 2.

(2-2: Method for Calculating Health Information)

A method for calculating the health information according to the present embodiment will now be described. In the present embodiment, the terminal system 2 calculates, as the health information, sleep-related information and fatigue-related information. More specifically, the terminal system 2 calculates sleep indices and a fatigue index based on the sensing result of the Doppler sensor 24. Sleep indices are indices relating to the user's sleep, and are indices each representing a sleep-related state or a sleep result, for example. More specifically, the sleep indices are numerical values representing sleep time, sleep latency, WASO (Wake Time After Sleep Onset) (in other words, the amount of time of mid-sleep awakenings) and sleep efficiency, etc. The fatigue index is an index relating to the fatigue of the user, representing the fatigue level or the fatigue state (e.g., the fatigue type, etc.) of the user, for example. In the present embodiment, the fatigue index is calculated taking sleep indices into consideration, and is calculated as a numerical value representing the fatigue level of the user. A method for calculating the health information of the present embodiment will now be described with reference to FIG. 5.

Figure 5:
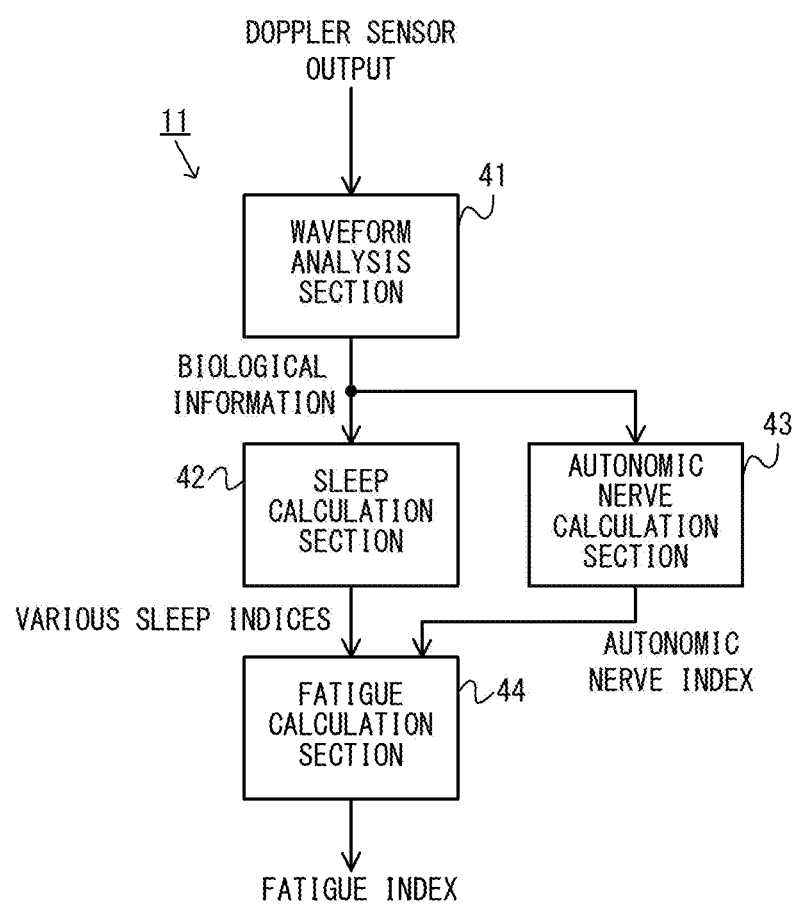
FIG. 5 is a functional block diagram showing an example functional configuration for calculating health information at a processing section of a hand-held terminal.

FIG. 5 is a functional block diagram showing an example functional configuration for calculating health information at the processing section 11 of the hand-held terminal 5. As shown in FIG. 5, the processing section 11 includes a waveform analysis section 41, a sleep calculation section 42, an autonomic nerve calculation section 43, and a fatigue calculation section 44. Note that although the elements for calculating the health information (the various sections 41 to 44 shown in FIG. 5) is provided in the hand-held terminal 5 in the present embodiment, some or all of the elements may be provided in the base device 6 in other embodiments.

The waveform analysis section 41 calculates breathing, pulse, and body movements as additional biological information on the basis of the biological information (i.e., output waveforms) sensed by the Doppler sensor 24. Conventionally, obtaining waveforms representing breathing, pulse, and body movements has been known to be possible by separating output waveforms of the Doppler sensor 24 by the frequency. The waveform analysis section 41 separates the output waveforms through a frequency analysis, or the like, into a frequency bandwidth corresponding to breathing, a frequency bandwidth corresponding to pulse, and a frequency bandwidth corresponding to body movements, and outputs the separated waveform data. As shown in FIG. 5, an output from the waveform analysis section 41 is input to both the sleep calculation section 42 and the autonomic nerve calculation section 43.

The sleep calculation section 42 calculates various sleep indices on the basis of the biological information (breathing, pulse, and body movements in the present embodiment). Conventionally, methods for calculating the sleep indices on the basis of breathing, pulse, and body movements are known. In the present embodiment, the sleep calculation section 42 calculates sleep indices representing the following information.

amount of time from in-bed to sleep onset (i.e., sleep latency)
amount of time from awakening to out-bed
WASO
number of mid-sleep awakenings
timing of mid-sleep awakenings
sleep efficiency
total sleep time
activity level during sleep
sleep stage
REM sleep time
non-REM sleep time
REM sleep cycle
ratio between REM sleep time and non-REM sleep time
sleep quality
ratio of amount of time of deep sleep with respect to predetermined period of time since sleep onset
ratio of amount of time of light sleep with respect to predetermined period of time until awakening
difference between ideal sleep onset timing and actual sleep onset timing
difference between ideal awakening timing and actual awakening timing Note that the "ideal sleep onset timing" and the "ideal awakening timing" are calculated based on past sleep indices of the user, for example.

In other embodiments, only some of the sleep indices described above may be calculated, or different sleep indices from those described above may be calculated. For example, the number of times of tossing and turning may be calculated as a sleep index. The number of times of tossing and turning can be calculated (or estimated) based on the body movements sensed by the Doppler sensor 24.

Sleep indices may be calculated based on outputs from sensors other than the Doppler sensor 24. For example, an index representing the level of snoring and/or an index representing the environment during sleep may be calculated as sleep indices. The level of snoring may be calculated based on the sound sensed by the microphone 15, for example. For example, the temperature, the humidity, the luminous intensity, the atmospheric pressure, and the like, may be calculated based on the output of the environment sensor 14, as indices representing the environment during sleep. The sleep indices may be calculated based on the sensing result of the camera 16. For example, biological information such as pulse and/or body movements can be calculated based on the image of the user captured by the camera 16. Thus, the sleep calculation section 42 may calculate the sleep indices (and the fatigue index) using biological information obtained from the image captured by the camera 16 in addition to (or instead of) using the biological information obtained from the sensing result of the Doppler sensor 24.

The autonomic nerve calculation section 43 calculates an index (referred to as the autonomic nerve index) indicating the action level of the autonomic nerves (specifically, the sympathetic nerves and the parasympathetic nerves) on the basis of the biological information. Specifically, the waveform of pulse (specifically, the RR interval) included in the biological information is frequency-analyzed by using maximum entropy method and Fourier transformation to calculate a high frequency component (approximately 0.15 to 0.40 [Hz]) HF and a low frequency component (approximately 0.04 to 0.15 [Hz]) LF of the waveform. The high frequency component HF is known to indicate the action level of parasympathetic nerves and the low frequency component LF is known to indicate the action level of sympathetic nerves. In addition, it is known that the fatigue level can be evaluated from a ratio between the action level of parasympathetic nerves and the action level of sympathetic nerves (e.g., see Japanese Laid-Open Patent Publication No. 2010-201113). Thus, the autonomic nerve calculation section 43 calculates a ratio (LF/HF) between the high frequency component HF and the low frequency component LF as the autonomic nerve index. As shown in FIG. 5, an output from the autonomic nerve calculation section 43 is used as an input for the fatigue calculation section 44.

The fatigue calculation section 44 calculates the fatigue level based on the sleep indices and the autonomic nerve index. In the present embodiment, as the fatigue index, a fatigue level indicating the fatigue level with a numerical value from 0 to 100 is calculated. Although any method can be used for calculating the fatigue index, the following methods may be used, for example.

A first method is a method of calculating the fatigue level from the sleep indices. Here, the sleep indices are thought to correlate with the fatigue level. For example, the following are examples in which the fatigue level is speculated to be high.

long sleep latency
long WASO
high number of mid-sleep awakenings
poor sleep efficiency
short total sleep time
imbalance between REM sleep time and non-REM sleep time (e.g., ratio between REM sleep time and non-REM sleep time being out of normal range)

Thus, the fatigue calculation section 44 calculates the fatigue level such that the fatigue level becomes high when the sleep indices fit the examples described above and such that the fatigue level becomes low when the sleep indices do not fit the examples described above. For example, the fatigue calculation section 44 may determine whether or not the criteria described above are met to calculate a score in accordance with the number of criteria met, and calculate the fatigue level in accordance with the total score. In this process, the fatigue calculation section 44 may calculate the score while the criteria are weighted. Furthermore, a reference value (e.g., "six hours" for the total sleep time) may be set for each criterion, and the score may be calculated such that the score is higher as the value of a calculated sleep index deviates more from the reference value.

As described above, in the present embodiment, the sleep indices relating to sleep of the user is calculated on the basis of the biological information, and the fatigue level is calculated on the basis of the sleep indices. Since a correlation is thought to exist between the sleep indices and the fatigue level as described above, the accuracy of the fatigue level can be improved by calculating the fatigue level on the basis of the sleep indices.

A second method is a method of calculating the fatigue level on the basis of the autonomic nerve index. As described above, it is known that the fatigue level can be evaluated by using the balance between the action level of sympathetic nerves and that of parasympathetic nerves, i.e., the autonomic nerve index. Thus, for example, the fatigue calculation section 44 calculates the fatigue level such that the fatigue level is higher as the value of the autonomic nerve index deviates more from the reference value.

In the present embodiment, the fatigue calculation section 44 calculates the fatigue level by using the first and second methods. Specifically, the fatigue calculation section 44 calculates respective fatigue levels using the two methods, and calculates the final fatigue level on the basis of the respective calculated fatigue levels. The fatigue calculation section 44 may, for example, use an average of the two fatigue levels as the final fatigue level, or may calculate the final fatigue level while weighting one of the two fatigue levels.

In other embodiments, the fatigue level may be calculated by using the following method, in addition to the two methods described above. That is, a method of calculating the fatigue level on the basis of the sleep time within a predetermined period of time (e.g., one week) may be used. Conventionally, there is a technique of calculating the fatigue level on the basis of sleep time and work hours in a Fatigue Risk Management System (FRMS). In the technique, for example, by setting the work hours as a constant for simplification, the fatigue level can be calculated on the basis of sleep time (alone).

Note that any method may be used for calculating the fatigue index, and the fatigue index may be of any content. In other embodiments, as the fatigue index, a value indicating the fatigue level for each type of fatigue may be calculated. For example, in other embodiments, the fatigue index may include three different values, i.e., a value representing the level of acute fatigue, a value representing the level of cumulative fatigue, and a value representing the level of mental fatigue.

In the present embodiment, the fatigue calculation section 44 calculates the energy level based on the fatigue level calculated as described above. The energy level is a numerical value calculated for the purpose of presenting the user's health state (the state of sleep and the fatigue level in the present embodiment) in an easy-to-understand manner for the user, and a higher energy level represents a better state (in other words, a lower fatigue level). The energy level may be calculated by any method, and the energy level may be calculated by, for example, subtracting the fatigue level from 100.

In the present embodiment, the energy level is presented to the user as the evaluation result of the health information. Note that in other embodiments, as the evaluation result, the fatigue level described above may be presented to the user, or a sleep quality level (a numerical value representing how good the sleep is) calculated from the sleep indices may be presented to the user. The energy level, the fatigue level and the sleep quality level can be said to be the health information or the evaluation result of the health information. That is, the health information may be a second type of health information representing the evaluation result of a first type of health information (e.g., the sleep indices).

As described above, in the present embodiment, the terminal system 2 calculates, as the health information, the sleep indices, the fatigue index (i.e., the fatigue level) and the energy level. Some or all of these health information are transmitted from the terminal system 2 to the server 3, and the server 3 stores the health information for each user. The hand-held terminal 5 stores the calculated health information in its storage section.

(2-3: Game Process)

Next, a game process to be executed on the terminal system 2 (specifically, the hand-held terminal 5) will be described. As described above, in the present embodiment, the user can measure the health information in a simple operation. However, the measurement of the health information will be less meaningful and will not lead to improvements to the health of the user, unless the user checks the evaluation result, etc. (which may be advice information or recommendation information based on the evaluation result) of the health information measured. For example, a user who is not very much interested in health will not feel entertained and his/her interest in the evaluation result, etc., may gradually fade away if the evaluation result is simply presented to the user. As a result, the user may stop checking the evaluation result, etc., or may skip the measurement itself.

In view of this, in the present embodiment, the terminal system 2 executes a game process in order to motivate the user for actions such as measuring the health information and checking the evaluation result, etc. That is, the terminal system 2 executes a game process based on the evaluation result, and presents, to the user, a game result in accordance with the evaluation result. In the present embodiment, the game may progress in accordance with the evaluation result and may progress in accordance with the activity of the user relating to the measurement (e.g., awakening, out-bed, in-bed, etc.). Thus, in the present embodiment, the terminal system 2 allows the user to measure the health information as if by playing a video game. Then, it is possible to motivate the user to continuously perform the action described above, thereby improving the health-improving effect as the user continuously performs the action. An example game process of the present embodiment will now be described with reference to FIG. 6 to FIG. 14.

Figure 6:
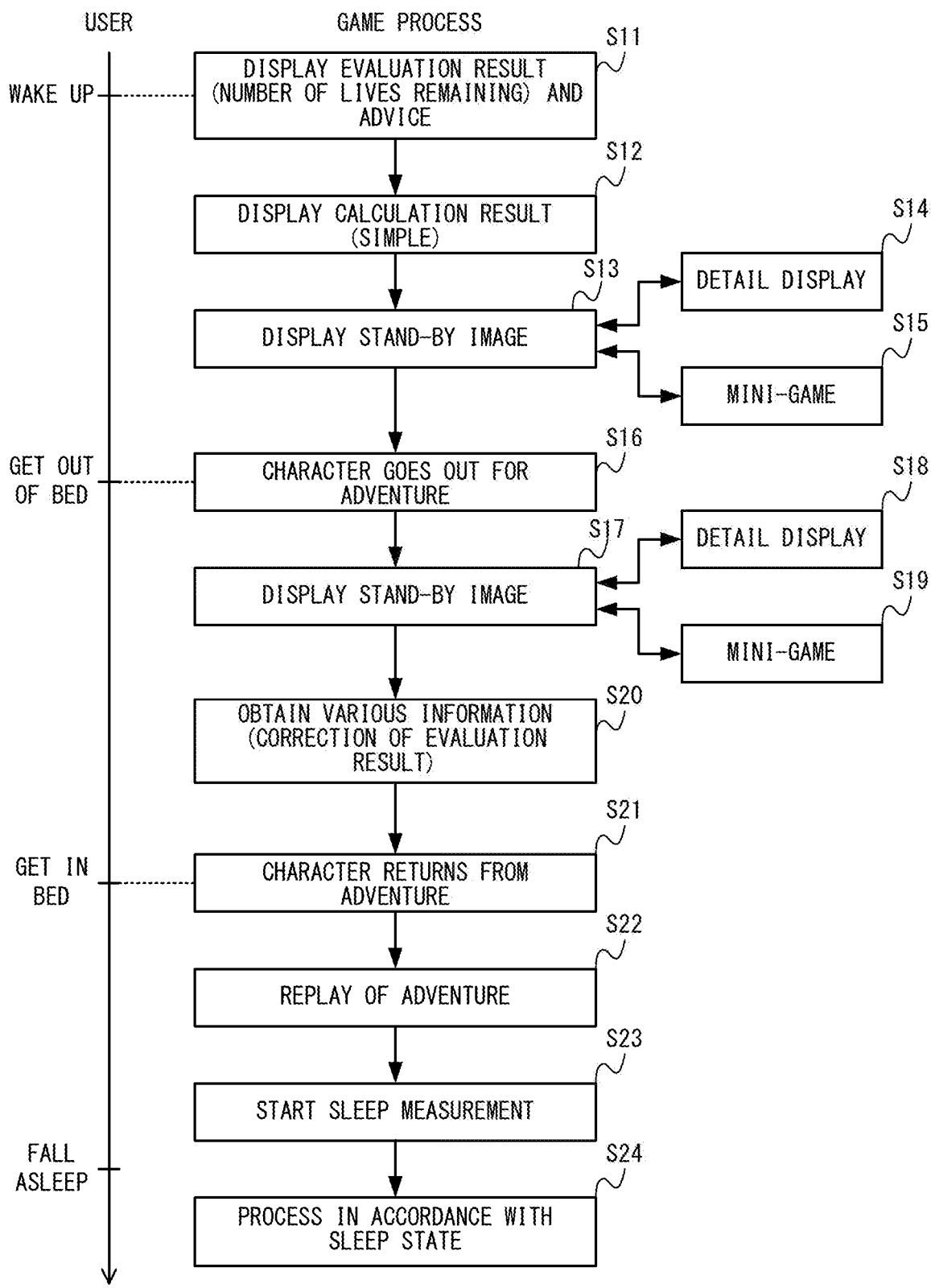
FIG. 6 shows an example flow of a game process in the present embodiment.

FIG. 6 shows an example flow of a game process according to the present embodiment. In the present embodiment, as described above, measurement is performed for calculating the user health information while the user is asleep, and the game process is executed primarily when the user is awake. FIG. 6 shows the flow of a game process to be executed from when the user awakens until the user falls asleep.

(Process when User Awakens)

Upon sensing the user awakening, the hand-held terminal 5 displays the evaluation result of the health information and advice based on the evaluation result (step S11). As the evaluation result of the health information is calculated in response to the user awakening, as described above, the hand-held terminal 5 displays information representing the calculated evaluation result on the display 17. The hand-held terminal 5 also displays information representing the advice generated based on the evaluation result on the display 17.

Figure 7:
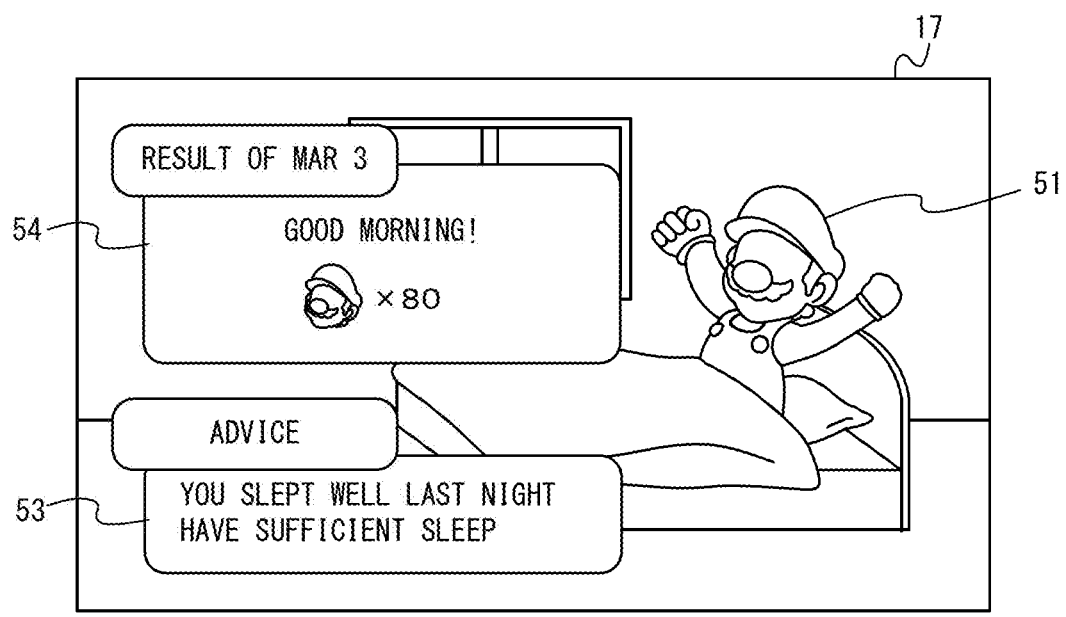
FIG. 7 shows an example game image (referred to as a wake-up game image) to be displayed on a hand-held terminal when the user wakes up.

FIG. 7 shows an example game image (referred to as a wake-up game image) to be displayed on the hand-held terminal when the user awakens. The wake-up game image shown in FIG. 7 includes a player object 51, evaluation result information 52 and advice information 53.

The player object 51 is a game character that acts in accordance with an input by the user (referred to also as the player) (the health information is used as the input in the present embodiment). As shown in FIG. 7, when the user awakens, an image is displayed on the display 17 depicting the player object 51 waking up.

The evaluation result information 52 represents the evaluation result of the health information calculated based on the biological information measured during a sleep period. As described above, in the present embodiment, the energy level (in other words, a numerical value representing the energy level) is calculated as the evaluation result. Here, in the present embodiment, the evaluation result is presented as a game element to the user. That is, as shown in FIG. 7, a numerical value representing the energy level ("80" in FIG. 7) is displayed as the number of lives remaining of the player object 51. Note that the evaluation result may be displayed as any game element. For example, in other embodiments, the evaluation result may be presented as the number or kind of items, the amount of money or a parameter (e.g., the power level) of the player object.

The advice information 53 represents advice for the user relating to the evaluation result of the health information. The advice information 53 is generated based on the health information. While the advice information 53 may be generated by any method, the hand-held terminal 5 may specify the content of advice by using a table stored in advance, the table associating health information-related conditions with different content of advice to be presented, for example. That is, when the health information satisfies any of the conditions included in the table, the hand-held terminal 5 generates and displays advice information representing the content of advice that is associated with the condition satisfied.

As described above, the wake-up game image is displayed in response to the user awakening. As described above, in the present embodiment, sleep indices calculated based on the sensing result of the Doppler sensor 24 are used to determine whether the user has awakened. Note that when the hand-held terminal 5 has the alarm function, it may be determined that the user has awakened in response to the user stopping the alarm function. That is, at the preset alarm time, the hand-held terminal 5 may give a notification prompting the user to awaken using a sound and/or light. Then, the hand-held terminal 5 may determine that the user has awakened in response to the user performing an operation of stopping the notification. Note that the alarm time may be manually set by the user or may be set based on the sleep indices described above. In other embodiments, the hand-held terminal 5 may display the wake-up game image at the alarm time, instead of when the user awakens.

The wake-up game image is displayed for a predetermined amount of time. Then, the hand-held terminal 5 produces a simplified display showing the calculated health information (step S12). That is, the hand-held terminal 5 displays a part of the health information calculated based on the biological information measured during the sleep period. Note that the switching from the wake-up game image of step S11 and the image of step S12 (i.e., the simplified display image to be described later) may be done automatically by the hand-held terminal 5 in response to the satisfaction of a predetermined condition as described above, or may be done in response to an instruction from the user. For example, the hand-held terminal 5 may display the simplified display image in response to the user performing a predetermined operation while the wake-up game image is displayed.

Figure 8:
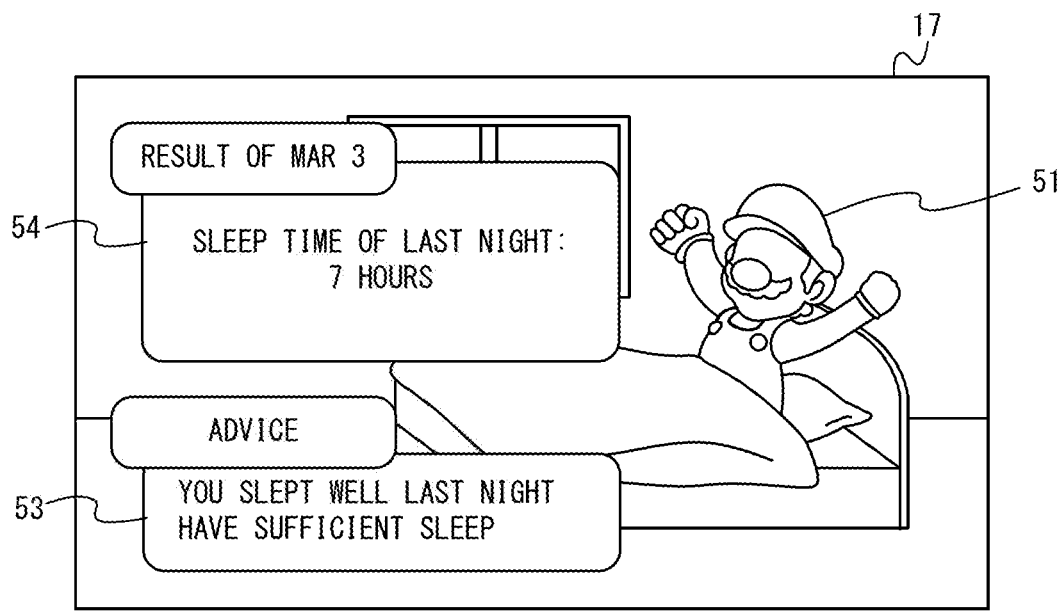
FIG. 8 shows an example game image (referred to as a simplified display image) to be displayed when producing a simplified display of health information.

FIG. 8 shows an example game image (referred to as a simplified display image) to be displayed when producing a simplified display of health information. Simplified information 54 is displayed in the simplified display image shown in FIG. 8. The player object 51 and the advice information 53 are displayed even in the simplified display image, as in the wake-up game image (see FIG. 7).

The simplified information 54 shows a part of the calculated health information. In the present embodiment, the simplified information 54 contains the sleep time, which is an example sleep index. Note that any content may be represented by the simplified information 54. Note however that since the simplified information 54 is presented immediately after the user wakes up, the simplified information 54 contains information that can easily be understood by the user in the present embodiment. That is, as a specific sleep-related index, i.e., the sleep time, is presented, the sleep measurement result is presented in an easy-to-understand manner for the user. Note that in other embodiments, the hand-held terminal 5 may display, as the simplified information 54, indices representing the sleep quality level and/or the sleep quality described above, instead of the sleep time (or in addition to the sleep time).

As described above, in the present embodiment, in response to sensing the user awakening, a part of the calculated health information is presented as a game element to the user (step S11) and another part of the health information (which may be the same information in other embodiments) is presented to the user as an index representing the health (as a sleep index in the present embodiment) (step S12). Thus, by giving a video game-like nature to the presentation of the health information, it is possible to keep the user interested, and present the health information (i.e., the sleep indices) in an easy-to-understand manner for the user. Moreover, in the present embodiment, information representing the evaluation result of the health information is presented as a game element to the user, and at least a part of the health information from which the evaluation result derives (i.e., which is used in the calculation of the evaluation result) is presented to the user as an index representing the health. Therefore, it is possible to present the evaluation result in such a manner that keeps the user interested, and also to present detailed information from which the evaluation result derives in an easy-to-understand manner for the user. Note that the evaluation result as a game element and the health information as a health index may be presented at the same time, or may be presented at different points in time (as in the present embodiment).

Note that although the advice information 53 included in the simplified display image is the same as the advice information 53 included in the wake-up game image in the present embodiment, these two images may include advice information of different content in other embodiments.

The simplified display is produced only for a predetermined amount of time. Then, the hand-held terminal 5 displays a stand-by image (in other words, a menu image) (step S13). That is, the hand-held terminal 5 displays a stand-by image including a menu image on the display 17. Note that the switching from the simplified display image of step S12 to the stand-by image of step S13 may be done automatically by the hand-held terminal 5 in response to the satisfaction of a predetermined condition as described above, or may be done in response to an instruction from the user. In other embodiments, the stand-by image may be displayed after the wake-up game image (without displaying the simplified display image). The hand-held terminal 5 may switch between the wake-up game image, the simplified display image and the stand-by image in response to an instruction from the user.

Figure 9:
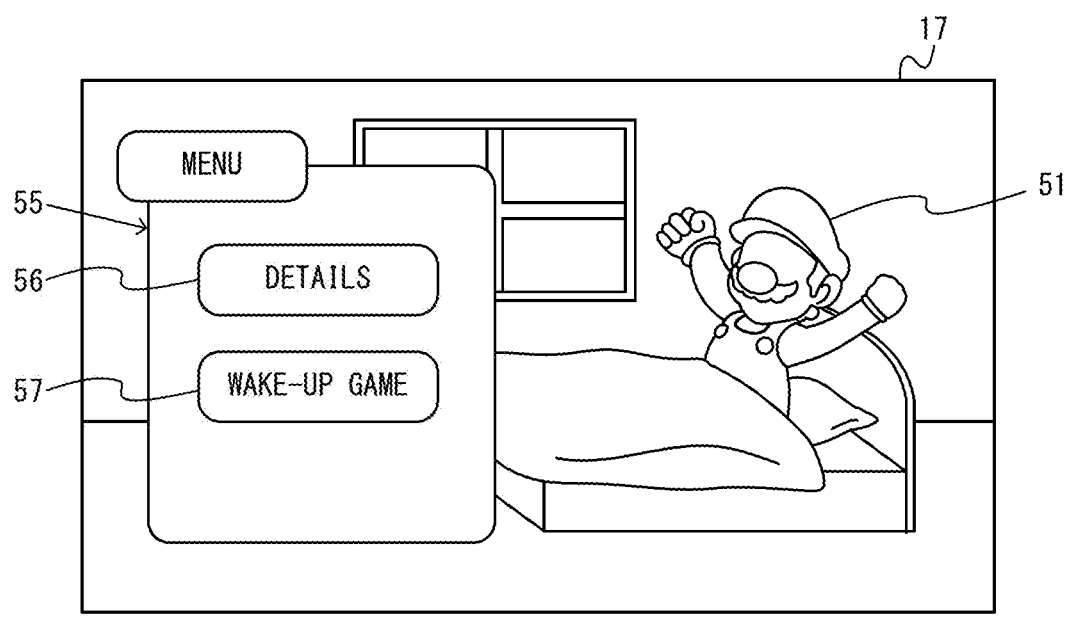
FIG. 9 shows an example stand-by image.

FIG. 9 shows an example stand-by image. A menu image 55 is displayed in the stand-by image shown in FIG. 9. The player object 51 is displayed also in the stand-by image, as in the wake-up game image (FIG. 7) and the simplified display image (FIG. 8).

The menu image 55 shows instructions that the user can give while the stand-by image is displayed. In the present embodiment, the menu image 55 includes a detail display button 56 and a mini-game button 57. The detail display button 56 is an image representing a button used for giving an instruction to display the details of the calculated health information. The mini-game button 57 is an image representing a button used for giving an instruction to start a mini-game (referred to also as a wake-up game). By making an input (e.g., a touch input) on these buttons, the user can cause the hand-held terminal 5 to produce a detail display of the health information and to execute the mini-game.

When an input is made on the detail display button 56 while the stand-by image is displayed (step S13), the hand-held terminal 5 produces a detail display of the health information (step S14). That is, the hand-held terminal 5 displays, on the display 17, a detail display image representing a more detailed display than the simplified display of the health information described above. In the present embodiment, an image to be described below is displayed, for example, as the detail display image.

Figure 10:
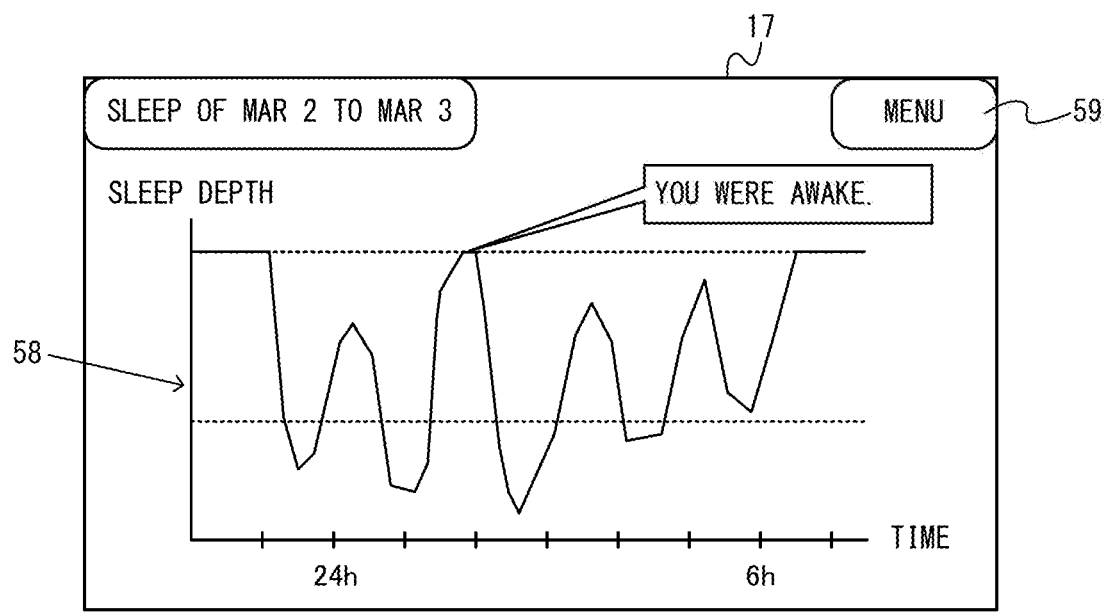
FIG. 10 shows an example detail display image.

FIG. 10 shows an example detail display image. The detail display image shown in FIG. 10 represents detailed information relating to the sleep last night. That is, the detail display image shown in FIG. 10 represents the details of the health information based on the biological information measured during the last sleep period (typically, the period from last night until the current morning). Specifically, FIG. 10 shows a graph 58 of which the horizontal axis represents time and the vertical axis represents the depth of sleep. From the graph 58, the user can know, in detail, how the depth of sleep changed during the last sleep period.

In addition to the graph 58 described above, the detail display image includes a description added to a characteristic portion of the graph 58. For example, as shown in FIG. 10, the graph 58 includes an image representing the description "you were awake" pointing to a portion of a mid-sleep awakening. Thus, the hand-held terminal 5 may detect a characteristic portion from the sleep period (referred to also as the measurement period) based on the sleep indices so as to add a description image to the detected characteristic portion. For example, a characteristic portion may be a portion of a mid-sleep awakening or a portion where light sleep continued over a predetermined amount of time or longer. The hand-held terminal 5 stores a table associating characteristic portions with descriptions, and displays a description image representing a description associated with a detected characteristic portion in such a manner that the description image is associated with the characteristic portion on the graph 58.

Note that in other embodiments, the description image may represent a description that takes into consideration the environment sensor information sensed by the environment sensor 14. Note that the environment sensor 14 senses temperature, humidity and/or ambient sound, for example, as the environment sensor information. For example, when the characteristic portion is detected, the hand-held terminal 5 may obtain the environment sensor information sensed at a point in time (or during a period) that corresponds to the characteristic portion so as to generate a description based on the environment sensor information. For example, the hand-held terminal 5 may obtain the temperature to generate and display a description such as "You were awake at around 2 am. This may be because of the low room temperature." For example, the hand-held terminal 5 may obtain the ambient sound to generate and display a description such as "You were awake at around 2 am. This may be because of a loud noise."

Figure 11:
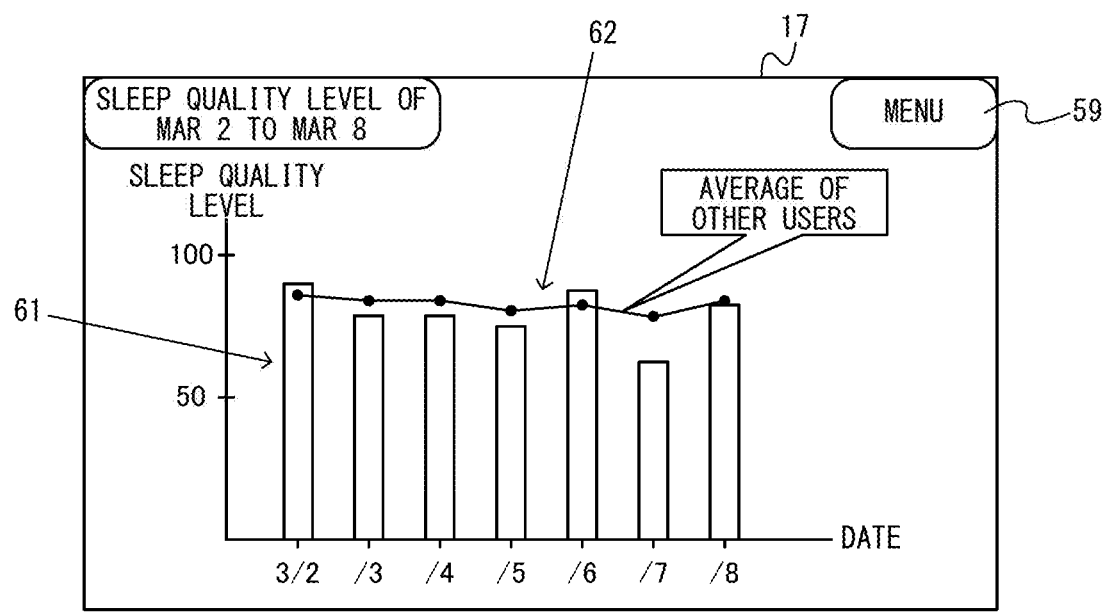
FIG. 11 shows another example detail display image.

FIG. 11 shows another example detail display image. The detail display image shown in FIG. 11 is an example image representing the detailed information relating to sleep for the past one week. FIG. 11 shows a bar graph 61 representing changes in the sleep quality level of the user for the past one week. The horizontal axis of the graph 61 represents the date, and the vertical axis thereof represents the sleep quality level. Note that the sleep quality level is an index representing how good the sleep is, and is calculated based on the sleep indices. The sleep quality level is a numerical value from 0 to 100, for example, and is calculated so that a higher value means a higher sleep quality (in other words, a better evaluation on the sleep quality). With the graph 61, the user can know, in detail, changes in the sleep quality level over a week.

The detail display image shown in FIG. 11 includes a graph 62 based on sleep quality levels of other users, in addition to the graph 61 of the sleep quality level of the user himself/herself. The graph 62 represents the average of the sleep quality levels of other users. With the graphs 61 and 62, the user can know not only changes in the sleep quality level of the user but also (the average of) the sleep quality levels of other users and the difference between the sleep quality level of the user and the sleep quality levels of other users.

Note that the sleep quality levels of other users are stored in the server 3. The server 3 also calculates and stores the average value (e.g., the average value for each day) of the sleep quality levels of other users stored therein. The hand-held terminal 5 receives from the server 3 average values of sleep quality levels for an intended period (the past one week in the example shown in FIG. 11) at any point in time to generate and display the graph 62 based on the received information. Note that the average value may be calculated for all the users registered on the network service or for those uses who satisfy predetermined criteria. The criteria may be those relating to personal information, such as region (e.g., nationality), age, sex and occupation, for example.

In the present embodiment, a detail display image as shown in FIG. 10 and FIG. 11 is displayed. The hand-held terminal 5 may display one of a plurality of types of detail display images that is specified by the user. The detail display image may be of any content that includes information not displayed in the simplified display (step S12) described above. For example, other than the detail display images shown in FIG. 10 and FIG. 11, the detail display image may include the average value of the sleep quality levels of the user for a predetermined period of time (e.g., one week or one month). For example, the detail display image may represent a comparison between the current sleep quality level of the user and the sleep quality levels of the user in the past. For example, a graph representing the sleep quality levels of the user in the past (e.g., the sleep quality levels of the user from one month ago) may be displayed, instead of the graph 62 shown in FIG. 11.

The detail display image may be an image representing information other than the sleep quality level, and it may for example represent sleep indices other than the sleep quality level, the fatigue index and/or the energy level. The hand-held terminal 5 may generate and display a detail display image relating to information, of the health information, specified by the user.

With the detail display image being displayed, the hand-held terminal 5 switches to the stand-by image in response to a predetermined end instruction by the user (step S13). The predetermined end instruction given by an input on a menu button 59 displayed on the detail display image (FIG. 10 and FIG. 11).

With the stand-by image being displayed (step S13), the hand-held terminal 5 starts a mini-game (step S15) when an input is made on the mini-game button 57. The mini-game is a game that is different from the game using health information (specifically, the energy level) as an input, and is a game in which the user performs a simple game operation, a calculation, etc. The mini-game may be of any content, and the mini-game may be a puzzle game, a quiz game, or a game in which the user performs a calculation, for example. Prompting the user to play such a mini-game is effective in awakening the user.

In the present embodiment, the hand-held terminal 5 corrects the energy level (specifically, the energy level calculated based on the biological information measured during the sleep period) based on the result of the mini-game. For example, the hand-held terminal 5 may decrease the energy level if the result of the mini-game is poor, assuming that the user has not woken up well, and may increase the energy level if the result of the mini-game is good, assuming that the user has woken up well. Thus, in the present embodiment, the energy level is calculated based on the result of the mini-game. Moreover, the result of the mini-game is reflected in the game process. The hand-held terminal 5 transmits information, representing the corrected energy level, to the server 3. The server 3 stores information representing the received corrected energy level.

In other embodiments, the hand-held terminal 5 may use the result of the mini-game as an input to the game process instead of (or in addition to) correcting the energy level based on the result of the mini-game. For example, the hand-held terminal 5 may award an item to the user (in other words, the player object) in accordance with the result of the mini-game, and execute the game process based on the energy level and the item or items awarded. As in the present embodiment, it is possible also in this manner to reflect the result of the mini-game in the game process.

The hand-held terminal 5 may ask a question to the user instead of executing the mini-game, or in addition to the execution of the mini-game (in other words, during the mini-game). That is, the hand-held terminal 5 asks the user a question relating to the sleep and/or fatigue state, and prompts the user to input an answer. For example, the hand-held terminal 5 asks questions, e.g., if the user is feeling fatigued, if the user has woken up well, if the user still has sleepiness, etc., prompting the user to give subjective answers. Then, the answer may be used as the mini-game result. Then, the terminal system 2 can obtain the user's subjective evaluation relating to sleep and/or fatigue, and can calculate the health information reflecting the subjective evaluation.

As described above, in the present embodiment, it is possible to awaken the user by having the user play a mini-game when the user awakens, and it is possible to calculate the health information reflecting the user's state after the user wakes up by calculating (more specifically, correcting) the health information based on the mini-game result.

Note that in other embodiments, the hand-held terminal 5 may determine whether or not to prompt the user to launch a mini-game depending on the health information based on the biological information measured during the sleep period. For example, the hand-held terminal 5 determines whether the user has woken up well based on the health information. Specifically, the hand-held terminal 5 may determine that the user has not woken up well when the user has awakened from the non-REM sleep state, while determining that the user has woken up well when the user has awakened from the REM sleep state. Then, the hand-held terminal 5 may prompt the user to launch a mini-game when it is determined that the user has not woken up well. In such a case, the hand-held terminal 5 may display a message such as "You don't seem to have woken up well today. Let's play a mini-game and wake yourself up." in the stand-by image described above, for example. When it is determined that the user has woken up well, the hand-held terminal 5 may not prompt the user to launch a mini-game.

When the mini-game is completed, or when the user gives an instruction to end the mini-game, the hand-held terminal 5 switches the display to the stand-by image (step S13).

(Process after User Gets Out of Bed)

Figure 12:
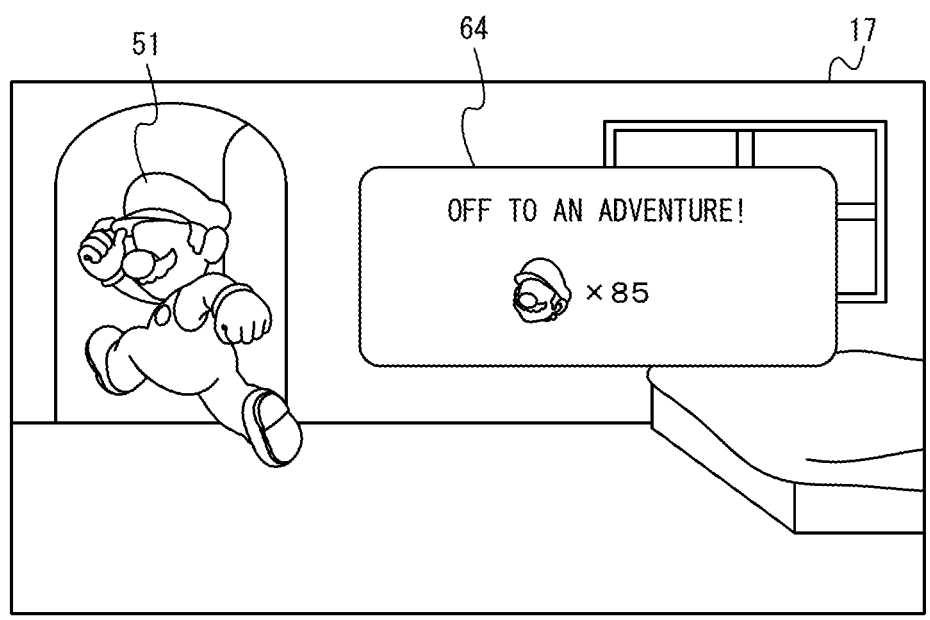
FIG. 12 shows an example out-bed game image to be displayed on a hand-held terminal when the user gets out of bed.

As shown in FIG. 6, the hand-held terminal 5 ends displaying the stand-by image and displays an out-bed game image upon sensing the user getting out of bed (step S16). FIG. 12 shows an example out-bed game image displayed on the hand-held terminal when the user gets out of bed. The out-bed game image shown in FIG. 12 includes the player object 51 and out-of-bed information 64. As shown in FIG. 12, when the user gets out of bed, an image is displayed on the display 17, showing the player object 51 setting out for an adventure.

As shown in FIG. 12, the out-of-bed information 64 represents the evaluation result (specifically, the energy level) at present (i.e., when the user gets out of bed). The energy level calculated when the user awakens may be corrected by the result of the mini-game described above. Then, the out-of-bed information 64 represents the number of lives remaining corresponding to the corrected energy level. It is possible to notify the user of the corrected energy level by means of the out-of-bed information 64. Note that if the energy level calculated when the user awakens is not corrected, the out-of-bed information 64 represents the number of lives remaining equal to the energy level. Note that the out-bed game image may include advice information relating to the evaluation result at present.

The out-bed game image is displayed only for a predetermined amount of time. Then, the hand-held terminal 5 displays the stand-by image (step S17). That is, the hand-held terminal 5 displays a stand-by image similar to that of step S13 on the display 17. Note that the switching from the out-bed game image of step S16 to the stand-by image of step S17 may be done automatically by the hand-held terminal 5 in response to the satisfaction of a predetermined condition as described above, or may be done in response to an instruction from the user.

The stand-by image of step S17 includes the menu image 55 similar to that of the stand-by image of step S13. The stand-by image of step S17 also includes an image representing the player object 51 being out on an adventure. For example, the image to be displayed represents the player object 51 fighting against an enemy or the player object 51 making his/her way through a dungeon.

When the stand-by image is displayed in step S17, as in step S13 described above, the hand-held terminal 5 accepts an input for producing a detail display of the health information and an input for executing a mini-game. That is, when an input is made on the detail display button 56, the hand-held terminal 5 produces a detail display of the health information (step S18). The process of step S18 is similar to the process of step S14. When an input is made on the mini-game button 57, the hand-held terminal 5 starts a mini-game (step S19). The process of step S19 is similar to the process of step S15.

As described above, in the present embodiment, the stand-by image is displayed even after the user gets out of bed, allowing the user to see the detail display or play a mini-game. Therefore, even with the hand-held terminal 5 taken off the base device 6, the user can see the detail display and play a mini-game.

As described above, the mini-game is played for determining how the user has waken up, as one of the purposes. Therefore, if a mini-game is executed after the user is fully awake and the result of the mini-game is reflected in the energy level, how the user has woken up may possibly not be properly reflected in the energy level.

In view of this, in the present embodiment, the hand-held terminal 5 allows a mini-game to be executed within a predetermined amount of time since when the user gets out of bed (or awakens). That is, after the passage of a predetermined amount of time since when the user gets out of bed (or awakens), the hand-held terminal 5 no longer displays the mini-game button 57 on the stand-by image so that the user can no longer play a mini-game. This reduces the possibility that a mini-game is executed after the user is fully awake and the result of the mini-game is reflected in the energy level. Note that in other embodiments, the hand-held terminal 5 may reflect the result of the mini-game in the energy level within a predetermined amount of time since when the user gets out of bed (or awakens), while not reflecting the result of the mini-game in the energy level after the passage of the predetermined amount of time (note that the result of the mini-game may still be reflected in the game process). Then, a mini-game may be allowed to be executed even after the passage of the predetermined amount of time. This achieves a similar effect to that described above.

In the embodiment described above, the terminal system 2 senses the user having gotten out of bed in response to the hand-held terminal 5 being taken off the base device. Any method may be used for sensing that the user has gotten out of bed, and the method is not limited to that described above. For example, in other embodiments, the terminal system 2 may sense the user having gotten out of bed in response to the user having moved out of the sensing range of the Doppler sensor of the base device 6. Then, the hand-held terminal 5 and the base device 6 are capable of communicating with each other wirelessly, and the base device 6 wirelessly notifies the hand-held terminal 5 of sensing the user having gotten out of bed. As described above, the hand-held terminal 5 can execute the processes of steps S11 to S15 described above while the hand-held terminal 5 has been taken off the base device 6. Note that in this case, the hand-held terminal 5 may not execute a mini-game or may not reflect the result of the mini-game in the energy level after sensing the user getting out of bed.

In other embodiments, the hand-held terminal 5 may sense the user having gone out and may execute the process of step S16 described above in response to the user having gone out. Note that the user going out can be sensed based on the sensing result of the location sensing section 13. For example, the location of the user's house may be pre-registered on the hand-held terminal 5, and the hand-held terminal 5 may determine that the user has gone out when the location of the hand-held terminal 5 sensed by the location sensing section 13 has moved a predetermined distance or more away from the location of the user's house.

(Process During Daytime)

After the user goes out of bed, the hand-held terminal 5 calculates various information for correcting the health information (specifically, the energy level) at appropriate points in time (step S20). In the present embodiment, the various information calculated are transmitted to the server 3, and the energy level is corrected at the server 3. Note that although FIG. 6 shows the process of step S20 to be executed after the process of step S17, the timing of execution of the process of step S20 may be before step S17.

Information calculated in the process of step S20 described above is calculated based on the information obtained during the awake period of the user. The information calculated in the process of step S20 is referred to as the awake information. In the present embodiment, the hand-held terminal 5 calculates activity information, environment information and emotion information as the awake information.

The activity information is calculated based on the location information sensed by the location sensing section 13. Specifically, the hand-held terminal 5 calculates the activity information representing the travel distance, the travel time and/or the mode of transportation (e.g., on foot, by train, by car, etc.) of the user, based on the location information described above. The hand-held terminal 5 identifies a location or locations the user has visited based on the location information, and calculates the activity information from the information identified. For example, when the user is identified to have gone to his/her workplace, and activity information is calculated to indicate that the user has worked. For example, if the user is identified to have gone to a massage parlor, activity information is calculated to indicate that the user has received a massage.

The environment information is calculated based on the environment sensor information sensed by the environment sensor 14. Specifically, the hand-held terminal 5 obtains information of the temperature (i.e., the air temperature) as the environment sensor information, and calculates, from the obtained information, the environment information representing the environment which the user is in. For example, the hand-held terminal 5 obtains information of the temperature during a period for which the user is engaged in a predetermined activity, and calculates the environment information representing the average air temperature over that period. Note that the period may be identified based on the location information and/or the activity information. For example, information representing the average air temperature over a period during which the user is moving, or information representing the average air temperature while the user is engaged in an activity (e.g., while working) may be calculated as the environment information.

The emotion information is calculated based on the image captured by the camera 16 and/or the sound sensed by the microphone 15. Specifically, the hand-held terminal 5 captures an image of the face of the user by the camera 16, determines the facial expression of the user from the captured image of the face, and calculates the emotion information representing the emotion of the user from the facial expression. The emotion information may be of any specific content. For example, the emotion information may represent one of four different emotions of delight, anger, sorrow and pleasure, may represent the degree (referred to also as the weight) of each of the four different emotions, or may simply represent whether it is a positive emotion or a negative emotion.

The hand-held terminal 5 obtains the voice of the user by the microphone 15 to calculate the emotion information representing the emotion of the user based on the obtained voice of the user. Any method may be used for determining the emotion based on the user's voice, and conventional emotion determination methods may be used. For example, the hand-held terminal 5 calculates characteristic quantities (e.g., intensity, tempo and intonation, etc.) for each predetermined unit segment of the obtained voice signal so as to calculate an index representing the emotion based on the calculated characteristic quantities. For each of the emotions (e.g., anger, delight and sorrow), the hand-held terminal 5 has a table stored therein, representing the pattern of change of the characteristic quantity. The pattern of change may be created experimentally (i.e., based on the results obtained by actually sensing the voices of subjects and calculating the characteristic quantities). The hand-held terminal 5 compares the pattern of change represented by the table and the change of the characteristic quantity calculated for each of the different emotions so as to identify the emotion of the user based on the comparison result. Thus, emotion information is generated, representing the identified emotion.

The awake information calculated as described above is transmitted to the server 3 by the hand-held terminal 5. Note that the awake information may be transmitted with any timing, and in a case where a plurality of different awake information are calculated, the hand-held terminal 5 may transmit these awake information with different timings. There is no particular limitation on the condition under which the awake information is calculated, and awake information does not need to be calculated in some cases (where the condition is not satisfied).

The server 3 corrects the energy level based on the received awake information. Note that the energy level to be corrected in the present embodiment is the energy level that is calculated when the user awakens or the energy level that has been corrected based on the result of the mini-game. The server 3 corrects the energy level as follows, for example, by using the awake information.

For example, when the received activity information indicates that the user has moved on foot for a long period of time, it is believed that the fatigue of the user will increase. Therefore, in this case, the server 3 corrects the energy level to decrease the energy level. For example, when the received activity information indicates that the user has gone to a massage parlor, it is believed that the fatigue of the user will decrease. Therefore, in this case, the server 3 corrects the energy level to increase the energy level. Note that the degree by which the energy level is increased/decreased may be varied in accordance with the travel distance (or travel time), mode of transportation and/or the activity represented by the activity information.

When the received environment information indicates that it is not comfortable for the user (e.g., when the air temperature is too high while the user is traveling), it is believed that the fatigue of the user will increase. Therefore, in this case, the server 3 corrects the energy level to decrease the energy level.

When the received emotion information represents a positive emotion (e.g., delight or pleasure), it is believed that the fatigue of the user will decrease. Therefore, in this case, the server 3 corrects the energy level to increase the energy level. When the received emotion information represents a negative emotion (e.g., anger or sorrow), it is believed that the fatigue of the user will increase. Therefore, in this case, the server 3 corrects the energy level to decrease the energy level.

As described above, the server 3 corrects the energy level based on the awake information obtained while the user is awake (the activity information, the environment information and the emotion information in the present embodiment). Therefore, the energy level can be calculated while reflecting the activity, circumstances and state of the user while the user is awake. In the present embodiment, the energy level corrected as described above is notified to the user as the energy level for the day. That is, the server 3 transmits the corrected energy level to the hand-held terminal 5 with predetermined timing. Although there is no particular limitation on the predetermined timing, it is in response to the user getting in bed in the present embodiment (the details will be described later). In the present embodiment, the game process is executed based on the corrected energy level, meaning that the awake information described above is reflected in the game process.

Note that in other embodiments, the process of correcting the energy level based on the awake information may be executed by the hand-held terminal 5. Then, the hand-held terminal 5 may transmit the information representing the corrected energy level (and the awake information) to the server 3, and the server 3 may store the received information in the storage section.

Note that after the user gets out of bed, the hand-held terminal 5 may be in a stand-by state (e.g., a state in which the display 17 of the hand-held terminal 5 is OFF) or in a state in which an image produced by another application different from the game application described above is displayed on the display 17. In these states, the game image is not displayed on the display 17. Note however that in these states, the hand-held terminal 5 displays a stand-by image of step S17 described above in accordance with a predetermined instruction input for displaying the game image. Then, the hand-held terminal 5 may receive the energy level at the point in time (if the energy level has been corrected, the corrected energy level) from the server 3, and display the number of lives remaining corresponding to the received energy level. Thus, after the user has gotten out of bed, the hand-held terminal 5 may display information representing the corrected energy level in response to an instruction from the user. Then, it is possible to present, to the user, the energy level at present.

(Process to be Performed when User Gets in Bed)

Figure 13:
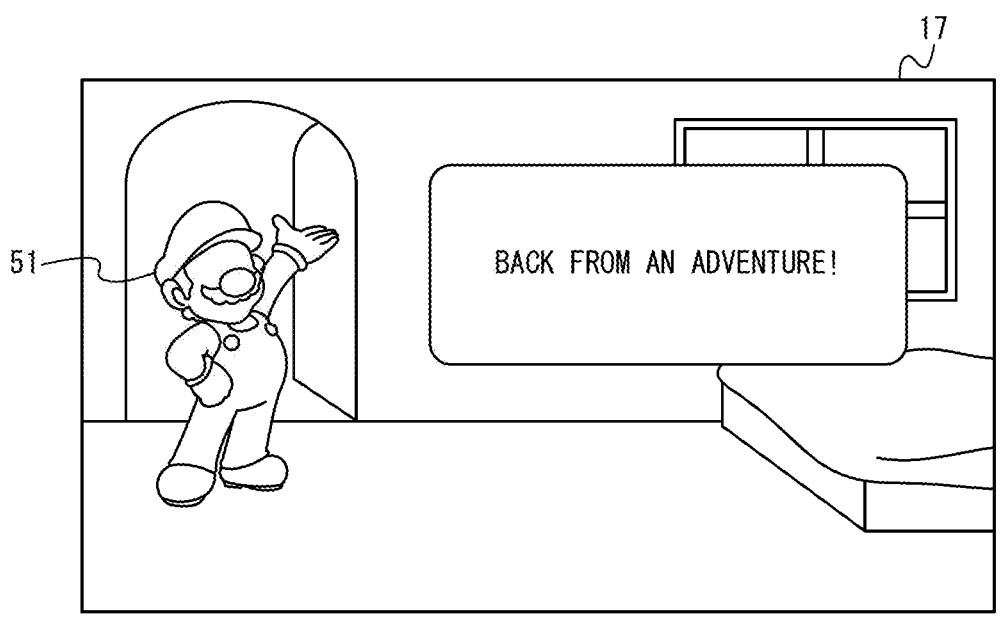
FIG. 13 shows an example in-bed game image to be displayed on a hand-held terminal when the user gets in bed.

As shown in FIG. 6, when sensing the user having gotten in bed, the hand-held terminal 5 displays an in-bed game image (step S21). FIG. 13 shows an example in-bed game image to be displayed on the hand-held terminal when the user gets in bed. The in-bed game image shown in FIG. 13 includes the player object 51 and the out-of-bed information 64. As shown in FIG. 13, when the user gets out of bed, an image is displayed on the display 17, representing the player object 51 having returned from an adventure.

The in-bed game image is displayed only for a predetermined amount of time. Then, the hand-held terminal 5 displays a game image (referred to as a replay game image) representing the replay of the adventure that day (step S22). Note that the switching from the in-bed game image of step S21 to the replay game image of step S22 may be done automatically by the hand-held terminal 5 in response to the satisfaction of a predetermined condition as described above, or may be done in response to an instruction from the user.

In step S22, the hand-held terminal 5 first requests the server 3 to transmit game result information representing the game result. In response to this request, the server 3 transmits the game result information to the hand-held terminal 5. The game result information includes information of the energy level described above (i.e., the corrected energy level). In the present embodiment, the user may be awarded a privilege depending on the game result, the details of which will be described later. Therefore, the game result information includes information relating to a privilege to be awarded to the user.

Figure 14:
FIG. 14 shows an example replay game image.

When the game result information is received from the server 3, the hand-held terminal 5 produces a replay game image based on the game result information, and displays the replay game image on the display 17. FIG. 14 shows an example replay game image. As shown in FIG. 14, the replay game image shows a replay of the adventure that the player object 51 went through during the day (in other words, while the user was awake). For example, it shows the player object 51 fighting against an enemy character 65, as shown in FIG. 14. Note that the image displayed as the replay game image (a video in the present embodiment) may be the same as, or different from, the image representing the player object being out on an adventure, which is displayed as the stand-by image in step S17.

As shown in FIG. 14, the replay game image includes game result information 66 representing the game result. In the present embodiment, the game result information 66 represents, as the game result, the amount of damage given to the enemy character 65. The amount of damage is calculated based on the energy level represented by the game result information. The game result is calculated so that the result is better when the energy level is higher. That is, a better game result is obtained when the user health information represents a better state.

In the present embodiment, the amount of damage is calculated by the same calculation method as the number of lives remaining in the wake-up game image. That is, the amount of damage is the same numerical value representing the energy level as the number of lives remaining, although it is different from the number of lives remaining in terms of how it is expressed as a game element. For example, the number of lives remaining is 80 if the energy level when the user awakens is 80, and the amount of damage is also 80 if the energy level when the user gets in bed is 80. Thus, by presenting values representing the same index as the health information (specifically, the energy level) when the user awakens and when the user gets in bed, it is possible to present changes in the health information during the awake period in an easy-to-understand manner for the user. For example, if the number of lives remaining when the user awakens is 80 and the amount of damage when the user gets in bed is 70, the user can recognize that the energy level has decreased (that is, the fatigue has increased) over the awake period.

Note that in other embodiments, the game result information may include information representing the corrected value of the energy level in accordance with the awake information. Then, the hand-held terminal 5 may display a game element representing the corrected value of the energy level. For example, the hand-held terminal 5 may display the amount of damage corresponding to the energy level when the user awakens and the amount of damage corresponding to the corrected value described above each as the game result information 66.

In other embodiments, the energy level based on the information obtained during the sleep period (e.g., the biological information obtained by the Doppler sensor 24, etc.) and the energy level based on the information obtained during the awake period (e.g., the awake information) may be calculated separately. Then, the hand-held terminal 5 may display these two different energy levels as separate game elements.

The hand-held terminal 5 may display a replay game image representing the player object 51 performing an operation determined in accordance with the awake information (in other words, in accordance with the corrected value corresponding to the awake information). For example, when activity information indicating that the user has traveled a long distance on foot is obtained, an image representing the player object 51 traveling a long distance may be displayed, and an image indicating that the number of lives remaining has decreased may be displayed. When environment information indicating that the user has been in a hot environment is obtained, for example, there may be displayed an image representing the player object 51 traveling through a hot place and there may further be produced a display indicating that the number of lives remaining has decreased. When emotion information representing a positive emotion is obtained, for example, the facial expression of the player object 51 being out on an adventure may change to a smile and there may be produced a display indicating that the number of lives remaining has increased.

In other embodiments, the hand-held terminal 5 may display a replay game image indicating that the player object 51 is awarded an item in accordance with the awake information (in other words, in accordance with the corrected value corresponding to the awake information).

In the present embodiment, the hand-held terminal 5 advances the story of the game in accordance with the game result. Specifically, the game of the present embodiment has a plurality of levels, and the player object 51 can move to the next level by defeating (in other words, giving a predetermined amount of damage to) an enemy character appearing in the current level. Therefore, when the cumulative value of the amount of damage from one or more game results exceeds a predetermined amount, the hand-held terminal 5 displays a replay game image representing the player object 51 defeating the enemy character 65 and further gives a notification that the player object 51 is advancing to the next level.

In the present embodiment, the user may be awarded a privilege depending on the game result. When a privilege is awarded, the game result information 66 is displayed, including information indicating that a privilege has been awarded, as shown in FIG. 14. Note that in the present embodiment, the privilege awarded is a coin or coins that can be used in the game (e.g., with which items can be purchased). Note that although not shown in FIG. 6, in the game of the present embodiment, items can be obtained by using the coins. The privilege is not limited to those relating to the game (e.g., coins and items described above), but may be a privilege relating to a network service provided by the server 3. For example, the privilege may be a point or points that can be used in the network service or may be a content item to be provided on the network service.

Based on the various information (the health information and the awake information in the present embodiment) received from the hand-held terminal 5, the server 3 determines whether or not to award a privilege and, if awarded, what the privilege is. For example, the server 3 determines whether or not to award a privilege and what the privilege is, depending on the energy level calculated based on the various information. The server transmits, to the hand-held terminal 5, the game result information including privilege information relating to a privilege to be awarded. Note that the privilege information may be information representing a privilege to be awarded (e.g., information representing a game item to be awarded or information representing the number of points to be awarded), information of the privilege itself (e.g., data of the content item described above), or information representing a notification that the user is permitted to use the privilege (e.g., a content item) on the hand-held terminal 5. Any specific method may be used for awarding a content item as a privilege as described above, and data of the content item may be transmitted from the server 3 to the hand-held terminal 5, or the data of the content item may be pre-stored in the hand-held terminal 5 and the use of the content item may be permitted (in other words, the content item may be unlocked) in response to the notification described above from the server 3.

When game result information including the privilege information described above is received, the hand-held terminal 5 executes the process of awarding a privilege based on the privilege information. For example, the hand-held terminal 5 changes a parameter of the game process (specifically, a parameter representing items or coins owned by the player object 51) in accordance with items or coins awarded, updates data of the number of points owned by the user on the network service, and stores data of the content item in a predetermined storage section.

Although not shown in FIG. 14, the replay game image may include advice information described above. For example, the server 3 determines the content of advice to generate advice information based on the various information (the health information and the awake information in the present embodiment) received from the hand-held terminal 5. The server 3 transmits the game result information including the generated advice information to the hand-held terminal 5. The hand-held terminal 5 displays the replay game image including the advice information received from the server 3. Note that the generation of the advice information may be done by the hand-held terminal 5.

The display of the replay game image may be automatically stopped by the hand-held terminal 5 in response to the satisfaction of a predetermined condition (e.g., it has been displayed for a predetermined amount of time) or may be stopped in response to an instruction from the user. For example, the display of the replay game image may be stopped in response to the sleep onset of the user.

Note that in the embodiment described above, the terminal system 2 senses the user getting in bed in response to the hand-held terminal 5 being docked onto the base device. The method for sensing the user getting in bed may be any method and is not limited to the method described above. For example, in other embodiments, the terminal system 2 may sense the user getting in bed in response to the user moving into the sensing range of the Doppler sensor 24 of the base device 6.

In this case, in order to start the sensing by the Doppler sensor 24 before the user gets in bed, the Doppler sensor 24 may automatically start sensing in response to the satisfaction of a predetermined condition. For example, in cases in which the hand-held terminal 5 and the base device 6 are capable of communicating with each other wirelessly, the base device 6 may be given an instruction to start the sensing by the Doppler sensor 24 on the condition that the hand-held terminal 5 has moved within a predetermined range of the base device 6. Note that the determination of whether or not the hand-held terminal 5 has moved within a predetermined range of the base device 6 may be made by determining whether or not the base device 6 has come within a communication range of the hand-held terminal 5 in cases in which the hand-held terminal 5 and the base device 6 are capable of near field radio communication with each other. For example, the determination may be made by determining whether or not the hand-held terminal 5 is located in the user's house based on the location sensed by the location sensing section 13. In other embodiments, the hand-held terminal 5 may give the base device 6 an instruction to start the sensing by the Doppler sensor 24 in response to the user giving a predetermined input instruction to the hand-held terminal 5.

In other embodiments, the terminal system 2 may set an expected in-bed time so as to start the sensing by the Doppler sensor 24 in response to the expected in-bed time being reached. Note that the expected in-bed time may be specified by the user, or may be calculated based on the user's past in-bed time and/or sleep onset time. For example, the terminal system 2 may store the sleep onset time for the past month so as to set, as the expected in-bed time, a time that is a predetermined amount of time before (e.g., an hour before) the average sleep onset time for the past month.

In other embodiments, the hand-held terminal 5 may sense the user's homecoming and execute the process of step S21 described above in response to the user's homecoming. Note that while any method may be used for sensing the user's homecoming, it may be sensed based on the sensing result of the location sensing section 13, for example. Specifically, the location of the user's house may be pre-registered on the hand-held terminal 5, and the hand-held terminal 5 may determine that the user has come home when the location of the hand-held terminal 5 sensed by the location sensing section 13 comes within a predetermined distance from the location of the user's house. For example, the terminal system 2 may sense homecoming by using the Doppler sensor 24 of the base device 6. That is, the terminal system 2 may activate the Doppler sensor 24 intermittently (e.g., at the rate of once per a predetermined amount of time) to determine the presence/absence of the user, and determine that the user has come home when the presence of the user is determined. For example, the terminal system 2 may have a sensing unit (e.g., a human sensor such as a camera or an infrared sensor) provided at a predetermined location in the user's house, and sense the user's homecoming based on the sensing result of the sensing unit.

As described above, in the present embodiment, in response to the user getting in bed, an image representing the player object 51 having returned from an adventure is displayed, and an image representing the replay of the adventure and the game result that day (the amount of damage given to the enemy character in the present embodiment) is displayed. Then, when the user gets in bed, it is possible to present, to the user, the energy level that reflects the state and/or activity of the user that day. When the user gets in bed, as when awakening, the energy level is displayed as a game element, and the user can check the health information (the energy level in the present embodiment) as if by playing a video game, thereby motivating the user to continuously do the daily check.

In the present embodiment, the game process is executed, in which the user health information is used as the game input. That is, the user measures the health information, thereby making a game input, and the game does not progress unless the user measures the health information. Thus, it is possible to have the user measure the health information as if by playing a video game, and it is possible to motivate the user to continuously perform the daily measurement.

Note that in the series of processes of steps S11 to S22 described above, the game image is displayed on the display 17 at appropriate points in time (steps S11 to S13, S16, S17, S21, S22). At these points in time, the hand-held terminal 5 may be in a stand-by state so that the display of the display 17 is OFF, or an image of another application different from the game application may be on the display 17. In such a case, the hand-held terminal 5 may notify the user using a sound, display and/or vibrations, instead of immediately displaying the game image. The hand-held terminal 5 may display the game image on the display 17 in response to the notified user making a predetermined display instruction input.

Note that in the embodiment described above, advice information is presented to the user at an appropriate point in time (when the user awakens, etc.). In other embodiments, the terminal system 2 may present, to the user, information different from the advice information so as to improve the content of the calculated health information (e.g., evaluation result). That is, the terminal system 2 may present recommendation information to the user or may output a content item, in addition to the advice information or instead of the advice information. The recommendation information is information of introducing a product, or the like, to be recommended to the user in order to improve the content of the calculated health information. The content item is a piece of music and/or an image to be recommended to the user in order to improve the content of the calculated health information.

An image to be displayed before the user gets out of bed and/or an image to be displayed after the user gets in bed may be projected by the terminal system 2 using the projector 25 of the base device 6, in addition to (or instead of) displaying the images on the display 17 of the hand-held terminal 5. Then, the user can check the evaluation result, etc., without picking up the hand-held terminal 5 when the user awakens. Note that the image to be displayed before the user gets out of bed is, for example, the wake-up game image, the simplified display image and/or the stand-by image described above. The image to be displayed after the user gets in bed is, for example, the in-bed game image and/or the replay game image described above.

As described above, in response to sensing the user getting in bed, the hand-held terminal 5 starts the measurement for calculating the user health information (step S23). Note that although FIG. 6 shows the measurement start timing (step S23) to be after displaying the replay game image (step S22), the measurement may be started at any point in time in conjunction with the user getting in bed.

When the measurement is started, the terminal system 2 calculates the sleep indices based on the measurement result as described above. Then, the terminal system 2 executes information processes in accordance with the sleep state represented by the sleep indices (step S24). The following processes are executed, for example, as the information processes.

Process of reproducing a sleep-inducing content item (specifically, a piece of music and/or an image that induces the user to fall asleep) before the user falls asleep and ending the reproduction in response to the user falling asleep Process of displaying the current time when the user awakens mid-sleep Process of starting the reproduction of an awakening content item (specifically, a piece of music and/or an image that induces the user to wake up) at a point in time shortly before the user awakens Process of changing the state of the hand-held terminal 5 (e.g., turning OFF the power, switching to the stand-by state, switching to the silent mode, etc.) in response to the user falling asleep Process of changing the state of the hand-held terminal 5 (e.g., turning ON the power, disengaging the silent mode, etc.) in response to the user awakening Note that in the various processes described above, an image may be presented to the user by using the display 17 of the hand-held terminal 5, the projector 25 of the base device 6, or both of them.

3. Specific Example Process of Information Processing System

Next, specific example processes to be executed in the information processing system will be described.

First, referring to FIG. 15 to FIG. 18, specific example processes to be executed by the terminal system 2 will be described. The hand-held terminal 5 executes the measurement process, the wake-up process, the daytime process and the in-bed process. In the present embodiment, these processes are executed by the processing section 11 executing the game program stored in the hand-held terminal 5. Note that in other embodiments, some of these processes (e.g., the measurement process) may be implemented by another program different from the game program. Some or all of the various processes described above may be executed by another information processing device (e.g., the base device 6 and/or the server 3), or the various processes may be executed by a cooperation between the hand-held terminal 5 and the other information processing device.

The measurement process is a process of calculating the health information by measuring the biological information primarily during the sleep period of the user. The wake-up process is a process of presenting, to the user, the game image, etc., including the evaluation result of the health information (specifically, the energy level) primarily when the user wakes up. The daytime process is a process of calculating the awake information (specifically, the activity information, the environment information and the emotion information) described above primarily during the daytime active period (in other words, from when the user gets out of bed until the user gets in bed). The in-bed process is a process of presenting, to the user, the game image, etc., including the evaluation result of the health information for the day primarily when the user gets in bed. Thus, the various processes described above are executed generally during different periods of time, but two or more of the various processes may be executed in parallel during a certain period of time. The various processes will now be described in detail.

(3-1: Measurement Process)

Figure 15:
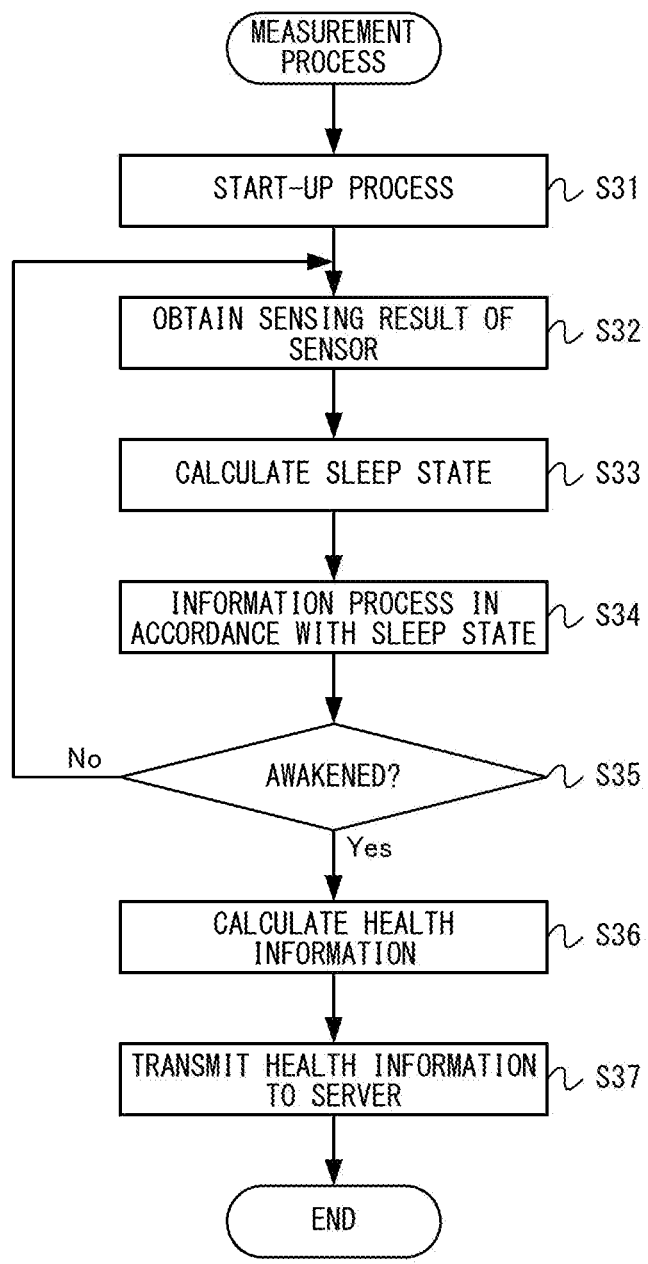
FIG. 15 is a flow chart showing an example flow of a measurement process to be executed on an example hand-held terminal.

FIG. 15 is a flow chart showing an example flow of the measurement process to be executed on the hand-held terminal 5. In the present embodiment, the series of processes shown in FIG. 15 is started in response to sensing the user getting in bed, i.e., in response to the hand-held terminal 5 being docked onto the base device 6. Note that in other embodiments, the series of processes may be started in response to the start of communication between the hand-held terminal 5 and the base device 6 or in response to the user performing a predetermined start operation on the hand-held terminal 5 or the base device 6.

Note that in the present application, the processes of the various steps of the flow charts shown in the drawings are merely illustrative, and the order of steps to be performed may be switched around or other processes may be executed in addition to (or instead of) the processes of the various steps, as long as similar results are obtained. While processes of the steps of the flow charts are herein executed by the CPUs of the various devices (specifically, the hand-held terminal 5, the base device 6 and the server 3), one or more steps of the flow charts may be executed by a processor or a dedicated circuit other than the CPUs.

In the measurement process, first, in step S31, the hand-held terminal 5 executes a start-up process. The start-up process is a process that is executed in response to the start of the series of processes shown in FIG. 15 (in response to the hand-held terminal 5 being docked onto the base device 6 in the present embodiment). In the present embodiment, a sensing start process and a reproduction start process are executed (the details of which will be described later) as the start-up process.

In the sensing start process, the hand-held terminal 5 starts sensing by the sensor (i.e., the Doppler sensor 24) for sensing the biological information for calculating the health information. That is, the processing section 11 of the hand-held terminal 5 gives the base device 6 an instruction to start the sensing operation. In response to this instruction, the control section 22 of the base device 6 causes the Doppler sensor 24 to start the sensing operation.

In the reproduction start process, the hand-held terminal 5 starts reproducing a sleep-inducing content item. That is, the processing section 11 loads a pre-stored sleep-inducing content item and reproduces the sleep-inducing content item using the display 17 and/or a speaker. Note that the content item (i.e., a sleep-inducing content item or an awakening content item) to be reproduced on the terminal system 2 may be stored in the base device 6 or in the hand-held terminal 5, or may be obtained from an external device (e.g., the server 3) via the hand-held terminal 5.

When the start-up process of step S31 is executed (in other words, in response to the hand-held terminal 5 being docked onto the base device 6), the base device 6 executes a charge start process. In the charge start process, the base device 6 starts charging the hand-held terminal 5. Specifically, the control section 22 gives a power obtaining section 23 an instruction to start the charge. In response to this instruction, the power obtaining section 23 supplies power from an external power source to the hand-held terminal 5 via the connector 21. Note that it is assumed that the base device 6 is connected to an external power source (i.e., the power plug is connected to an outlet). Note that the base device 6 may check the remaining battery level of the hand-held terminal 5, and may start the charging operation on the condition that the remaining battery level is less than or equal to a predetermined amount. The charging operation is ended in response to the battery of the hand-held terminal 5 is fully charged.

Note that in other embodiments, any process may be executed as the start-up process, and any one or two of the three processes (i.e., the sensing start process, the reproduction start process and the charge start process) may be executed, or other processes different from these three processes may be executed, or no start-up process may be executed.

After the process of step S31 described above, the processes of steps S32 to S38 to be described below are executed repeatedly during the sleep period. Note that in the present embodiment, the process loop of steps S32 to S38 is executed at the rate of once per a predetermined amount of time.

In step S32, the hand-held terminal 5 obtains the sensing result of the Doppler sensor 24 (i.e., the biological information). The Doppler sensor 24, which has started the sensing operation in the sensing start process of step S31 described above, outputs the sensing result (specifically, the output waveform) to the control section 22. The control section 22 transmits the sensing result to the hand-held terminal 5. Thus, the sensing result of the Doppler sensor 24 is obtained by the hand-held terminal 5. Note that the control section 22 may transmit the information of the sensing result of the Doppler sensor 24 as it is to the hand-held terminal 5, or may process the sensing result (e.g., the process of removing noise contained in the sensing result signal, the process of calculating the sleep indices, etc.) before transmitting it to the hand-held terminal 5.

In step S33, the hand-held terminal 5 calculates the sleep information (e.g., various sleep indices). That is, the processing section 11 calculates the various sleep indices based on the sensing result (e.g., the biological information) obtained in step S32. The calculation of the sleep indices is done by the method described in "(2-2: Method for calculating health information)" above. Note that in step S33, the processing section 11 may calculate information (i.e., the sleep indices) used for determining the sleep state of the user in steps S34 and S35 to be described later. In step S33, the processing section 11 may not calculate the sleep indices (e.g., the total sleep time), the fatigue information (in other words, the fatigue level) and the energy level, which can only be calculated at the end of the sleep period.

In step S34, the hand-held terminal 5 executes an information process in accordance with the sleep state of the user (step S24 shown in FIG. 6). That is, the processing section 11 determines whether or not the sleep state of the user has become a predetermined state, as in step S24 described above. Then, when it is determined that it has become a predetermined state, the operation of the hand-held terminal 5 (and the base device 6), the operation mode and/or the settings are controlled.

In step S35, the hand-held terminal 5 determines whether or not the user has awakened. That is, the processing section 11 determines whether or not the user has awakened based on the biological information obtained in step S32 and/or the sleep indices calculated in step S33. When it is determined that the user has awakened, the series of processes of steps S36 to S38 is executed. On the other hand, if it is determined that the user has not awakened, the series of processes of steps S36 to S38 is skipped, and the process of step S32 is executed again. That is, the series of processes of steps S32 to S35 is executed repeatedly until it is determined that the user has awakened.

In step S36, the hand-held terminal 5 calculates the health information based on the information obtained during the sleep period (specifically, the biological information). The health information is calculated by the method described in "(2-2: Method for calculating health information)" above. In the present embodiment, in step S36, the processing section 11 first calculates the autonomic nerve index based on the biological information obtained in step S32. The processing section 11 calculates the sleep indices that cannot be calculated during the sleep period (e.g., the total sleep time, etc.) based on the biological information obtained in step S32. Moreover, the processing section 11 calculates the fatigue level and the energy level based on the various sleep indices and the autonomic nerve index. Thus, the health information including the sleep indices and the fatigue index is calculated.

In step S37, the hand-held terminal 5 transmits the health information calculated in step S36 to the server 3. That is, the processing section 11 transmits the calculated health information to the server 3 by means of the communication section 10. Thus, the health information for one sleep period is transmitted to the server 3 and stored in the server 3. Thus, in the present embodiment, the hand-held terminal 5 automatically transmits, to the server 3, information to be transmitted. That is, the information is uploaded to the server 3 even without an instruction from the user.

After step S37 described above, the hand-held terminal 5 ends the measurement process. The processing section 11 of the hand-held terminal 5 gives an instruction to stop the sensing operation to the base device 6. In response to this instruction, the control section 22 of the base device 6 stops the sensing operation of the Doppler sensor 24.

Note that in the present embodiment, if the hand-held terminal 5 is taken off the base device 6 for some reason (e.g., the user knocking the hand-held terminal 5 when rolling over) during the sleep period, the base device 6 cannot transmit the sensing result of the Doppler sensor 24 to the hand-held terminal 5. Then, the base device 6 stores, in its storage section (e.g., a memory, etc.), the data of the sensing result that has not been transmitted to the hand-held terminal 5. Then, in response to the hand-held terminal 5 being next docked onto the base device 6, the base device 6 transmits the data of the sensing result stored in the storage section to the hand-held terminal 5. The hand-held terminal 5, having received the data, calculates the sleep indices based on the sensing result (step S33). Note that the hand-held terminal 5 may not execute a control process based on the calculated sleep indices (step S34). This is because the calculated sleep indices are based on a past sensing result.

If it is determined that the user has awakened based on the calculated sleep indices (if the determination result of step S35 is affirmative), the hand-held terminal 5 executes the processes of steps S36 to S38 described above. Thus, even if the hand-held terminal 5 is taken off the base device 6 while the user is asleep, the health information is calculated and transmitted to the server 3 when the hand-held terminal 5 is next docked onto the base device 6. Therefore, when the user awakens and notices that the hand-held terminal 5 is off the base device 6, for example, the user can dock the hand-held terminal 5 onto the base device 6. Then, the terminal system 2 can calculate and transmit the health information to the server 3.

Note that in other embodiments, when the hand-held terminal 5 and the base device 6 are capable of wireless communication with each other, the processes of steps S32 to S35 described above can be executed continuously even if the hand-held terminal 5 is taken off the base device 6.

(3-2: Wake-Up Process)

Figure 16:
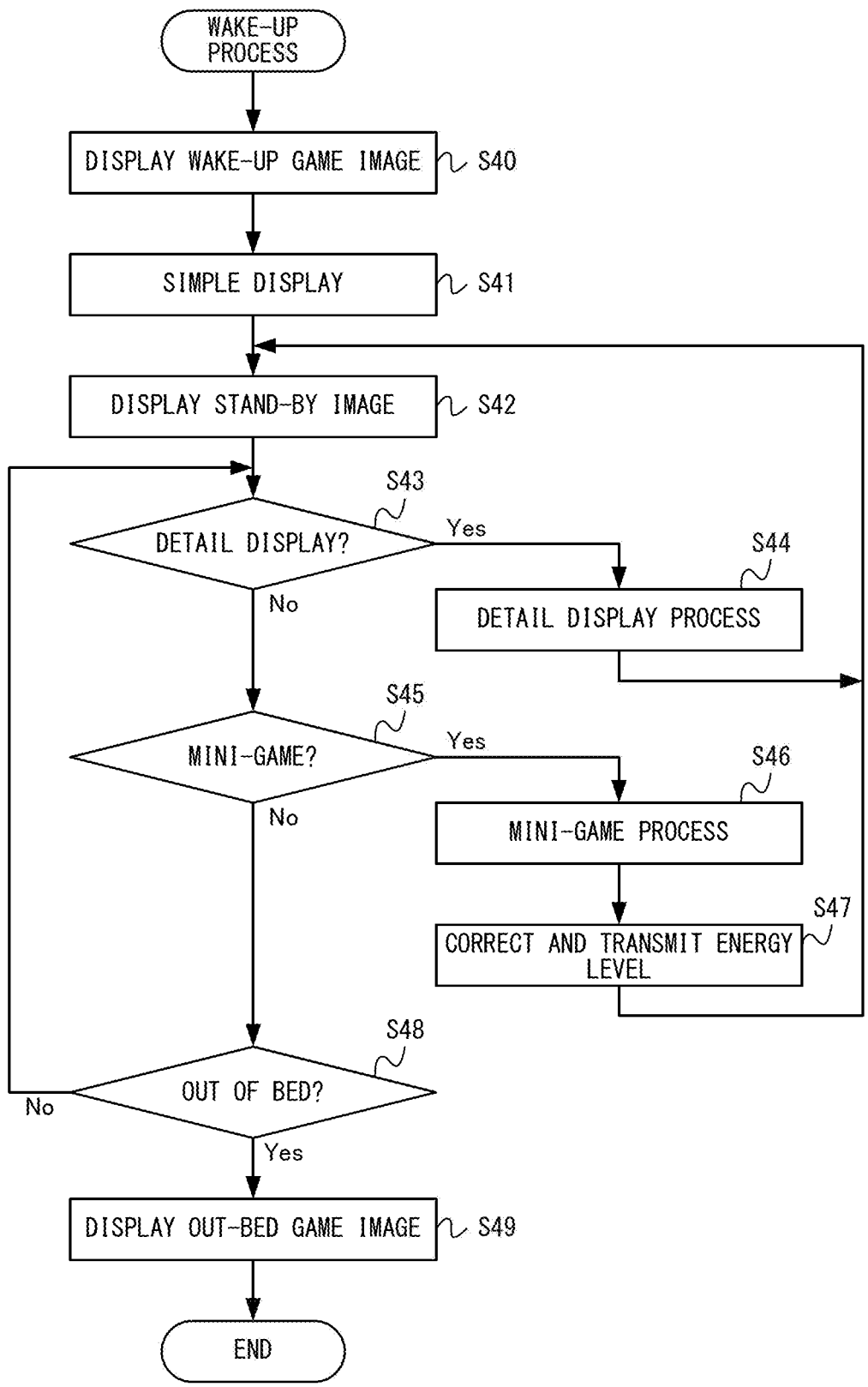
FIG. 16 is a flow chart showing an example flow of a wake-up process to be executed on an example hand-held terminal.

FIG. 16 is a flow chart showing an example flow of the wake-up process to be executed on the hand-held terminal 5. In the present embodiment, the series of processes shown in FIG. 16 is started in response to sensing the user having awakened (Yes in step S35).

In the wake-up process, first, in step S40, the hand-held terminal 5 displays the wake-up game image described above (step S11 shown in FIG. 6). Note that before step S40, the processing section 11 calculates the evaluation result of the health information (specifically, the energy level) in the process of step S36 in the measurement process described above (FIG. 15). The processing section 11 generates the wake-up game image based on the calculated health information and displays the wake-up game image on the display 17. After the passage of a predetermined amount of time from when the wake-up game image is displayed, the process of step S41 is executed.

In step S41, the hand-held terminal 5 displays the simplified display image described above (step S12 shown in FIG. 6). That is, the processing section 11 generates the simplified display image based on the health information calculated in the process of step S36 described above, and displays the simplified display image on the display 17. After the passage of a predetermined amount of time from when the simplified display image is displayed, the process of step S42 is executed.

In step S42, the hand-held terminal 5 displays the standby image described above (step S13 shown in FIG. 6). That is, the processing section 11 displays a stand-by image, prepared in advance, on the display 17.

In step S43, the hand-held terminal 5 determines whether or not to produce a detail display. That is, while the stand-by image is displayed, the processing section 11 determines whether or not an instruction input for producing a detail display (e.g., an input on the detail display button 56 described above) has been made. If the determination result of step S43 is affirmative, the process of step S44 is executed. On the other hand, if the determination result of step S43 is negative, the process of step S45 is executed.

In step S44, the hand-held terminal 5 executes a detail display process (step S14 shown in FIG. 6). In the detail display process, the processing section 11 produces various detail display images (FIG. 10 and FIG. 11) based on the health information calculated in the process of step S36 described above, and displays the detail display images on the display 17. Depending on the detail display image, the processing section 11 may load the past health information stored in the hand-held terminal 5 and produce detail display images based on the health information. The processing section 11 may receive health information of other users from the server 3 and produce detail display images based on the health information. The process of step S44 described above is ended in response to the user inputting a predetermined end instruction (e.g., an input on the menu button 59), and then the process of step S42 is executed again.

On the other hand, in step S45, the hand-held terminal 5 determines whether or not to execute a mini-game. That is, while the stand-by image is displayed, the processing section 11 determines whether or not an instruction input for executing the mini-game (e.g., an input on the mini-game button 57) has been made. If the determination result of step S45 is affirmative, the processes of steps S46 and S47 are executed. On the other hand, if the determination result of step S45 is negative, the process of step S48 to be described later is executed.

In step S46, the hand-held terminal 5 executes the mini-game (step S15 shown in FIG. 6). That is, the processing section 11 receives game inputs from the user, executes the mini-game process in accordance with the game inputs, and displays the game image representing the result of the mini-game on the display 17. When the mini-game is ended, or when the user gives an instruction for ending the mini-game, the process of step S46 is ended, and then the process of step S47 is executed.

In step S47, the hand-held terminal 5 corrects the energy level based on the mini-game result and transmits the corrected energy level to the server 3. That is, the processing section 11 corrects the energy level calculated in step S36 based on the result of the mini-game of step S46. Moreover, the processing section 11 transmits information representing the corrected energy level to the server 3 by means of the communication section 10. After step S47, the process of step S42 is executed again.

On the other hand, in step S48, the hand-held terminal 5 determines whether or not the user has gotten out of bed. That is, the processing section 11 determines whether or not the hand-held terminal 5 has been taken off the base device 6. If the determination result of step S48 is affirmative, the process of step S49 is executed. On the other hand, if the determination result of step S48 is negative, the process of step S43 is executed again. That is, in such a case, the stand-by image is displayed continuously.

In step S49, the hand-held terminal 5 displays the out-bed game image described above. That is, the processing section 11 generates an out-bed game image based on the health information (specifically, the energy level) calculated in the process of step S36 or step S47 described above, and displays the out-bed game image on the display 17. After the passage of a predetermined amount of time from when the out-bed game image is displayed, the hand-held terminal 5 ends the series of wake-up processes shown in FIG. 16.

(3-3: Daytime Process)

Figure 17:
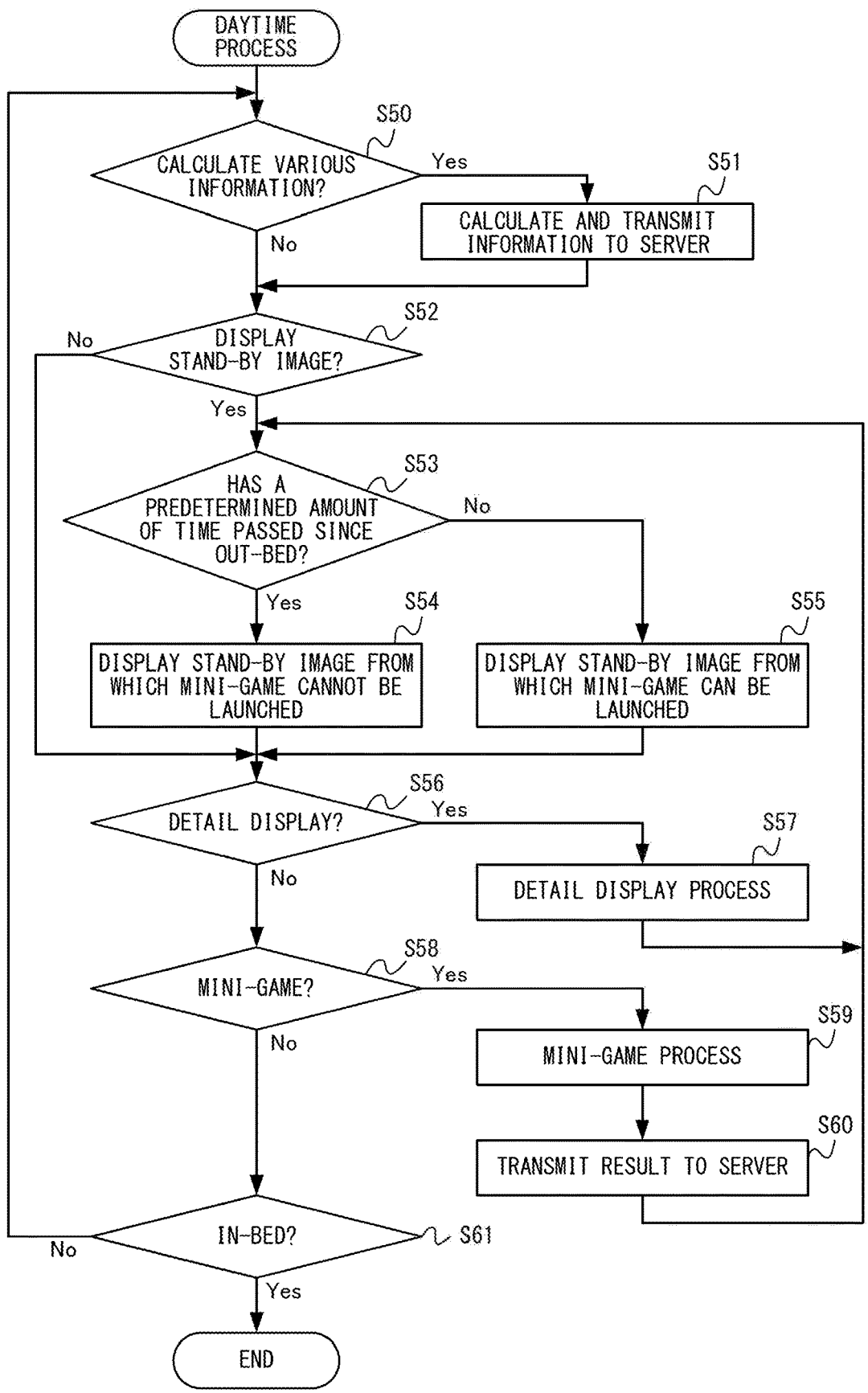
FIG. 17 is a flow chart showing an example flow of a daytime process to be executed on an example hand-held terminal.

FIG. 17 is a flow chart showing an example flow of the daytime process executed on the hand-held terminal 5. In the present embodiment, the series of processes shown in FIG. 17 is started in response to the ending of the wake-up process (FIG. 16) (in other words, following the wake-up process).

In step S50, the hand-held terminal 5 determines whether or not to calculate the awake information for correcting the health information (specifically, the energy level) (in other words, whether or not the timing for calculating the awake information has arrived). That is, the processing section 11 performs the process of determining whether or not a condition for calculating any of the various awake information has been satisfied. While the determination process may be of any specific content, the determination process is performed by the following method in the present embodiment.

For activity information, the processing section 11 determines whether or not a condition for calculating the activity information has been satisfied. While there is no particular limitation on this calculation condition, the condition used in the present embodiment is that the user has stopped moving (the first condition) and that the user has stayed in a place where the activity information is calculated (the second condition). When either the first condition or the second condition is satisfied, it is determined that the condition for calculating the activity information is satisfied.

Whether the first condition is satisfied can be determined based, for example, on whether or not the sensed location represented by the location information moves from one place and then stopped at another place for a predetermined amount of time or more (e.g., 10 minutes or more).

Whether the second condition is satisfied can be determined as follows. That is, the processing section 11 first determines whether or not the sensed location starts moving after staying in a pre-registered place for a predetermined amount of time or more (e.g., 15 minutes or more). If it is determined that the sensed location has not stayed for a predetermined amount of time or more or has not started moving, the processing section 11 determines that the second condition is not satisfied. Note that the "pre-registered place" may be a place relating to the user, such as the house or the workplace of the user, for example, or may be an establishment such as a fitness club, a restaurant or a movie theater. When it is determined that the user has stayed in such a place, the activity information is calculated.

For environment information, the processing section 11 determines whether or not the condition for calculating the environment information is satisfied. In the present embodiment, the environment information is calculated at a point in time when the activity information is calculated. Therefore, the processing section 11 makes the determination based on whether or not the activity information is calculated.

For emotion information, the processing section 11 determines whether or not the condition for calculating the emotion information is satisfied. In the present embodiment, the following conditions are used, for example, as the condition for calculating the emotion information.

Period during which voice or image of user is sensed (e.g., a period greater than or equal to predetermined length) has ended User has ended a phone call using the hand-held terminal 5

Predetermined event period has ended

Note that the voice/image of the user can be identified by pre-registering data of the voice/image of the user on the hand-held terminal 5 and comparing the voice/image sensed by the microphone 15 with the registered voice/image. A predetermined event period can be identified based on information (e.g., a meeting, etc.) that is registered as a schedule item on the hand-held terminal 5, for example.

In step S50, the processing section 11 obtains information for calculating the awake information (specifically, the location information, the environment sensor information, the information of the image captured by the camera 16, and the information of the sound sensed by the microphone 15), and performs the determination process described above based on the obtained information. If the determination result of step S50 is affirmative, the process of step S51 is executed. On the other hand, if the determination result of step S50 is negative, the process of step S52 is executed, skipping the process of step S51.

In step S51, the hand-held terminal 5 performs a calculation process on those of the various awake information for which the calculation condition is satisfied. Then, the hand-held terminal 5 transmits the calculated information to the server 3. Specifically, if the condition for the activity information is satisfied in step S50, the processing section 11 calculates the activity information based on the location information. If the condition for the environment information is satisfied in step S50, the processing section 11 calculates the environment information based on the environment sensor information. If the condition for the emotion information is satisfied in step S50, the processing section 11 calculates the emotion information based on the image captured by the camera 16 and/or the voice sensed by the microphone 15. Then, the processing section 11 transmits the calculated information to the server 3 by means of the communication section 10. The process of step S52 is executed, following step S51.

In step S52, the hand-held terminal 5 determines whether or not to display the stand-by image. That is, the processing section 11 determines whether or not the stand-by image display timing (i.e., a point in time after the passage of a predetermined amount of time since when the display of the out-bed game image started in step S49 described above) has arrived, and whether or not a predetermined instruction input for displaying the game image has been made. Then, if it is determined that the display timing has arrived or if it is determined that the instruction input has been made, the processing section 11 determines to display the stand-by image and executes the process of step S53. On the other hand, if it is determined that the display timing has not arrived and it is determined that the instruction input has not been made, the processing section 11 determines not to display the stand-by image and executes the process of step S56 to be described later.

In step S53, the hand-held terminal 5 determines whether or not a predetermined amount of time has passed since when the user got out of bed. That is, the processing section 11 determines whether or not a predetermined amount of time has passed since when the determination result in step S48 described above became affirmative. If the determination result of step S53 is affirmative, the process of step S54 is executed. On the other hand, if the determination result of step S53 is negative, the process of step S55 is executed.

In step S54, the hand-held terminal 5 displays a stand-by image from which the mini-game cannot be launched (step S17 shown in FIG. 6). That is, the processing section 11 displays a stand-by image that does not include the mini-game button 57 on the display 17. When this stand-by image is displayed, the user cannot launch the mini-game. After step S54, the process of step S56 is executed.

In step S55, the hand-held terminal 5 displays a stand-by image from which the mini-game can be launched (step S17 shown in FIG. 6). That is, the processing section 11 displays a stand-by image that includes the mini-game button 57 (FIG. 9) on the display 17. When this stand-by image is displayed, the user can launch the mini-game. After step S55, the process of step S56 is executed.

In step S56, the hand-held terminal 5 determines whether or not to produce a detail display. The determination process of step S56 is the same as the determination process of step S43. Note that when the stand-by image is not displayed in the process of step S56, it is determined not to produce a detail display. If the determination result of step S56 is affirmative, the process of step S57 is executed. On the other hand, if the determination result of step S56 is negative, the process of step S58 is executed.

In step S57, the hand-held terminal 5 executes a detail display process (step S18 shown in FIG. 6). The detail display process of step S57 is the same as the detail display process of step S44. The process of step S57 is ended in response to the user giving a predetermined end instruction (specifically, the user making an input on the menu button 59), and then the process of step S53 is executed again.

In step S58, the hand-held terminal 5 determines whether or not to execute a mini-game. The determination process of step S58 is the same as the determination process of step S45. Note that if the stand-by image is not displayed in the process of step S58, it is determined that the mini-game is not to be played. If the determination result of step S58 is affirmative, the process of step S59 is executed. On the other hand, if the determination result of step S58 is negative, the process of step S61 is executed.

In step S59, the hand-held terminal 5 executes the mini-game (step S19 shown in FIG. 6). The mini-game process of step S59 is the same as the mini-game process of step S46.

In the following step S60, the hand-held terminal 5 corrects the energy level based on the mini-game result and transmits the corrected energy level to the server 3. The process of step S60 is the same as the process of step S47. The process of step S61 is executed, following step S60.

In step S61, the hand-held terminal 5 determines whether or not the user has gotten in bed. That is, the processing section 11 determines whether or not the hand-held terminal 5 has been docked onto the base device 6. If the determination result of step S61 is negative, the process of step S50 is executed again. Then, the series of processes of steps S50 to S61 is executed repeatedly until it is determined that the user has gotten in bed. On the other hand, if the determination result of step S61 is affirmative, the processing section 11 ends the daytime process shown in FIG. 17.

(3-4: In-Bed Process)

Figure 18:
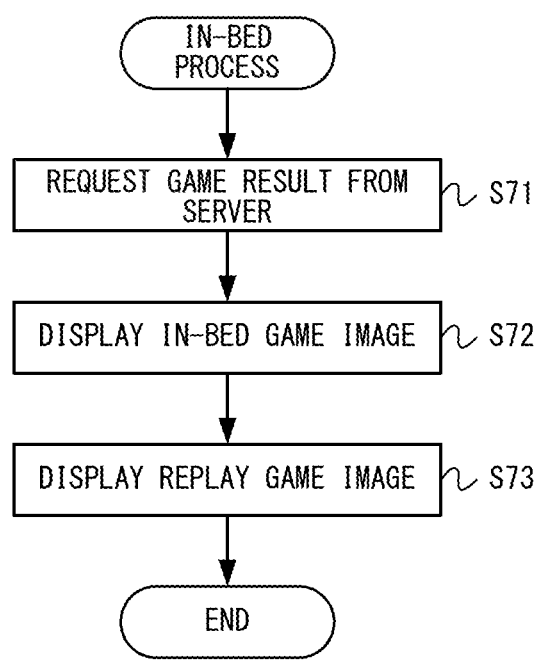
FIG. 18 is a flow chart showing an example flow of an in-bed process to be executed on an example hand-held terminal.

FIG. 18 is a flow chart showing an example flow of the in-bed process executed on the hand-held terminal 5. In the present embodiment, the series of processes shown in FIG. 18 is started in response to sensing the user having gotten in bed (Yes in step S61).

In the in-bed process, first, in step S71, the hand-held terminal 5 requests the server 3 to transmit game result information representing the game result (specifically, the game result based on the energy level for the day). In response to this, the server 3 transmits the game result information of this user to the hand-held terminal 5. The processing section 11 receives the game result information transmitted from the server 3 via the communication section 10 and stores the game result information in the storage section of the hand-held terminal 5.

In the following step S72, the hand-held terminal 5 displays the in-bed game image described above (step S21 shown in FIG. 6). That is, the processing section 11 displays an in-bed game image, prepared in advance, on the display 17. After the passage of a predetermined amount of time since when the in-bed game image is displayed, the process of step S73 is executed.

In step S73, the hand-held terminal 5 displays the replay game image described above (step S22 shown in FIG. 6). That is, the processing section 11 generates an in-bed game image based on the game result information received from the server 3 via the communication section 10 and displays the in-bed game image on the display 17 (see FIG. 14). Thus, the user is presented a game result based on the energy level for one day, and in some cases, the user is awarded a privilege. After the passage of a predetermined amount of time since when the reproduction of the video of the replay game image is ended in step S73, the hand-held terminal 5 ends the in-bed process shown in FIG. 18.

(3-5: Processes Performed on Server)

Next, referring to FIG. 19, specific example processes to be executed on the server 3 will be described. As described above, the hand-held terminal 5 transmits the health information, etc., to the server 3. The server 3 evaluates the health (i.e., corrects the energy level) of the user based on the received information, and provides a network service in accordance with the evaluation result. The details of the processes to be executed on the server 3 will now be described.

Figure 19:
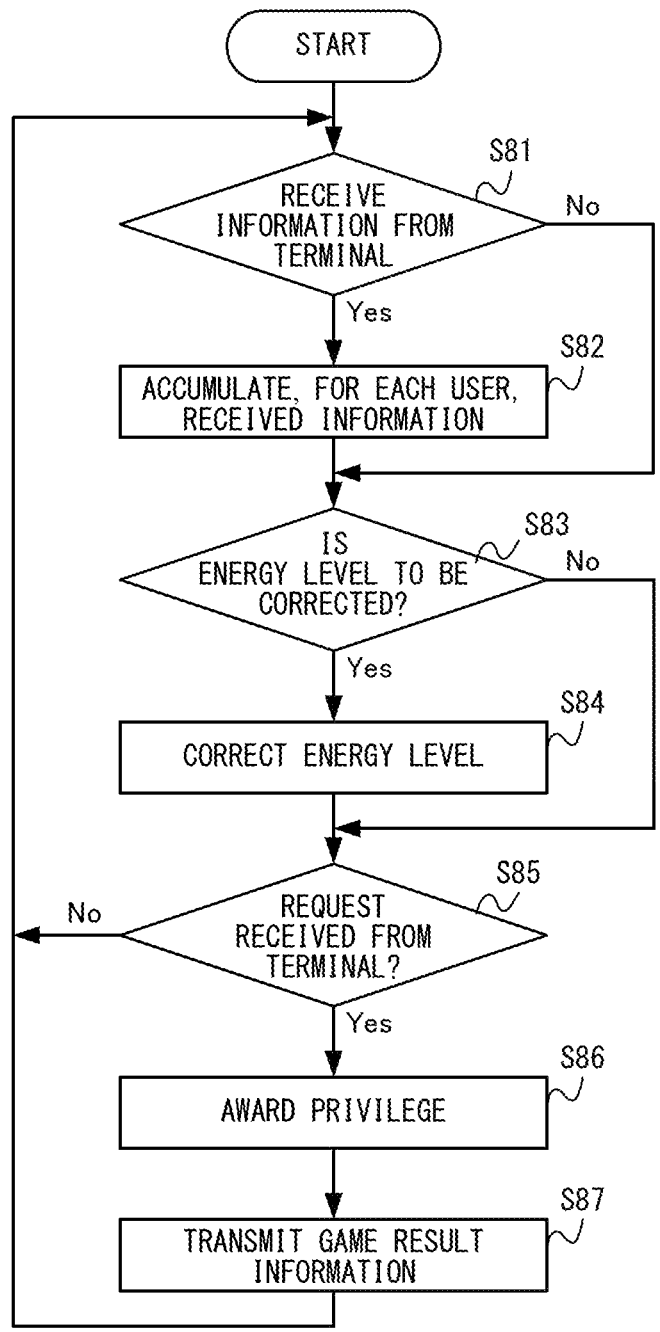
FIG. 19 is a flow chart showing an example flow of a process to be executed on an example server.

FIG. 19 is a flow chart showing an example flow of the processes to be executed on the server. The flow chart shown in FIG. 19 is executed continuously, irrespective of the state of the hand-held terminal 5 (e.g., irrespective of whether it is an awake period or a sleep period of the user).

First, in step S81, the server 3 determines whether or not information has been received from the hand-held terminal 5. As described above, the hand-held terminal 5 transmits various information to the server 3 at appropriate points in time. Information the server 3 receives from the hand-held terminal 5 includes, for example, the health information transmitted in step S37, the health information transmitted in steps S47 and S60 (specifically, the corrected energy level), the awake information calculated in step S51 (herein, the activity information, the environment information and the emotion information), etc. When the various information are received by the server 3, the determination result of step S81 becomes affirmative. On the other hand, if the various information have not been received by the server 3, the determination result of step S81 is negative. If the determination result of step S81 is affirmative, the process of step S82 is executed. On the other hand, if the determination result of step S81 is negative, the process of step S83 to be described later is executed, skipping the process of step S82.

In step S82, the server 3 stores (or "accumulates"), for each user, information received from the hand-held terminal 5. That is, the processing section (specifically, the CPU) of the server 3 updates user data representing various information of the user so that the received information are included in the user data. The user data stored in the server 3 will now be described.

Figure 20:
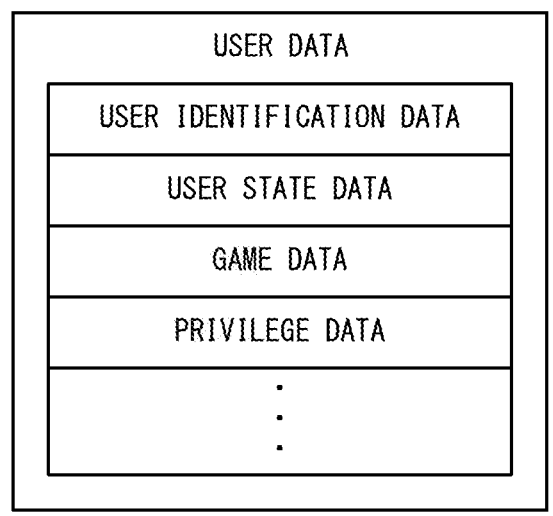
FIG. 20 shows an example data configuration of user data stored in an example server according to the present embodiment.

FIG. 20 shows an example data configuration of the user data stored in the server of the present embodiment. FIG. 20 shows the user data stored in the server 3 for one user. Although not shown in the figure, the server 3 stores, in a predetermined storage section, data similar to the user data shown in FIG. 20, for each of the users of the network service.

As shown in FIG. 20, the user data includes user identification data, user state data, game data and privilege data. A set of these four different data is accumulated in the server 3 for each user. Note that the user data may include other data in addition to these four data, and may not include one or more of these four data. In other embodiments, the user data may include preference data representing the preferences of the user, for example. The user data may store, in addition to the user state data, information (e.g., the location information, the environment sensor information, etc.) used for calculating the information represented by the user state data.

The user identification data is data representing identification information (e.g., an ID or a password, etc.) for identifying the user. In the present embodiment, the identification information described above is set in a predetermined registration process to be executed when starting a network service for the user, and user identification data representing the identification information which has been set is stored in the server 3. In the present embodiment, when the hand-held terminal 5 transmits information to the server 3, the hand-held terminal 5 transmits the information, with the identification information included therein, to the server 3. The server 3 identifies the user, who is the sender, based on the identification information included in the received information.

The user state data is data representing various states of the user. In the present embodiment, the user state data includes data representing the health information, data representing the activity information, data representing the environment information, and data representing the emotion information. These four data each include more than one of the information that have been obtained. That is, in the present embodiment, the four data each represent, for example, pieces of information that have been obtained over a predetermined storage period (e.g., one year) including the latest and past pieces of information. Therefore, when information is received in step S81, the server 3, in step S82, updates one of the four data that corresponds to the received information so that the received information is included therein. Note that it is assumed for the server 3 that the same storage period is used for the four data, but the storage period of each of the four data may be of any length, and the storage periods may differ from each other.

The game data is data representing information relating to the game process using the health information as an input, and includes data representing the game result, etc. The game data may include data representing information relating to the mini-game described above (e.g., information of the result of the mini-game).

The privilege data is data representing a privilege awarded to the user. For example, the privilege data is data representing the history of privileges that have been awarded to the user.

Referring back to FIG. 19, in step S83, the server 3 determines whether or not to correct the energy level. That is, the processing section of the server 3 determines whether or not the information received in the last iteration of step S81 executed is awake information. If the determination result of step S83 is affirmative, the process of step S84 is executed. On the other hand, if the determination result of step S83 is negative, the process of step S85 to be described later is executed, skipping the process of step S84.

In step S84, the server 3 corrects the energy level based on the information received in step S81. That is, the processing section of the server 3 corrects the energy level based on the received information by the method described in "(Process during daytime)" above. The process of step S85 is executed, following step S84.

In step S85, the server 3 determines whether or not there has been a request from the hand-held terminal 5 to transmit game result information. If the determination result of step S85 is affirmative, the process of step S86 is executed. On the other hand, if the determination result of step S85 is negative, the process of step S81 is executed again, skipping the processes of steps S86 and S87.

In step S86, the server 3 awards a privilege to the user as necessary based on the information received in step S81. That is, based on the energy level at present, the processing section of the server 3 determines whether or not to award a privilege and, if awarded, what the privilege is. Note that the energy level at present is the latest energy level calculated for the day. Specifically, if the process of step S84 has been executed today, the energy level at present is the energy level as corrected in the last iteration of the process of step S84, and if the process of step S84 has not been executed today, the energy level at present is the energy level represented by the last information received in the process of step S81.

In the following step S87, the server 3 transmits the game result information described above to the hand-held terminal 5 that has sent the request in step S85. That is, the processing section of the server 3 generates game result information including the information representing the energy level at present and the information representing the privilege awarded in step S87, and transmits the game result information to the hand-held terminal 5. The process of step S81 is executed again, following step S87.

As described above, in the present embodiment, the process of correcting the energy level (step S84) is executed in response to receiving the various awake information for correcting the energy level, and the process of awarding a privilege (step S86) is executed in response to a request to transmit the game result information issued from the hand-held terminal 5. Herein, the process of step S84 is executed with any timing, and the process of step S85 is executed with any timing. For example, in other embodiments, the process of step S84 may be executed in response to the request described above. The process of step S85 may be executed in response to receiving the awake information.

The server 3 repeatedly executes the series of processes of steps S81 to S87 described above. Note that the server 3 executes the series of processes of steps S81 to S87 for each of the hand-held terminals owned by users of the network service.

Main information processes to be executed on the hand-held terminal 5 and the server 3 have been described above with reference to FIG. 15 to FIG. 19. The hand-held terminal 5 and the server 3 may execute information processes other than the various processes shown in FIG. 15 to FIG. 19. For example, the server 3 may administer a website for providing the network service described above. The user can access this website by using the hand-held terminal 5 in order to browse the evaluation result made on the server 3 and purchase a product, or the like, relating to recommendation information presented by the server 3. The hand-held terminal 5 accepts inputs for making various requests on the website and executes processes in accordance with the accepted inputs. For example, the request may be a request to log in to the website, a request to browse webpages within the website (e.g., including a page showing the evaluation result and a page for purchasing a product, or the like), and a request to purchase a product, or the like, etc. The server 3 executes a process in accordance with a request from the hand-held terminal 5. For example, if the request is a request to log in to the website, the server 3 transmits, to the hand-held terminal 5, information of a log-in image (specifically, a webpage). For example, if the request is a request to obtain a webpage, the server 3 transmits information of the webpage to the hand-held terminal 5.

4. Functions/Effects of Present Embodiment (Functions/Effects Deriving from Executing Processes of Application in Conjunction with Sleep State)

In the embodiment described above, the information processing system 1 executing an application (specifically, a game application) obtains user information for calculating the information relating to the sleep of the user (step S32). The information processing system 1 determines the state relating to sleep of the user based on the obtained user information (step S33, S35, S48, S61).

Herein, the term "state relating to sleep of the user" may be, for example, a sleep state of the user such as awakening (including mid-sleep awakenings) and sleep onset, or a state of the user before and after sleep, such as getting in bed and getting out of bed. Therefore, the "user information" above may be information with which the sleep state of the user can be calculated, or information with which the user's state before and after sleep can be calculated. That is, the user information may be information sensed by the Doppler sensor 24 (specifically, the biological information) or may be information representing the docking state between the hand-held terminal 5 and the base device 6. The term "state relating to sleep of the user" may be a state relating to the action of the user described above (e.g., awakening, sleep onset, getting in bed, and getting out of bed, etc.), or a state relating to evaluation relating to sleep (e.g., a state in which the energy level satisfies a predetermined condition; more specifically, a state in which an energy level is calculated such that the cumulative value of the damage given to the enemy character exceeds a predetermined amount).

The information processing system 1 executes a predetermined information process of the application in conjunction with the state relating to sleep of the user. Herein, the phrase "to execute an information process in conjunction with the state relating to sleep of the user" means to execute an information process in response to the state relating to sleep of the user becoming equal to a predetermined state or to execute an information process in response to the state relating to sleep of the user satisfying a predetermined condition. Note that in the embodiment described above, "to execute an information process in conjunction with the state relating to sleep of the user" is realized by executing an information process automatically or executing an information process in real time in response to the state relating to sleep of the user becoming equal to a predetermined state (or the state relating to sleep of the user satisfying a predetermined condition).

When "an information process is executed in conjunction with the state relating to sleep of the user", there may be correlation between the state and the content of the information process or there may be correlation between the result of the state and the result of the information process. For example, as an example of the former, an information process of causing the player object to act in accordance with the state relating to sleep of the user is executed in the embodiment described above. That is, in the embodiment described above, processes are executed for displaying an image representing the player object 51 acting in accordance with the user awakening, getting out of bed and getting in bed (step S11, S16, S21 shown in FIG. 6). As an example of the latter, an information process is executed so that a better game result is obtained in response to a better evaluation result being obtained for the state relating to sleep of the user in the embodiment described above. That is, in the embodiment described above, a process is executed for advancing the story of the game in accordance with the evaluation result for the state relating to sleep of the user (specifically, the game result) (step S22 shown in FIG. 6).

As described above, the information processing system 1 executes information processes in conjunction with the state relating to sleep of the user, and the user therefore does not need to perform an operation for causing the information processes to be executed. Thus, it is possible to simplify the user operation on the information processing system 1. Therefore, it is possible to improve the usability for the user.

Note that in the embodiment described above, the information processing system 1 automatically starts executing the predetermined information process in response to the determination that the user's state has become equal to a predetermined state. The information processing system 1 obtains user information one after another in real time within a predetermined period of time (step S32), determines the state relating to sleep of the user one after another based on the obtained user information (step S33, S36), and starts executing a predetermined information process in response to the user's state becoming equal to a predetermined state (step S40, S49, S72). As described above, a predetermined information process is executed in real time in response to the user's state becoming equal to a predetermined state. Note that the predetermined period of time is a period from when the user gets in bed until the user gets out of bed in the embodiment described above, but it may be any period. For example, in other embodiments, the predetermined period of time may be a period from when the user gets in bed or falls asleep until the user awakens, or may be a period specified by the user.

The term "automatically" as used herein means "without an operation (or instruction) from the user". That is, "to automatically execute an information process" means that the user does not need to perform an operation or give an instruction for executing the information process (more specifically, for starting the execution thereof). Note that "automatically" does not mean that the user is not requested to perform any operation (or give any instruction). For example, the information processing system 1 may give the user a notification of starting the execution of the predetermined information process, and may execute the predetermined information process unless a user instruction for not executing the predetermined information process is given within a predetermined amount of time of the notification. Alternatively, at the start of, or during, the execution of the predetermined information process, the information processing system 1 may request the user to input predetermined information to be used in the information process.

The term "in real time" as used herein is not limited to having immediacy in its strict sense. For example, the information processing system 1 may obtain user information after the passage of about seconds to tens of seconds since when the user information is sensed by a sensor, or the like. The information processing system 1 may execute a predetermined information process after the passage of about seconds to tens of seconds since when the user's state becomes equal to a predetermined state.

In the embodiment described above, the information processing system 1 calculates health information relating to sleep and/or fatigue of the user based on user information (step S33, S36), and executes the predetermined information process using the health information as an input to the application (step S40, S72, S73). Then, it is possible to execute an information process based on the health information without the user performing an instruction operation.

The information processing system 1 determines a parameter relating to an object (the player character) appearing in the application based on the health information, and executes the predetermined information process (step S40). Then, the parameter of the object changes based on the health information, and the health state of the user is therefore reflected in the state of the object. Thus, it is possible to keep the user interested in the health information and motivate the user to check the health information. Note that while the application is a game application in the embodiment described above, it may be any application other than games in other embodiments. While the parameter represents the number of lives remaining of the player object or the amount of damage given to the enemy character in the embodiment described above, the parameter may be of any content.

The information processing system 1 executes, as a predetermined information process, a predetermined game process in the game application (the process of calculating the amount of damage given to the enemy character in the embodiment described above) based on the health information. Then, the user can measure and check the health information as if by playing a video game, thus motivating the user to continuously take such actions.

Based on the health information, the information processing system 1 generates advice information and/or recommendation information for improving the content represented by the health information (the energy level in the embodiment described above) and presents the information to the user (FIG. 7, FIG. 8, step S40). Thus, it is possible to present information that is useful for the user. In the embodiment described above, the presentation of the advice information and/or recommendation information is done in the game application (i.e., in the game). By presenting these information in the game, it is possible to motivate the user to continuously check these information.

In the embodiment described above, the information processing system 1 executes the following processes as the predetermined information process.

Process of advancing story of game

Game process using game parameters based on user health information (specifically, the number of lives remaining or amount of damage given to enemy character)

Process of awarding privilege (item, etc.) in game

Thus, a game process is executed as the predetermined process using a game input that reflects the health information. Therefore, the user can measure and check the health information as if by playing a video game, thus motivating the user to continuously take such actions.

In the embodiment described above, the information processing system 1 determines if the user has awakened (if the user has gotten out of bed in other embodiments), and starts accepting an instruction input to start the execution of a predetermined wake-up game (i.e., a mini-game) in response to determining that the user has awakened (see FIG. 9). When such an instruction input is made, a wake-up game process is executed based on an operation input from the user (step S15, S19, S46, S59). Thus, the information processing system 1 can have the user play the wake-up game, there can be expected an effect of awakening the user through the play of the wake-up game.

When the wake-up game is executed, the information processing system 1 reflects the result of the wake-up game in the health information (step S47). Thus, the information processing system 1 can calculate the health information while reflecting the user's state after the user awakens.

The information processing system 1 reflects the result of the wake-up game in the health information on the condition that it is within a predetermined period of time from the point in time when the user awakens (or when the user gets out of bed in other embodiments) (step S53, S55). Then, it is possible to reduce the possibility that the health information is calculated while the state of the user after awakening is not properly reflected.

Note that in other embodiments, the information processing system 1 may accept an instruction input for starting the execution of the wake-up game on the condition that it is within a predetermined period of time from the point in time when it is determined that the user has awakened or gotten out of bed. Then, the wake-up game can be started within a predetermined period of time since when the user awakens or gets out of bed. That is, if the user wants to play the wake-up game, the user wakes up, even if the user is sleepy, to start the wake-up game. Thus, it is possible to motivate the user to wake up. Playing the wake-up game itself can be expected to have an effect of awakening the user. Note that the predetermined period of time may be, for example, a period until the passage of a predetermined amount of time from the above-described point in time, or a period from the above-described point in time until the user is in a predetermined state. Specifically, the predetermined period of time may be a period from the point in time when it is determined that the user has awakened until it is determined that the user has gotten out of bed. Alternatively, the predetermined period of time may be a period from the point in time when it is determined that the user has awakened or gotten out of bed until the point in time of sensing the user having left home.

The information processing system 1 executes a game process based on the health information and the result of the wake-up game (e.g., a game process relating to the game progress) (step S73). Then, it is possible to improve the playability of the game by using the plurality of game inputs, and thus to more strongly motivate the user to continuously measure and check the health information.

The information processing system 1 calculates information relating to fatigue of the user (the energy level in the embodiment described above) based on the input made by the user in the wake-up game process and the state relating to sleep of the user (step S47). Then, it is possible to calculate the fatigue-related information while reflecting the user's state after the user awakens. Note that the term "input made by the user in the wake-up game process" may be an input of a game operation in the wake-up game as in the embodiment described above, or may be an input of a user's answer to a questionnaire in the wake-up game.

In the embodiment described above, the information processing system 1 includes the hand-held terminal 5 including a sensor (specifically, the Doppler sensor 24) and a display device (specifically, the display 17), and the server 3 capable of communicating with the hand-held terminal 5 via a network. The hand-held terminal 5 obtains the sensor information from the sensor to display an image representing the result of the predetermined information process on the display device. The server 3 accumulates the data based on the state relating to sleep of the user (FIG. 20). Thus, the user can check the result of the predetermined information process using the hand-held terminal 5 and to store the data on the server 3.

(Functions/Effects Deriving from Advancing Game Process Based on Sleep State)

In the embodiment described above, the information processing system 1, which executes the application of the game, obtains user information for calculating the information relating to the sleep of the user (step S32). Based on the obtained user information, the information processing system 1 calculates the health information relating to sleep and/or fatigue of the user (step S36, S47, S84). The information processing system 1 controls the game progress in the application of the game based on the health information (step S40, S42, S49, S54, S55, S72, S73). Thus, the game progresses as the user measures the health information. Therefore, it is possible to have the player measure the health information as if by playing a video game, and to motivate the user to continuously measure and check the health information.

Note that the phrase "controlling game progress based on health information" may mean that the player object is controlled to act in accordance with the health information (e.g., the player object wakes up as the user awakens and the player object sets out for an adventure in response to the user getting out of bed) as in the embodiment described above, or may mean that the progress of the story of the game in the application of the game (e.g., the player object advancing to the next level) is controlled based on the health information. The phrase "controlling game progress based on health information" may mean that a parameter of the object appearing in the application of the game is grown in accordance with the health information. For example, when the energy level calculated in step S36 described above is greater than or equal to a predetermined value (that is, when the energy level is higher than a predetermined reference level), the hand-held terminal 5 may increase a certain parameter of the player object. Then, the player object will grow gradually as the energy level continues to be good.

The information processing system 1 automatically controls the game progress in response to the calculated health information satisfying a predetermined condition. For example, in the embodiment described above, the player object wakes up in response to the calculated health information indicating that the user has awakened. For example, in the embodiment described above, the player object advances to the next level in response to the energy level calculated so that the amount of damage given to the enemy character exceeds a predetermined amount. Then, since the game progresses without having the user perform game operations, it is made easier for the user to continue to progress the game (in other words, to measure the health information).

5. Variations (Variation Regarding Evaluation of Health Information)

In the embodiment described above, the evaluation result of the health information is calculated based on the health information calculated today (in other words, the health information calculated after the last sleep period). In other embodiments, the evaluation result of the health information may be calculated based on the past health information of the user, in addition to the health information calculated today.

For example, the hand-held terminal 5 may calculate the evaluation result based on the energy level newly calculated in step S36 (i.e., the energy level calculated today) and past energy levels. Specifically, the hand-held terminal 5 may determine whether or not the energy level calculated today has improved by a predetermined reference level or more (e.g., 5 points or more) from past energy levels (e.g., the average value of the energy level of the last month), and use the determination result as the evaluation result. Note that the evaluation result may be based on the difference between the numerical value based on new health information (e.g., the energy level of today) and the numerical value based on past health information (e.g., the average value of the energy level of the last month).

Thus, the information processing system 1 obtains the user information for a plurality of user's sleep periods (in other words, the sleep period of each day), and calculates the health information based on the user information for each of the plurality of user's sleep periods. The information processing system 1 makes an evaluation based on the comparison result between the health information for the latest sleep period (i.e., the sleep period this morning) and information based on the health information for another sleep period that is prior to the sleep period. Then, it is possible to make an evaluation based on the user's past health information, and to make an evaluation based on whether or not the user health information has improved, for example. By having the user check whether or not the health information has improved, it is possible to strongly motivate the user to improve the health of the user.

In other embodiments, the evaluation result of the health information may be calculated based on the health information for the user of the hand-held terminal 5 and the health information for another user. For example, the hand-held terminal 5 may obtain the average value of the energy level of the other user from the server 3, and calculate the evaluation result based on the obtained average value and the energy level calculated in step S36 (i.e., the energy level for the user of the hand-held terminal 5). Note that any user or users may be the other user(s) used for calculating the evaluation result. For example, it may be all the users registered on the network service or may be a user or users who satisfy predetermined selection criteria. The criteria may be those relating to personal information, such as region (e.g., nationality), age, sex and occupation, for example.

Thus, the information processing system 1 is capable of accessing a storage section (the storage section of the server 3) that stores health information for a plurality of users. The information processing system 1 may make an evaluation based on the comparison result between the health information for the user calculated on the terminal system 2 of the user and the health information for other users stored in the storage section. Then, it is possible to make an evaluation based on the health information of other users, and it is possible to, for example, make an evaluation whether or not the evaluation of the user of the hand-held terminal 5 is better than those for the other users. By having the user check the comparison result with the other users, it is possible to strongly motivate the user to improve health.

Also when the evaluation result is calculated reflecting past health information and/or when the evaluation result is calculated reflecting health information for other users, the game process may be executed based on the evaluation result as in the embodiment described above. That is, the hand-held terminal 5 may present a game element representing the evaluation result to the user, or may advance the game depending on the evaluation result.

Note that the hand-held terminal 5 may calculate each of a first evaluation result reflecting past health information (and/or health information for other users), and a second evaluation result not reflecting such health information (i.e., the health information of the user of the hand-held terminal 5 calculated today). Then, the hand-held terminal 5 may present, to the user, a game element representing the first evaluation result and a game element representing the second evaluation result. Then, two different evaluation results may be presented to the user in an easy-to-understand manner.

Figure 21:
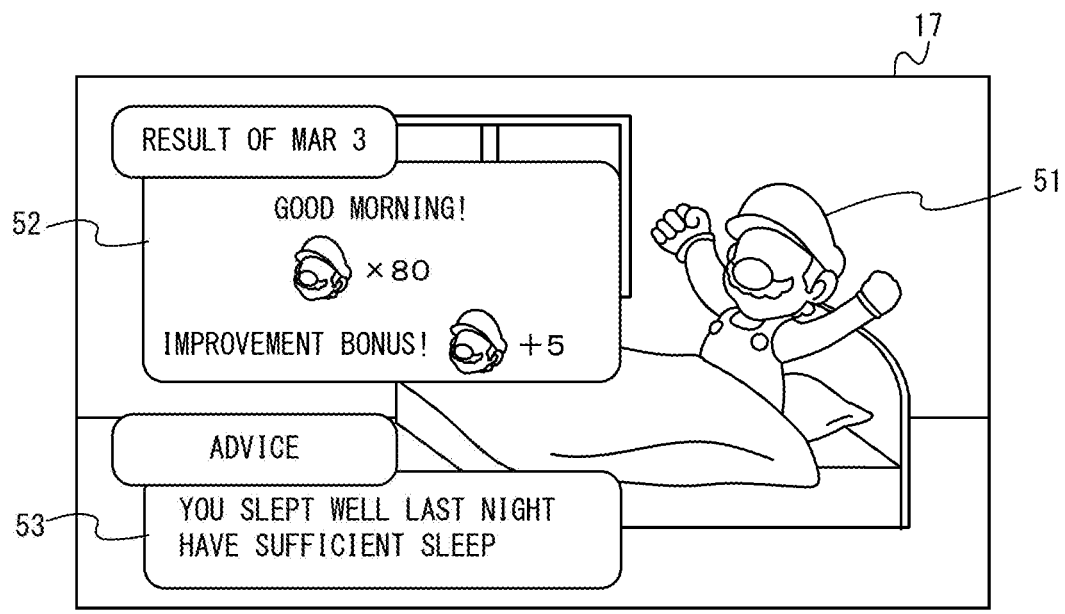
FIG. 21 shows an example game image to be displayed in a variation of the above embodiment.

FIG. 21 shows an example game image to be displayed in a variation of the embodiment described above. FIG. 21 shows a variation of the wake-up game image shown in FIG. 7. In the variation shown in FIG. 21, the hand-held terminal 5 determines whether or not the energy level of the health information calculated today has improved by a predetermined reference level or more from information based on past energy levels (e.g., the average value of the energy level of the last month). Then, when it is determined that the energy level has improved, the hand-held terminal 5 adds a number of lives as a bonus for the improvement of the health information. In this case, as shown in FIG. 21, the hand-held terminal 5 displays a number of lives ("5" in FIG. 21) to be added as the bonus to the number of lives remaining ("80" in FIG. 21) corresponding to the energy level calculated today. Note that when it is determined that the energy level has not improved, the hand-held terminal 5 does not add a number of lives as the bonus. In this case, a number of lives as the bonus is not displayed. Thus, it is possible to present, to the user, the energy level of the user himself/herself and the bonus for the improvement in an easy-to-understand manner.

Note that the game element representing the first evaluation result and the game element representing the second evaluation result may be the same game element, such as the number of lives remaining described above, or may be different game elements. For example, the hand-held terminal 5 may display, in the game image, an item to be awarded based on the first evaluation result, and display, in the game image, the number of lives remaining representing the second evaluation result. These two game elements may be displayed at the same time or may be displayed at different points in time.

(Variation Regarding Display Reflecting a Plurality of Health Information)

In the variation of the embodiment described above, when the hand-held terminal 5 displays the game image, it may display an image of an object that reflects a plurality of different health information calculated (the sleep indices and the fatigue index, etc.). For example, in the embodiment described above, a plurality of different sleep indices are calculated as the health information, and the hand-held terminal 5 may vary the color, shape and/or texture, etc., of the player object 51 depending on each of some of the sleep indices. Specifically, when the sleep time, the number of mid-sleep awakenings and the sleep quality level are used as the sleep indices, the facial expression of the player object 51 in the wake-up game image may vary depending on the sleep time, the hair of the player object 51 may vary depending on the number of mid-sleep awakenings, and the clothes of the player object 51 may vary depending on the sleep quality level. More specifically, the hand-held terminal 5 may be such that the facial expression of the player object 51 is more cheerful as the sleep time is closer to the ideal value, the hair of the player object 51 is messier as the number of mid-sleep awakenings is higher, and the color of the clothes is brighter as the sleep quality level is higher.

As described above, the information processing system 1 may generate, in the application, an image that changes depending on each of a plurality of health information (e.g., a plurality of different sleep indices), and display the generated image on a predetermined display device (herein, the display 17). Then, the measurement result of a plurality of health information can be presented in such a manner that the user is likely able to intuitively grasp the measurement result.

The information processing system 1 may display the image on the display device automatically in response to the determination that the user has awakened or gotten out of bed. For example, the hand-held terminal 5 may display the player object 51 of this variation in the wake-up game image and/or the out-bed game image of the embodiment described above. At the point in time when the user awakens or gets out of bed, the user has just woken up and it may be difficult for the user to understand the various numerical values representing a plurality of health information presented to the user. In contrast, according to this variation, such an image as described above is presented to the user, and the user can generally grasp the calculation result of the health information of that morning.

The information processing system 1 changes the display mode of the first type relating to a predetermined object appearing in the application depending on the first health information (of a plurality of health information), and changes the display mode of the second type relating to the object depending on the second health information (of the plurality of health information). Note that "to change the display mode of an object" means to include changing the color, shape, size and/or texture relating to the whole or part of the object, and changing the number of the objects. Thus, as the display mode for an object is changed, the user can know the calculation result of the health information of the user by looking at the object.

Figure 22:
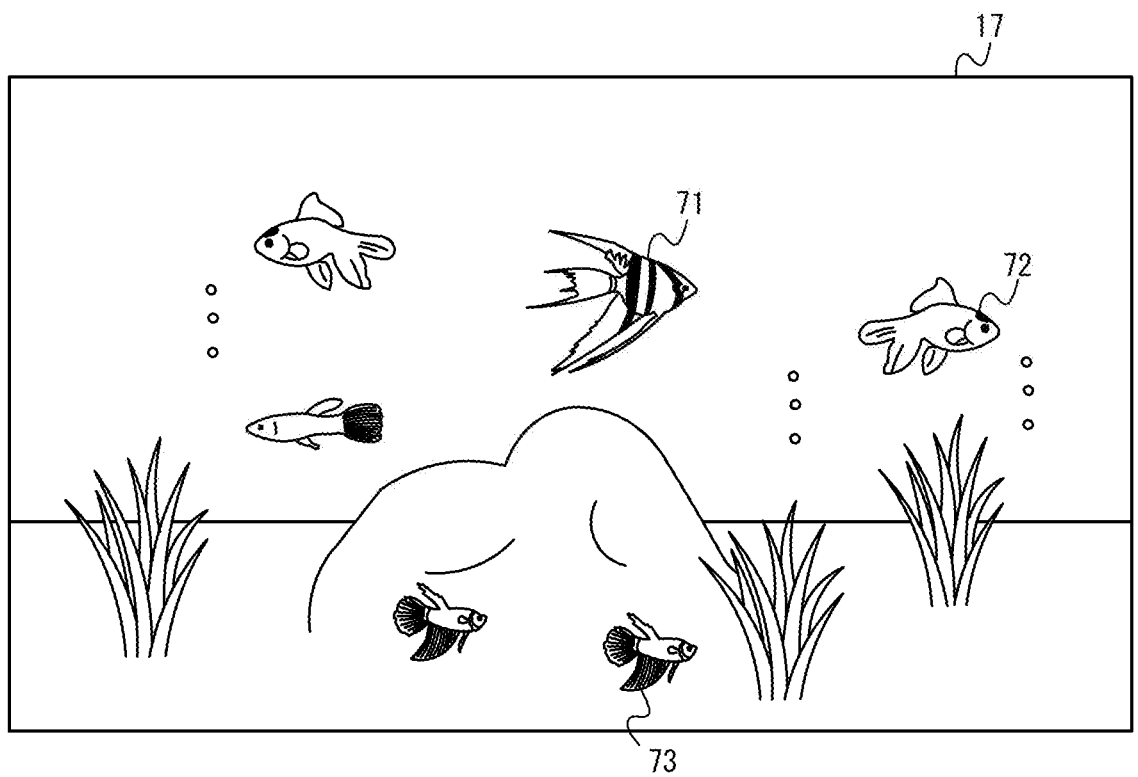
FIG. 22 shows an example image to be displayed in a variation of the above embodiment.

Note that the predetermined object does not need to be a single object, and the information processing system 1 may change the display mode for a plurality of objects of the same type. FIG. 22 shows an example image to be displayed in the variation of the embodiment described above. In the example shown in FIG. 22, a tropical fish raising application is executed on the information processing system 1, and the image shown in FIG. 22 is displayed on the display 17. In the example described above, depending on each of a plurality of health information, the information processing system 1 varies the number of tropical fish corresponding to the health information. For example, the hand-held terminal 5 may increase the number of first fish objects 71 as the sleep time is closer to the ideal value, increase the number of second fish objects 72 as the number of mid-sleep awakenings is smaller, and increase the number of third fish objects 73 as the sleep quality level is higher. Then, the user can recognize how good or bad each sleep index is based on the number of fish objects of each type, and can recognize how good or bad the health information (specifically, sleep) is based on the total number of fish objects.

The information processing system 1 may change the display mode for each of a plurality of different images (which may be the image of an object or the background image). For example, in the example shown in FIG. 22, the information processing system 1 may change the display mode of the fish object depending on the first health information, and may change other display modes such as the amount of water weed, the size of water weed and/or the clarity of water, etc., depending on the second health information (which is different from the first health information).

(Variation Regarding Communication with Terminals of Other Users)

In other embodiments, the terminal system 2 may give notifications to hand-held terminals of other users (referred to as "other user terminals") in response to the state relating to sleep of the user (e.g., awakening, sleep onset, getting in bed, getting out of bed, etc.). For example, the hand-held terminal 5 may register, in advance, other user terminals to which notifications will be given, and in response to the user awakening or getting out of bed, the hand-held terminal 5 may give an notification that the user has woken up to the other user terminals. Alternatively, in response to the user falling asleep or getting in bed, the hand-held terminal 5 may give a notification that the user has gone to bed to the other user terminals. Then, the state relating to sleep of the user can be automatically notified to other users (e.g., family and friends). Note that the notification to the other user terminals from the hand-held terminal 5 may be done via the server 3 or without using the server 3.

In other embodiments, the terminal system 2 may transmit to the server 3 information representing the state relating to sleep of the user. That is, the server 3 may receive and store information representing the sleep-related state of each user on the network service from the terminal systems. Then, the server 3 may provide information based on the sleep-related state of other users to the terminal system 2. The terminal system 2 may obtain, from the server 3, information relating to other users who have been registered as "friends" in advance on the server 3, and present the obtained information to the user. Thus, the user of the terminal system 2 can know the current state (e.g., whether they are in bed or have gotten up, etc.) of other users who have been registered as "friends". The server 3 may provide information based on the state of a large number of unspecified other users to the terminal system 2. For example, the server 3 may transmit, to the terminal system 2, information representing the ratio of users who have been gotten up in a particular region. Then, the user can know the state of other users.

Information representing the sleep-related state of other users as described above may be presented in the game application. Then, the user's state may be represented by the state (or action) of the player object 51 of the embodiment described above. For example, when the user is sleeping, a game image representing the player object 51 being asleep may be displayed on hand-held terminals of other users.

(Variation Regarding Application)

While the embodiment described above is directed to an example in which a game application is executed on the terminal system 2, the type of an application to be executed on the terminal system 2 is not limited to a game but may be any type. When a game application is executed, the game may be of any genre or content. The terminal system 2 may control the game progress based on the health information in any of the following games, for example.

- A pet-raising game, in which a pet grows (parameters of the pet change) based on the user health information.
- A restaurant management game, in which a restaurant grows (the store becoming larger or the menu items increasing) based on the user health information. Based on the health information, an actual recipe may be awarded to the user.

A travel game, in which mileage points accumulate based on the health information, allowing the user to travel to distant places.

A game of keeping farms, meadows or gardens, in which animals or plants grow based on the health information.

(Variation Regarding Functions of Various Devices Included in Information Processing System 1)

In the embodiment described above, various processes of the information processing system 1 are executed by the base device 6, the hand-held terminal 5 and the server 3. The various processes of the information processing system 1 may each be executed by any of these three components (the base device 6, the hand-held terminal 5 and the server 3).

Although the base device 6 transmits the information sensed by the sensor to the hand-held terminal 5, information calculated from the sensed information may be transmitted in other embodiments. For example, the base device 6 may calculate and transmit biological information such as breathing and/or body movements to the hand-held terminal 5, may calculate and transmit the sleep indices to the hand-held terminal 5, and may calculate and transmit the health information (including the evaluation result) to the hand-held terminal 5.

The hand-held terminal 5 may transmit information received from the base device 6 and/or information sensed by the hand-held terminal 5, as they are, to the server 3, or may transmit information calculated from these information to the server 3. In either case, the server 3 may calculate the health information based on the information received from the hand-held terminal 5.

Note that when a plurality of different health information are calculated or a plurality of different evaluations are made as in the embodiment described above, the hand-held terminal 5 may calculate some of the plurality of different health information (including the evaluation result) while the server 3 calculates the remaining health information.

In other embodiments, the base device 6 may communicate with the server 3 without using the hand-held terminal 5 therebetween. For example, the base device 6 may have the function of communicating with the server 3 via the network 4, as does the hand-held terminal 5. Then, the base device 6 may transmit information sensed by the base device 6 directly to the server 3 or may transmit the information both to the hand-held terminal 5 and to the server 3. When the base device 6 can communicate with the server 3, the hand-held terminal 5 may obtain information from the base device 6 via the server 3. That is, when obtaining information from the base device 6, the hand-held terminal 5 may obtain, from the server 3, information that have been transmitted from the base device 6 to the server 3.

(Variation Regarding Sensor)

In the embodiment described above, the sensor for obtaining the biological information of the user is a sensor for sensing the biological information of the user while being not in contact with the user. That is, the sensor of the present embodiment is a non-contact type (and unworn type) sensor (specifically, a Doppler sensor). The sensor is placed in the vicinity of a user who is a subject to be sensed. Thus, the user need not worry about the sensing operation by the sensor, whereby the burden on the user, which is caused by sensing, can be reduced. In addition, the unworn type sensor avoids a situation that the user forgets to wear the sensor and sensing is not performed.

The non-contact type (and unworn type) sensor is not limited to the Doppler sensor 24 described above. That is, in the embodiment described above, the Doppler sensor 24 emits radio waves toward the subject to be sensed and receives reflected waves, and outputs the biological information on the basis of received results (by analyzing the movement of the subject on the basis of the Doppler phenomenon of the received waves). In other embodiments, for example, the non-contact type sensor may emit radio waves toward the subject to be sensed and receive reflected waves, and may output the biological information on the basis of received results (received waves). Specifically, the sensor may obtain an image of the subject on the basis of the received waves, analyze the movement of the subject from the image information, and output the biological information. The non-contact type sensor may be a sensor that uses predetermined sensing waves such as ultrasonic waves instead of radio waves. The non-contact type sensor may be an image-capturing unit (camera) placed in the vicinity of the user. That is, the camera may capture an image of the subject from a distant location, and the information processing system may analyze the movement of the subject from the captured image to output the biological information.

The embodiment described above can be used, for example, as an information processing system, or the like, for executing a game application, with the aim of simplifying the user operation, for example.

While certain example systems, methods, devices and apparatuses have been described herein, it is to be understood that the appended claims are not to be limited to the systems, methods, devices and apparatuses disclosed, but on the contrary, are intended to cover various modifications and equivalent arrangements included within the spirit and scope of the appended claims.

The invention claimed is:

1. An information processing system, comprising:
a sensor; and
an electronic device comprising:
  a memory for storing instructions; and
  one or more processors in communication with the memory, wherein the instructions, when executed, configure the one or more processors to:
    acquire awake information regarding a user including at least either of activity information indicating an activity performed by the user during awakening and environment information indicating an environment around the user during awakening;
    detect the user's getting in bed or homecoming; and
    on a condition that the user's getting in bed or homecoming is detected, display a game image indicating a state in which a game advances based on the acquired awake information, and
  in the game image, the awake information is reflected on at least one of a game space or a player object appearing in the game space.

2. The information processing system according to claim 1, wherein the game image includes an image of the player object reproducing the activity of the user indicated by the activity information.

3. The information processing system according to claim 1, wherein the game image includes an image of a game space representing the environment around the user indicated by the environment information.

4. The information processing system according to claim 1, wherein the game image includes a numerical value indicating an evaluation result of health of the user calculated based on the awake information.

5. The information processing system according to claim 1, wherein the instructions further configure the one or more processors to:
in a period before the user's getting in bed or homecoming is detected, display the game image indicating the state in which the game advances based on the awake information; and
the game image displayed on the condition that the user's getting in bed or homecoming is detected includes at least a part of the game image displayed in the period.

6. The information processing system according to claim 1, wherein the instructions further configure the one or more processors to:
calculate an evaluation result of health of the user based on the awake information; and
the game image includes advice information calculated based on the awake information and indicating advice for the user to improve the evaluation result.

7. The information processing system according to claim 1, wherein the game image includes information indicating a privilege that the user is to be awarded in accordance with a game result based on the awake information.

8. The information processing system according to claim 1, wherein the instructions further configure the one or more processors to:
acquire information regarding sleep of the user;
detect awakening of the user based on the information regarding the sleep; and
on a condition that the awakening of the user is detected, display a first numerical value indicating health of the user and calculated based on the information regarding the sleep; and
the game image displayed on the condition that the user's getting in bed or homecoming is detected includes a second numerical value calculated based on the awake information and of the same type as the first numerical value displayed on the condition that the awakening of the user is detected.

9. The according to claim 8, wherein the second numerical value is calculated by correcting the first numerical value based on the awake information.

10. The information processing system according to claim 1, wherein the instructions further configure the one or more processors to:
acquire information regarding sleep of the user;
detect awakening of the user based on the information regarding the sleep; and
on a condition that the awakening of the user is detected, display a game image representing that the player object starts a predetermined action; and
the game image displayed on the condition that the user's getting in bed or homecoming is detected includes an image representing that the player object ends the predetermined action.

11. The information processing system according to claim 10, wherein the instructions further configure the one or more processors to:
in a period from when the awakening of the user is detected to when the user's getting in bed or homecoming is detected, display a game image indicating the player object in the middle of performing the predetermined action.

12. The information processing system according to claim 1, wherein:
the awake information further includes emotion information indicating emotion of the user; and
the game image includes an image indicating the player object on which the emotion of the user indicated by the emotion information is reflected.

13. An information processing device comprising:
a memory for storing instructions; and
one or more processors in communication with the memory, wherein the instructions, when executed, configure the one or more processors to:
acquire awake information regarding a user including at least either of activity information indicating an activity performed by the user during awakening and environment information indicating an environment around the user during awakening;
detect the user's getting in bed or homecoming; and
on a condition that the user's getting in bed or homecoming is detected, display a game image indicating a state in which a game advances based on the acquired awake information, and
in the game image, the awake information is reflected on at least one of a game space or a player object appearing in the game space.

14. A non-transitory computer-readable storage medium storing an information processing program to be executed on a computer of an information processing device, the information processing program, when executed by the computer, causing the computer to:
acquire awake information regarding a user including at least either of activity information indicating an activity performed by the user during awakening and environment information indicating an environment around the user during awakening;
detect the user's getting in bed or homecoming; and
on a condition that the user's getting in bed or homecoming is detected, display a game image indicating a state in which a game advances based on the acquired awake information, and
in the game image, the awake information is reflected on at least one of a game space or a player object appearing in the game space.

15. An information processing method for executing on an information processing system that executes a game application, the method comprising:
acquiring awake information regarding a user including at least either of activity information indicating an activity performed by the user during awakening and environment information indicating an environment around the user during awakening;
detecting the user's getting in bed or homecoming; and
on a condition that the user's getting in bed or homecoming is detected, displaying a game image indicating a state in which a game advances based on the acquired awake information, and
in the game image, the awake information is reflected on at least one of a game space or a player object appearing in the game space.

* * * * *